US009968666B2

(12) United States Patent
Lu et al.

(10) Patent No.: US 9,968,666 B2
(45) Date of Patent: May 15, 2018

(54) METHODS AND COMPOSITIONS FOR PROMOTING A CELL-MEDIATED IMMUNE RESPONSE

(75) Inventors: Yichen Lu, Wellesley, MA (US); Nicholas Kushner, Framingham, MA (US); Amie Strong, Framingham, MA (US); Zhenghui Xu, Hainan (CN)

(73) Assignee: Vaccine Technologies, Incorporated, Wellesley, MA (US)

( * ) Notice: Subject to any disclaimer, the term of this patent is extended or adjusted under 35 U.S.C. 154(b) by 0 days. days.

(21) Appl. No.: 13/377,746

(22) PCT Filed: Jun. 11, 2010

(86) PCT No.: PCT/US2010/038313

§ 371 (c)(1), (2), (4) Date: Feb. 24, 2012

(87) PCT Pub. No.: WO2010/144800

PCT Pub. Date: Dec. 16, 2010

(65) Prior Publication Data

US 2012/0148621 A1 Jun. 14, 2012

Related U.S. Application Data

(60) Provisional application No. 61/186,440, filed on Jun. 12, 2009.

(51) Int. Cl.

| | |
|---|---|
| ***A61K 39/00*** | (2006.01) |
| ***A61K 39/04*** | (2006.01) |
| ***A61K 39/12*** | (2006.01) |
| ***C40B 40/10*** | (2006.01) |
| ***A01H 5/00*** | (2006.01) |
| ***A61K 39/07*** | (2006.01) |
| ***A61K 38/16*** | (2006.01) |
| ***A61K 38/19*** | (2006.01) |
| ***A61K 38/20*** | (2006.01) |

(52) U.S. Cl.

CPC ............ *A61K 39/07* (2013.01); *A61K 38/164* (2013.01); *A61K 38/193* (2013.01); *A61K 38/2013* (2013.01); *A61K 39/00* (2013.01); *A61K 39/04* (2013.01); *A61K 2039/6037* (2013.01)

(58) Field of Classification Search

CPC ............ A61K 2300/00; A61K 2039/53; C07K 14/445; C12N 15/102

USPC .......................................................... 424/208

See application file for complete search history.

(56) References Cited

U.S. PATENT DOCUMENTS

| | | | |
|---|---|---|---|
| 5,591,631 | A | 1/1997 | Leppla et al. |
| 5,674,698 | A | 10/1997 | Zarling et al. |
| 5,677,274 | A | 10/1997 | Leppla et al. |
| 6,592,872 | B1 | 7/2003 | Klimpel et al. |
| 2003/0190332 | A1 | 10/2003 | Gilad et al. |
| 2004/0166120 | A1 | 8/2004 | Thomas et al. |
| 2010/0311105 | A1 | 12/2010 | Lu et al. |

FOREIGN PATENT DOCUMENTS

| | | | |
|---|---|---|---|
| CN | 1636060 | A | 7/2005 |
| WO | 94/18332 | A2 | 8/1994 |
| WO | 94/18332 | A3 | 8/1994 |
| WO | 97/23236 | | 7/1997 |
| WO | 02/079417 | A2 | 10/2002 |
| WO | 2002/079417 | A2 | 10/2002 |
| WO | 2002/079417 | A3 | 10/2002 |
| WO | WO02079417 | * | 10/2002 |
| WO | 2008/048289 | A2 | 4/2008 |
| WO | 2008/048289 | A3 | 4/2008 |
| WO | WO2008127450 | * | 10/2008 |

OTHER PUBLICATIONS

Al-Attiyah et al., Clin Esp. Immunol, 2004, 138:139-144.*
Shu et al., Vaccine, 2006, 24:4409-4416.*
Anderson, K. S. et al., "Intracellular Transport of class I MHC Molecules in Antigen Processing Mutant Cell Lines" Journal of Immunology. 151:3407-3419 (1993).
Androlewicz, M. J. et al., "Evidence that transporters associated with antigen processing translocate a major histocompatibility complex class I-binding peptide into the endoplasmic reticulum in an ATP-dependent manner" Proc. Natl. Acad. Sci. USA, 90:9130-9134 (1993).
Ballard, J. D., et al., "Anthrax Toxin-Mediated Delivery In Vivo and In Vitro of a Cytotoxic T-Lymphocyte Epitope from Ovalbumin" Infection and Immunity. 66:615-619 (1998).
Borrow, P. et al., "Virus-Specific CD8+ Cytotoxic T-Lymphocyte Activity Associated with Control of Viremia in Primary Human Immunodeficiency Virus Type 1 Infection" J. Virol. 68, No. 9:6103-6110 (1994).
Borrow, P. et al., "Antiviral pressure exerted by HIV-1-specific cytotoxic T lymphocytes (CTLs) during primary infection demonstrated by rapid selection of CTL escape virus" Nature Medicine. 3:205-211 (1997).
Brodie et al., "In vivo migration and function of transferred HIV-1-specific cytotoxic T cells" Nat. Med. 5:34-41 (1999).
Cao, H. et al., "Cytotoxic T-Lymphocyte Cross-Reactivity among Different Human Immunodeficiency Virus Type 1 Clades: Implications for Vaccine Development" J. Virol. 71:8615-8623 (1997).

(Continued)

*Primary Examiner* — Barry A Chestnut
(74) *Attorney, Agent, or Firm* — Nixon Peabody LLP

(57) ABSTRACT

The present invention is directed to a method for promoting or stimulating a cell-mediated immune response to an antigen, by administering a target antigen (such as a protein) with a transport factor that contains a fragment of a bipartite protein exotoxin, but not the corresponding protective antigen. Preferred transport factors include the protective antigen binding domain of lethal factor (LFn) from *B. anthracis*, consisting of amino acids 1-255, preferably a fragment of at least 80 amino acids that shows at least 80% homology to LFn, and a fragment of about 105 amino acids from the carboxy portion that does not bind PA. The target antigen can include any molecule for which it would be desirable to elicit a CMI response, including viral antigens and tumor antigens.

20 Claims, 5 Drawing Sheets

(56) References Cited

OTHER PUBLICATIONS

Cao, H. et al., "Cellular Immunity to Human Immunodeficiency Virus Type 1 (HIV-1) Clades: Relevance to HIV-1 Vaccine Trials in Uganda" J. Infec Dis. 182:1350-1356 (2000).
Cao, H. et al., "Delivery of Exogenous Protein Antigens to Major Histocompatibility Complex Class I Pathway in cytosol" J. Infect. Dis. 185: 244-251 (2002).
Doling, A. et al., "Cytotoxic T-Lymphocyte Epitopes Fused to Anthrax Toxin Induce Protective Antiviral Immunity" Infection & Immunity. 67:3290-3296 (1999).
Falk, K. et al., "Identification of Naturally Processed Viral Nonapeptides Allows their Quantification in Infected Cells and Suggests an Allele-specific T Cell Epitope Forecast" J. Exp. Med. 174:425-434 (1991).
Finbloom, D. S. et al. "Endocytosis of particulate and soluble IgG immune complexes: differential effects of cytoskeletal modulating agents" Clinical & Experimental Immunology. 67:205-210 (1987).
Geisow, M. J. et al., "Temporal Changes of Lysosome and Phagosome pH during Phagolysosome Formation in Macrophages: Studies by Fluorescence Spectroscopy" Journal of Cell Biology. 89:645-652 (1981).
Goldberg, A. L. et al., "Proteolysis, proteasomes and antigen presentation" Nature. 357:375-379 (1992).
Hanna, P. C. et al., "On the role of macrophages in anthrax" Proc. Natl. Acad. Sci. USA. 90:10198-10201 (1993).
Letvin, "Progress in the Development of an HIV-1 Vaccine" Science 280:1875-1880 (1998).
Ogg, C. S. et al., "Quantitation of HIV-1-Specific Cytotoxic T Lymphocytes and Plasma Load of Viral RNA" Science 279:2103-2106 (1998).
Schmitz, J. et al., "Control of Viremia in Simian Immunodeficiency Virus Infection by CD8+ Lymphocytes" Science 283:857-860 (1999).
Arora, N. "Site directed mutagenesis of histidine residues in anthrax toxin lethal factor binding domain reduces toxicity" Molecular and Cellular Biochemistry; 177(1-2):7-14 (1997).
Barth, H. et al. "The N-Terminal Part of the enzyme Component (C2I) of the Binary Clostridium botulinum C2 Toxin Interacts with the Binding Component C2II and Functions as a Carrier System for a Rho ADP-Ribosylating C3-Like Fusion Toxin" Infection and Immunity; 66(4):1364-1369 (1998).
Falnes, P. O. et al. "Penetration of protein toxins into cells" Current Opinion in Cell Biology; 12(4):407-413 (2000).
Guidi-Rontani, C. et al. "Translocation of Bacillus anthracis lethal and oedema factors across endosome membranes" Cellular Microbiology; 2(3):259-264 (2000).
Gupta, P. et al. "Involvement of Residues 147VYYEIGK153 in Binding of Lethal Factor to Protective Antigen of Bacillus anthracis" Biochemical and Biophysical Research Communications; 280:158-163 (2001).
Kushner, N. et al. "A fragment of anthrax lethal factor delivers proteins to the cytosol without requiring protective antigen" PNAS; 100(11):6652-6657 (2003).
Stenmark, H. et al. "Peptides Fused to the amino-Terminal End of Diphtheria Toxin Are Translocated to the Cytosol" The Journal of Cell Biology; 113(5):1025-1032 (1991).
Goletz, T. et al., "Targeting HIV proteins to the major histocompatibility complex class I processing pathway with a novel gp120-anthrax toxin fusion protein" Proceedings of the National Academy of Sciences, USA, 94: 12059-12064 (1997).
Bowie et al., "Deciphering the Message in Protein Sequences: Tolerance to Amino Acid Substitutions" Science, 247: 1306-1310 (1990).
Bragg, T. et al., "Nucleotide sequence and analysis of the lethal factor gene (lef) from Bacillus anthracis," Gene, 81: 45-54 (1989).
Fayolle, C. et al., "In vivo induction of CTL responses by recombinant adenylate cyclase of Bordetella pertussis carrying viral CD8+ T cell epitopes," Journal of Immunology, 156:4697-4706 (1996).
Robertson, D. L., et al., "Molecular Cloning and expression in *Escherichia coli* of the lethal factor gene of Bacillus anthracis," Gene, 44:71-78 (1986).
Score Search Results, SEQ ID No. 2—alignment of result 1.
Robinson, E. et al., "Lymphocyte Stimulation by Phytohemagglutinin and Tumor Cells of Malignant Effusions" Cancer Research, 34:1548-1551 (1974).
Arora, N. et al., "Residues 1-254 of Anthrax Toxin Lethal Factor Are Sufficient to Cause Cellular Uptake of Fused Polypeptides" The Journal of Biological Chemistry, 268(5):3334-3341 (1993).
Arora, N. et al., "Cytotoxic Effects of a Chimeric Protein Consisting of Tetanus Toxin Light Chain and Anthrax Toxin Lethal Factor in Non-neuronal Cells" The Journal of Biological Chemistry, 269(42);26165-26171 (1994).
Figueiredo, D. et al., "Characterization of Recombinant Tetanus Toxin Derivatives Suitable for Vaccine Development" Infection and Immunity, 63(8):3218-3221, (1995).
Leppla, S. H. et al., "Anthrax toxin fusion proteins for intracellular delivery of macromolecules" Journal of Applied Microbiology, 87:284 (1999).
Tang, G. et al., "Proteasome Activity Is Required for anthrax Lethal Toxin to Kill Macrophages" Infection and Immunity, 67(6):3055-3060 (1999).
Lu, Y. et al., "Genetically modified anthrax lethal toxin safely delivers whole HIV protein antigens into the cytosol to induce T cell immunity" PNAS, 97(14):8027-8032 (2000).
Ballard, J. D. et al., "Anthrax toxin-mediated delivery of a cytotoxic T-cell epitope in vivo" Pro. Natl. Acad. Sci. USA 93:12531-12534 (1996).
Lacy, D. B. et al., "Mapping the Anthrax Protective Antigenn Binding Site on the Lethal and Edema Factors" The Journal of Biological Chemistry, 277(4):3006-3010 (2002).
Milne, J. C. et al., "Protective antigen-binding domain of anthrax lethal factor mediates translocation of a heterologous protein fused to its amino- or carboxy-terminus" Molecular Microbiology 15(4):661-666 (1995).
Al-Attiyah, R., et al., "In Vitro cellular immune responses to complex and newly defined recombinant antigens of *Mycobacterium tuberculosis,*" Clinical and Experimental Immunology, vol. 138, No. 1, Oct. 1, 2004, pp. 139-144.
Cao, H., et al., "Delivery of exogenous protein antigens to major histocompatibility complex class I pathway in cytosol," Journal of Infectious Diseases, University of Chicago Press, Chicago, IL, vol. 185, No. 2, Jan. 15, 2002 pp. 244-251.
Hepler, R. W., et al., "A recombinant 63-kDa form of Bacillus anthracis protective antigen produced in the yeast *Saccharomyces cerevisiae* provides protection in rabbit and primate inhalational challenge models of anthrax infection," Vaccine, Elsevier Ltd., vol. 24, No. 10, Mar. 6, 2006, pp. 1501-1514.
Kumar, T. D. Kaylan, et al., "Construction of a recombinant intergenus multidomain chimeric protein for simultaneous expression of haemolysin BL of Bacillus cereus, listeriolysin O of Listeria monocytogenes and enterotoxin B of *Staphylococcus aureus*." Journal of Medical Microbiology, May 2009, vol. 58. No Pt. 5, pp. 577-583.
Kushner, N. et al., "A fragment of anthrax lethal factor delivers proteins to the cytosol without requiring protective antigen," Proceedings of the National Academy of Sciences of the United States (PNAS), vol. 100, No. 11, May 27, 2003, pp. 6652-6657.
Lu, Y., et al., "Genetically modified anthrax lethal toxin safely delivers whole HIV protein antigens into the cytosol to induce T cell immunity," Proceedings of the National Academy of Sciences of the United States (PNAS), vol. 97, No. 14, Jul. 5, 2000, pp. 8027-8032.
Shu, L. et al., "Recombinant hepatitus B large surface antigen, successfully produced in *Escherichia coli*, stimulates T-cell response in mice," Vaccine, vol. 24, No. 20, May 15, 2006, pp. 4409-4416.
Song, H. et al., "High-level expression of codon optimized foot-and-mouth disease virus complex epitopes and cholera toxin B subunit chimera in Hansenula polymorpha," Biochemical and Biophysical Research Communications, Academic Press Inc., vol. 315, No. 1, Feb. 27, 2004, pp. 235-239.

(56) References Cited

OTHER PUBLICATIONS

Albrecht et al., "Immunogenicity and efficacy of an anthrax plague DNA fusion vaccine in a mouse model", FEMS Immunol Med Micribiol., 65:505-509 (2012).

Arora et al., "Fusions of Anthrax Toxin Lethal Factor to the ADP-ribosylation Domain of Pseudomonas Exotoxin A are Potent Cytotoxins Which are Translocated to the Cytosol of Mammalian Cells*", The Journal of Biological Chemistry, 267(22):15542-15548 (1992).

Arora et al., "Residues 1-254 of Anthrax Toxin Lethal Factor are Sufficient to Cause Cellular Uptake of Fused Polypeptides", The Journal of Biological Chemistry, 268(5):3334-3341 (1993).

Ballard et al., "Anthrax Toxin as a Molecular Tool for Stimulation of Cytotoxic T Lymphocytes: Disulfide-Linked Epitopes, Multiple Injections, and Role of CD4(+) cells", Infect Immunol., 66(10):4696-4699 (1998).

Ballard et al. "Anthrax Toxin-Mediated Delivery In Vivo and In Vitro of a Cytotoxic T-Lymphocyte Epitope from Ovalbumin", Infection and Immunity, 66(2):615-619 (1998).

Ballard et al., "Anthrax toxin-mediated delivery of a cytotoxic T-cell epitope in vivo", Pro. Natl. Acad. Sci. USA, 93:12531-12534 (1996).

Chandra et al., "Evaluation of the ability of N-terminal fragment of lethal factor of Bacillus anthracis for delivery of *Mycobacterium* T cell antigen ESAT-6 into cytosol of antigen presenting cells to elicit effective cytotoxic T lymphocyte response", Biochemical and Biophysical Research Communications, 351(3):702-707 (2006).

Doling et al., "Cytotoxic T-lymphocyte Epitopes Fused to Anthrax Toxin Induce Protective Antiviral Immunity", Infection & Immunity, 67(7):3290-3296 (1999).

Goletz et al., "Delivery of Antigens to the MHC Class I Pathway Using Bacterial Toxins", Human Immunology, 54(2):129-136 (1997).

Goletz et al., "Targeting HIV proteins to the major histocompatibility complex class I processing pathway with a novel gp120-anthrax toxin fusion protein", Proc. Natl. Acad. Sci. USA, 94:12059-12064 (1997).

Leppla et al., "Anthrax toxin fusion proteins for intracellular delivery of macromolecules", Journal of Applied Microbiology, 87:284 (1999).

Lu et al., "Genetically modified anthrax lethal toxin safely delivers whole HIV protein antigens into the cytosol to induce T cell immunity", PNAS, 97(14):8027-8032 (2000).

McEvers et al., "Modified anthrax fusion proteins deliver HIV antigens through MHC Class I and II pathways", Vaccine, 23(32):4128-4135 (2005).

Shaw et al., "Antigen Delivered by Anthrax Lethal Toxin Induces the Development of Memory CD8+ T Cells That Can Be Rapidly Boosted and Display Effector Functions", 76(3):1214-1222 (2008).

Shaw et al., "Both CD4+ and CD8+ T Cells Respond to Antigens Fused to Anthrax Lethal Toxin", Infect Immunol., 76(6):2603-2611 (2008).

Zhang et al., "Role of Furin in Delivery of a CTL Epitope of an Anthrax Toxin-Fusion Protein", Microbiol. Immunol., 45(2):119-125 (2001).

* cited by examiner

The amino acid sequence of lethal factor (LF) (SEQ ID NO: 1) which corresponds to LF with a signal peptide located at residues 1 to 33 at the N-terminus.

MNIKKEFIKVISMSCLVTAITLSGPVFIPLVQGAGGHGDVGMHVKEKEKNKDE
NKRKDEERNKTQEEHLKEIMKHIVKIEVKGEEAVKKEAAEKLLEKVPSD
VLEMYKAIGGKIYIVDGDITKHISLEALSEDKKKIKDIYGKDALLHEHYVYA
KEGYEPVLVIQSSEDYVENTEKALNVYYEIGKILSRDILSKINQPYQKFLD
VLNTIKNASDSDGQDLLFTNQLKEHPTDFSVEFLEQNSNEVQEVFAKAF
AYYIEPQHRDVLQLYAPEAFNYMDKFNEQEINLSLEELKDQRMLSRYEK
WEKIKQHYQHWSDSLSEEGRGLLKKLQIPIEPKKDDIIHSLSQEEKELLK
RIQIDSSDFLSTEEKEFLKKLQIDIRDSLSEEEKELLNRIQVDSSNPLSEK
EKEFLKKLKLDIQPYDINQRLQDTGGLIDSPSINLDVRKQYKRDIQNIDAL
LHQSIGSTLYNKIYLYENMNINNLTATLGADLVDSTDNTKINRGIFNEFKK
NFKYSISSNYMIVDINERPALDNERLKWRIQLSPDTRAGYLENGKLILQR
NIGLEIKDVQIIKQSEKEYIRIDAKVVPKSKIDTKIQEAQLNINQEWNKALG
LPKYTKLITFNVHNRYASNIVESAYLILNEWKNNIQSDLIKKVTNYLVDGN
GRFVFTDITLPNIAEQYTHQDEIYEQVHSKGLYVPESRSILLHGPSKGVE
LRNDSEGFIHEFGHAVDDYAGYLLDKNQSDLVTNSKKFIDIFKEEGSNLT
SYGRTNEAEFFAEAFRLMHSTDHAERLKVQKNAPKTFQFINDQIKFIINS
(SEQ ID NO: 1)

*FIG. 2A*

The amino acid sequence of lethal factor (LF) lacking the N-terminal Signal peptide (SEQ ID NO: 2) is as follows:

AGGHGDVGMHVKEKEKNKDENKRKDEERNKTQEEHLKEIMKHIVKIEVKGEEA
VKKEAAEKLLEKVPSDVLEMYKAIGGKIYIVDGDITKHISLEALSEDKKKIKDIYGK
DALLHEHYVYAKEGYEPVLVIQSSEDYVENTEKALNVYYEIGKILSRDILSKINQPY
QKFLDVLNTIKNASDSDGQDLLFTNQLKEHPTDFSVEFLEQNSNEVQEVFAKAF
AYYIEPQHRDVLQLYAPEAFNYMDKFNEQEINLSLEELKDQRMLSRYEKWEKIK
QHYQHWSDSLSEEGRGLLKKLQIPIEPKKDDIIHSLSQEEKELLKRIQIDSSDFLST
EEKEFLKKLQIDIRDSLSEEEKELLNRIQVDSSNPLSEKEKEFLKKLKLDIQPYDIN
QRLQDTGGLIDSPSINLDVRKQYKRDIQNIDALLHQSIGSTLYNKIYLYENMNINNL
TATLGADLVDSTDNTKINRGIFNEFKKNFKYSISSNYMIVDINERPALDNERLKWR
IQLSPDTRAGYLENGKLILQRNIGLEIKDVQIIKQSEKEYIRIDAKVVPKSKIDTKIQE
AQLNINQEWNKALGLPKYTKLITFNVHNRYASNIVESAYLILNEWKNNIQSDLIKK
VTNYLVDGNGRFVFTDITLPNIAEQYTHQDEIYEQVHSKGLYVPESRSILLHGPSK
GVELRNDSEGFIHEFGHAVDDYAGYLLDKNQSDLVTNSKKFIDIFKEEGSNLTSY
GRTNEAEFFAEAFRLMHSTDHAERLKVQKNAPKTFQFINDQIKFIINS (SEQ ID NO: 2)

*FIG. 2B*

The amino acid sequence of LFn (SEQ ID NO: 3) with a N-terminal signal peptide located at residues 1 to 33:
MNIKKEFIKVISMSCLVTAITLSGPVFIPLVQGAGGHGDVG
MHVKEKEKNKDENKRKDEERNKTQEEHLKEIMKHIVKIE
VKGEEAVKKEAAEKLLEKVPSDVLEMYKAIGGKIYIVDGDI
TKHISLEALSEDKKKIKDIYGKDALLHEHYVYAKEGYEPVL
VIQSSEDYVENTEKALNVYYEIGKILSRDILSKINQPYQKFL
DVLNTIKNASDSDGQDLLFTNQLKEHPTDFSVEFLEQNS
NEVQEVFAKAFAYYIEPQHRDVLQLYAPEAFNYMDKFNE
QEINLS (SEQ ID NO: 3)

*FIG. 2C*

The amino acid sequence of LFn lacking the N-terminus signal peptide corresponds to SEQ ID NO: 4 is as follows:
AGGHGDVGMHVKEKEKNKDENKRKDEERNKTQEEHLKEI
MKHIVKIEVKGEEAVKKEAAEKLLEKVPSDVLEMYKAIGGKI
YIVDGDITKHISLEALSEDKKKIKDIYGKDALLHEHYVYAKEG
YEPVLVIQSSEDYVENTEKALNVYYEIGKILSRDILSKINQPY
QKFLDVLNTIKNASDSDGQDLLFTNQLKEHPTDFSVEFLEQ
NSNEVQEVFAKAFAYYIEPQHRDVLQLYAPEAFNYMDKFN
EQEINLS (SEQ ID NO: 4)

*FIG. 2D*

The amino acid sequence for a “functional fragment” of LFn that transports or increases the transport of an antigen across a target cell membrane. One example of a fragment of LFn is a C-terminal fragment of LFn corresponding to SEQ ID NO: 5 as follows:

GKILSRDILSKINQPYQKFLDVLNTIKNASDSDGQDLLFTN
QLKEHPTDFSVEFLEQNSNEVQEVFAKAFAYYIEPQHRD
VLQLYAPEAFNYMDKFNEQEINLS (SEQ ID NO: 5)

*FIG. 2E*

METHODS AND COMPOSITIONS FOR PROMOTING A CELL-MEDIATED IMMUNE RESPONSE

CROSS REFERENCE TO RELATED APPLICATION

This Application is a 35 U.S.C. § 371 National Phase Entry Application of International Application No. PCT/US2010/038313 filed Jun. 11, 2010, which designates the U.S., and which claims benefit under 35 U.S.C. § 119(e) to U.S. Provisional Application 61/186,440, filed, Jun. 12, 2009, the entire contents of which is incorporated herein by reference.

FIELD OF THE INVENTION

The present application is generally directed to compositions for delivering an exogenous protein to the cytosol of a cell, and methods and thereof.

BACKGROUND OF THE INVENTION

Vaccines:

Vaccination is the administration of an antigenic material (the vaccine) to produce immunity to a disease. Vaccines can be used to prevent (i.e. prophylactic use) or ameliorate (i.e. therapeutic use) the effects of a pathology, for example an infection by a pathogen. Vaccination is considered to be the most effective and cost-effective method of preventing infectious diseases. The material administered as an immunogen are generally live but weakened or attenuated forms of pathogens (bacteria or viruses), killed or inactivated forms of these pathogens, or purified material such as proteins.

The antigenic material (also called an immunogen) stimulates a response in an animal against the respective pathogen following the initial administration and also in future encounters with the pathogen, thus providing protection against infection by the pathogen in future exposures. Smallpox was the first disease people tried to prevent by purposely inoculating themselves with other types of infectious agents. For example, the cowpox vaccine was used as an immunization for smallpox in humans by the British physician Edward Jenner in 1769.

However, not all vaccines and the immunogens in them are equally effective in stimulating an effective immune response. For example, poor immunogenicity of vaccines available against tuberculosis (TB), *Streptococcal pneumonia* (SP), measles virus Edmoston-Zagreb strain (EZMV), meningococci, hemagglutinin (HA) of influenza viruses, and hepatitis B virus have been reported. Moreover, some vaccines require an extended period of vaccination regime before immunity is successfully induced. For example, the primary basic vaccination against *Bacillus anthracis* requires six doses, three subcutaneous injections in the deltoid at zero, two, and four weeks, and three vaccinations at six, twelve, and eighteen months followed by annual boosters. For prolonged protection, annual boosters are required.

One reason accounting for the poor immunogenicity of some vaccines is the inability of some immunogens to enter the cytosol and the major histocompatibility complex pathway in order to stimulate a cell-mediated immune response. A number of bacterial toxins contain domains that share the ability to gain access to the host cell cytosol, where they can exert their effects. Although each toxin can differ in the mechanism or route by which it gains entry to the cytosol, the overall effect is that of a "molecular syringe" that is able to inject the toxic protein into the cell. Several bacterial toxins, including diphtheria toxin (DT), *Pseudomonas* exotoxin A (PE), pertussis toxin, and the pertussis adenylate cyclase have been used in attempts to deliver peptide epitopes to the cell cytosol as internal or amino-terminal fusions. These systems are restricted in their use as potential vaccines because their capacity to deliver larger protein antigens is limited and many individuals have already been immunized against the carrier toxin.

Although peptides are able to stimulate a cellular immune response, whole protein antigens can be better suited for use in an effective vaccine for two reasons. First, the epitope that is essential for protection in one genetic background can prove to be irrelevant in a different genetic background. Therefore, it is beneficial for a broadly applied T cell vaccine to use the full-length protein from which the various relevant epitopes are derived. Second, peptides recognized by cytotoxic T lymphocytes are processed from the whole protein by specialized degradative machinery, including the proteasome complex. In certain instances, the processing of the relevant peptide epitopes is dependent on the flanking amino acid sequences. However, flanking residues are not always important for proper processing. Because it currently is not possible to accurately predict which epitopes are dependent on their context for proper processing, it is important to deliver the entire antigen to the cell cytosol for optimal processing and presentation. Therefore, there is a need for new vaccines/immunogens that are more immunogenic, e. g. immunogens that consist of the whole polypeptide or larger portions thereof and/or novel strategies for introducing the vaccines/immunogen into cells to elicit an immune response.

Adjuvants:

The effectiveness of vaccines is often increased by giving them in adjuvants. An effective immune responses against malignancies and against several infectious pathogens are mediated by T cells. In particular, T helper epitopes are necessary for the induction of high titers of antigen-specific IgG antibodies. An adjuvant or immunostimulator can be used to enhance either humoral or cellular immunity or both. As a result, less recombinant antigen is needed for a standard vaccine or the low-responders respond effectively without increasing the antigen dose.

The primary purpose of an adjuvant is to enhance the immune response to a particular antigen of interest. In the context of antibody production for research purposes, adjuvants stimulate the rapid and sustained production of high titers of antibodies with high avidity. This permits ready recovery of antibody for further research in vitro. Adjuvants have the capability of influencing titer, response duration, isotype, avidity and some properties of cell-mediated immunity. The use of adjuvants is required for many antigens which by themselves are weakly immunogenic.

Adjuvants can increase the immune response to a particular antigen of interest through three basic mechanisms. The first is to enhance long term release of the antigen by functioning as a depot. Long term exposure to the antigen should increase the length of time the immune system is presented with the antigen for processing as well as the duration of the antibody response. The second is the interaction the adjuvant has with immune cells. Adjuvants can act as non-specific mediators of immune cell function by stimulating or modulating immune cells. Adjuvants can also enhance macrophage phagocytosis after binding the antigen as a particulate (a carrier/vehicle function).

The choice of the appropriate adjuvant is exceedingly important from both the aspect of the end result (high antibody response) as well as the immunized animal's welfare. Many of the adjuvants have the capacity to cause inflammation, tissue necrosis and pain in animals, and are thus not suited for human vaccination.

Typically, selection of an adjuvant is based upon antigen characteristics (size, net charge and the presence or absence of polar groups), as well as minimizing discomfort. For many years the only effective adjuvant available was complete Freund's adjuvant (CFA). In the past, adjuvants have also been selected based upon the species to be immunized, as some adjuvants will work better than others depending on the species. However, adjuvant selection remains largely empirical.

Antigens that are easily purified or available in large quantities can be good choices for starting with the least inflammatory adjuvants for immunization. Antigens which are difficult to come by (e.g., very small quantities are available), as well as small molecular weight compounds or weakly immunogenic antigens are more suitable candidates for combination with an adjuvant to increase the immune response.

Typically, adjuvants slow antigen release for a more sustained immune stimulation, bind toll-like receptors on macrophages and dendritic cells to stimulate production of inflammatory cytokines, and/or activate antigen presenting cells to express factors, including IL-10, that stimulate T cell activation. IL-10 is implicated in the adaptive immune response in humans, in particular, in promoting the development of Th2-lymphocytes from naïve (Th0) cells. Th2-lymphocytes recognize antigens presented by B-lymphocytes. Th2 cells, in turn, produce cytokines, including interleukins 2, 4, 5, 10, and 13, which promote antibody production. In addition, the production of IL-4 by Th2 cells enables the animal to make a quick antibody response that is essential to resistance to pathogenic antigens.

Collectively these cytokines enable activated B-lymphocytes to proliferate and stimulate activated B-lymphocytes to synthesize and secrete antibodies, promote the differentiation of B-lymphocytes into antibody-secreting plasma cells, and enable antibody producing cells to switch the class of antibodies being produced. Thus, an adjuvant is an important element of a good immune response to an antigen presented in a vaccine.

Complete Freund's Adjuvant (CFA), a mineral oil emulsion adjuvant, was, for many years, the adjuvant of choice because of the ability of CFA to boost antibody production following vaccination. However, CFA, while immunogenically potent, frequently produced abscesses, granulomas, and tissue sloughs. In addition, multiple exposures to CFA are known cause severe hypersensitivity reactions, and accidental exposure of personnel to CFA can result in sensitization to the associated antigen. Another common adjuvant frequently used for vaccine antigen delivery is aluminum salt ("alum"). Most alum adjuvants are generally weaker adjuvants than emulsion adjuvants, and generally cause only mild inflammatory reactions. However, alum is best used with strongly immunogenic antigens, and is thus not always appropriate.

Furthermore, in order to generate a CMI response, an antigen must be delivered to the interior of the cell. Exogenous proteins are poorly taken up by the cell. Accordingly, the preferred method has been using procedures such as viral vectors, liposomes, naked DNA or a similar approach. However, such approaches have many draw backs. For example, many recombinant viruses generate antigenic reactions themselves, upon repeated administration. Since standard forms of generating immune reactions typically require an initial injection, referred to as the prime, and subsequent injections, referred to as boosts, to achieve a satisfactory immunity, this can be a serious problem. Moreover, while much attention has been placed on improving the safety of viral vectors, there are always certain risks. For example, many of the target populations, such as those infected with HIV, can have a weakened immune system. Thus, certain viral vectors that are perfectly safe in many individuals can pose some degree of risk to these individuals.

It would be desirable to use an adjuvant which assist in facilitating delivery of an antigen into the interior of a cell in order to generate a CMI response.

SUMMARY OF THE INVENTION

The inventors have previously established that a fragment of the lethal factor (LF) polypeptide of *Bacillus anthracis* (*B. anthracis*) can deliver a fused target antigen to the cytosol of an intact cell. In particular, the inventors have previously demonstrated that in the absence of PA, a target antigen which is covalently attached (i.e. by a covalent bond or fused) to an LF polypeptide such as LFn or a fragment thereof can be used to deliver an antigen to the cytosol of an intact, living cell and elicit a CTL response to the fused antigen. The inventors herein have surprisingly discovered that it is not necessary for the target antigen to be fused to an LF polypeptide to be delivered to the cell cytosol and/or promote a cell-mediated immune response in the absence of PA. Thus, the inventors have now surprisingly discovered that LF polypeptides, such as LFn and fragments or variants thereof can be used to promote a cell-mediated immune response in the absence of PA. Accordingly, one aspect of the present invention described herein relates to the use of LF polypeptides, such as LFn or fragments or variants of LFn as an immune adjuvant to promote a cell-mediated immune response without the need for the LFn polypeptide to be covalently linked to the antigen. In one aspect, the LF polypeptide useful in the methods and compositions described herein is not physically linked or associated, or at least not substantially physically associated with the target antigen polypeptide. In an alternative aspect, the LF polypeptide is physically associated with the target antigen peptide, e.g. by being in a non-covalently bound complex with the target antigen polypeptide.

One aspect of the present invention provides compositions for delivering a target antigen to the cytosol of a cell and uses thereof. In particular, one aspect relates to a composition comprising an LF polypeptide and a target antigen, and methods of using such compositions to direct an immune response against the antigen, where the composition comprises an LF polypeptide and a target antigen which is not covalently linked to the LF polypeptide. The LF polypeptide or a fragment thereof functions to enhance the efficacy of a vaccine antigen to direct an immune response to the target antigen. In particular, in one aspect, compositions can comprise at least one LF polypeptide, such as for example, the N-terminal Lethal Factor (LFn) of a bipartite exotoxin such as *B. anthracis*, or a fragment or variant thereof, and at least one target antigen that is not covalently linked to the LF polypeptide.

Accordingly, one aspect of the present invention relates to a composition consisting essentially of LF polypeptide, such as for example, the N-terminal Lethal Factor (LFn) of a bipartate exotoxin such as *B. anthracis* and a target antigen, where the LFn is not covalently linked to the target antigen and the composition does not comprise a protective antigen (PA) of *B. anthracis.*

One aspect of the invention provides a means for eliciting a specific immune response, in particular a CMI response to a target antigen, whereby the target antigen is delivered to the cytosol of a cell by a composition consisting essentially of an LF polypeptide, for example, the N-terminal Lethal Factor (LFn) polypeptide or a fragment or variant thereof, and at least one target antigen that is non-linked or not covalently linked to the LF polypeptide.

In some embodiments, a preferred protein for delivery of antigens to the cytosol of a cell is the N-terminal fragment of the Lethal Factor, herein referred to as “LFn” and corresponds to SEQ ID NO:1. LFn of SEQ ID NO: 1 is an N-terminal fragment of Lethal Factor (LF) which comprises a binding region which binds to the protective antigen (PA).

Other aspects of the present invention relate to the use of a composition comprising an LF polypeptide and a target antigen that is not covalently linked to the LF polypeptide as described herein. In one aspect, a composition comprising an LF polypeptide and a target antigen that is not covalently linked to the LF polypeptide can used in a vaccine composition for immunization of a subject against a specific target antigen, such as a pathogen (protective or prophylactic vaccination) or for therapeutic treatment for ailments such as cancer, or diseases involving misfolded proteins, gain of function proteins (including for example polyglutamine diseases), aggregated proteins (i.e. disease involving amyloids) as well as specific diseases including but not limited to Alzheimer’s disease, Creutzfeldt-Jakob disease (CJD), variant Creutzfeldt-Jakob disease (vCJD), ‘Kuru’ or scrapie.

In one embodiment of this aspect, a composition comprising an LF polypeptide and a target antigen that is not covalently linked to the LF polypeptide can be used in screening for exposure to pathogens, for example, in a CMI response assay. An LF polypeptide and non-covalently linked target antigen provide a strategy of introducing an antigen into an intact cell. An LF polypeptide and non-covalently linked target antigen also provide a strategy to induce an immune response in a subject. In some embodiments, an LF polypeptide and non-covalently linked target antigen permit an antigen to enter into a cell, facilitate the display of the antigen or fragments thereof by MHC molecules so as to induce an immune response in a subject and thereby produce immunity against a pathogen having that antigen.

Another aspect of the present invention relates to a method of introducing an intracellular pathogen target antigen polypeptide to a mammalian cell, the method comprising contacting an LF polypeptide such as LFn and a target antigen that is not covalently linked to the LF polypeptide as described herein with a mammalian cell. In some embodiments, an LF polypeptide and a non-covalently linked target antigen contact the cell concurrently (i.e. simultaneously or at the same time) or alternatively, a cell can be contacted with an LF polypeptide and subsequently within a certain time frame a non-covalently linked target antigen, or vice versa. An appropriate time frame between the contact a cell with an LF polypeptide and a non-covalently linked target antigen can be any time period which allows the LF polypeptide to promote transmembrane delivery of the non-covalently target antigen into the cytosol of an intact cell. Such a time period can be, for example, nanoseconds, milliseconds, seconds or even minutes.

In one embodiment of this aspect, the LF polypeptide, such as LFn non-covalently linked to the target antigen promotes transmembrane delivery to the cytosol of an intact cell. In one embodiment, the cell is a mammalian cell in vivo and the method comprises administering an LF polypeptide and target antigen that is not covalently linked to the LF polypeptide to the mammal. A target antigen polypeptide normally cannot traverse the plasma membrane and enter an intact cell on its own. There are several contributing factors, the size of the polypeptide for one. Proteins in aqueous solutions tend to have their polar amino acid residues on the outside of the folded structure and the non-polar amino acid residues on the inside. The lipid bi-layer of the plasma membrane, being non-charged, repels the externally charged protein, preventing translocation of the protein across the membrane. Proteins can enter a cell by a number of ways, via protein channels which require expenditure of energy or via specific cell surface receptor mediated phagocytosis and/or endocytosis, both of which also require expenditure of energy. An LF polypeptide, such as LFn can itself traverse the plasma membrane and enter an intact cell on its own. It is known that a target antigen which is physically linked (i.e. by way of a peptide bond or as fusion protein) with an LF polypeptide can be translocated into the cytosol of an intact cell. The inventors herein have surprisingly discovered that a target antigen polypeptide which is non-covalently linked to LFn can also be delivered into an intact cell. This method is applicable to any non-covalently linked target antigen polypeptide, including, but not limited to., any intracellular pathogen antigen polypeptide. In other words, as long as a protein is to be delivered in an intact cell, this method can be used to achieve that goal, i. e., by contacting a cell with a target antigen in the presence of an LF polypeptide such as LFn, the LF polypeptide can promote transmembrane delivery of the non-covalently linked target antigen to the cytosol of an intact cell. No special knowledge of specific protein channels or specific cell surface receptor for the target antigen polypeptide is needed. In one embodiment, an LF polypeptide such as LFn is N-glycosylated. To introduce an antigen polypeptide to a mammalian cell, an LF polypeptide and a target antigen that is not covalently linked to the LF polypeptide are simply mixed and contacted with the mammalian cell. In a mammalian subject, an LF polypeptide such as LFn and a non-covalently linked target antigen can be administered to the subject. Topical and systemic routes of administration are possible, e. g., parenteral, nasal inhalation, intratracheal, intrathecal, intracranial, intramuscular, intraperitoneal, intracerebrospinal, subcutaneous, intra-arterial, intrasynovial, oral, and intrarectal.

Another aspect of the present invention relates to a method of raising a CMI response to a target antigen polypeptide, the method comprising administering to a mammal an LF polypeptide such as LFn and a non-covalently linked target antigen, where the LF polypeptide promotes transmembrane delivery of the non-covalently linked target antigen to the cytosol of an intact cell. Preferably, an LF polypeptide such as LFn and a non-covalently linked target antigen described as herein are formulated as a vaccine composition for administering to a mammal. In some aspects, any of the LF polypeptides, such as LFn, and non-covalently linked target antigens described herein can be used in a vaccine composition for immunization of a subject against a specific pathogen. Plotkin and Mortimer (In ‘Vaccines’, 1994, W.B. Saunders Company; 2nd edition (1994)) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, or parasite). In some embodiments, the target antigen is any pathological target antigen. In some embodiments, an LF polypeptide such as an LFn polypeptide can promote the transmembrane delivery of a not covalently linked target antigen which is a whole virus, or an attenuated virus, where the LF polypeptide functions as an adjuvant to promote delivery to the cytosol of the virus, as well as promoting induction of a CMI response to the whole virus or attenuated virus.

Another aspect of the present invention relates to a vaccine composition comprising an LF polypeptide, such as LFn, and a non-covalently linked target antigen, where the LF polypeptide promotes the transmembrane delivery of the non-covalently linked target antigen such as a whole virus or an attenuated virus, to the cytosol of an intact cell. Another aspect of the present invention related to a method of raising a CMI response to a target polypeptide, where the method comprises administering to a mammal an LF polypeptide such as LFn and a non-covalently linked target antigen, where the LF polypeptide promotes transmembrane delivery of the non-covalently linked target antigen, such as a whole virus or an attenuated virus, to the cytosol of an intact cell.

Another aspect of the present invention relates to a vaccine composition comprising an LF polypeptide such as LFn which is expressed and purified from insect cells. Also encompassed is a vaccein composion in which both the LF polypeptide and the target antigen are expressed in insect cells, e.g. using a bacliovirus expression system. In one embodiment, the vaccine composition comprises a plurality of LF polypeptides such as LFn and a plurality of non-covalently linked target antigens that are expressed and purified from insect cells, wherein the target antigen polypeptides are different but all are from a single intracellular pathogen. In one embodiment, the plurality of target antigen polypeptides are all from a single polypeptide from a single intracellular pathogen. In one embodiment, the vaccine composition comprises a plurality of LF polypeptides and a plurality of non-covalently linked target antigens. In some embodiments, an LF polypeptide and plurality of non-covalently linked target antigens are expressed and purified from insect cells, wherein each target antigen polypeptide is different but all are from several intracellular pathogens. For example, a vaccine composition raising a cell-mediated immune (CMI) response to mumps, measles and rubella viruses can have at least three different non-covalently linked target antigens, each specific to mumps, measles and rubella viruses.

In one aspect, described herein is a composition for promoting a cell mediated immune (CMI) response to a target antigen, the composition comprising at least one isolated target antigen and a portion of a Lethal Factor (LF) polypeptide lacking LF enzymatic activity, wherein the portion of an LF polypeptide is not covalently linked to the target antigen, and wherein the composition does not comprise a protective antigen (PA) of an exotoxin bipartite protein.

In one embodiment, the portion of an LF polypeptide comprises at least the 60 carboxy-terminal amino acids of SEQ ID NO: 3, or a conservative substitution variant thereof that promotes a CMI response to the target antigen.

In another embodiment, the portion of an LF polypeptide comprises at least the 80 carboxy-terminal amino acids of SEQ ID NO: 3, or a conservative substitution variant thereof that promotes a CMI response to the target antigen.

In another embodiment, the portion of an LF polypeptide comprises at least the 104 carboxy-terminal amino acids of SEQ ID NO: 3, or a conservative substitution variant thereof that promotes a CMI response to the target antigen.

In another embodiment, the portion of an LF polypeptide comprises the amino acid sequence corresponding to SEQ ID NO: 3 or a conservative substitution variant thereof that promotes a CMI response to the target antigen.

In another embodiment, the portion of an LF polypeptide does not bind PA polypeptide.

In another embodiment, the portion of an LF polypeptide substantially lacks amino acids 1-33 of SEQ ID NO: 3.

In another embodiment, the portion of an LF polypeptide consists of SEQ ID NO: 4, or a conservative substitution variant thereof that promotes a CMI response to the target antigen.

In another embodiment, the portion of an LF polypeptide consists of SEQ ID NO: 5.

In another embodiment, the cell is in vivo or present in an organism.

In another embodiment, the cell is in vitro.

In another embodiment, the composition induces a response by a cell against a target antigen, when said cell is contacted with the composition in the presence of the target antigen, and in the absence of an exotoxin protective antigen (PA).

In another embodiment, the target antigen is selected from the group consisting of pathogen antigen, a tumor antigen or a endogenous misfolded protein. In another embodiment, the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

In another embodiment, the pathogen antigen is not an antigen expressed by *B. anthracis.*

In another embodiment, the composition optionally comprises at least one adjuvant. In another embodiment, the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol (PEG), poly(alkylenes oxides), monomethoxy-polyethylene glycol polypropylene glycol, block copolymers of polyethylene glycol, polypropylene glycol.

In another aspect, described herein is a method of promotiong a cell-mediated immune response to a cell, the method comprising contacting said cell with a target antigen in the presence of a portion of a *B. anthracis* LF polypeptide lacking LF enzymatic activity, wherein the portion of a *B. anthracis* LF polypeptide lacking LF enzymatic activity is not covalently linked to the target antigen, and wherein said cell is not contacted with a protective antigen (PA) of an exotoxin bipartite protein, whereby a cell-mediated immune response to the target antigen is promoted.

In another aspect, described herein is a composition for delivering a target antigen to a cell, the composition comprising at least one target antigen and a portion of a *B. anthracis* LF polypeptide lacking LF enzymatic activity, wherein the portion of a *B. anthracis* LF polypeptide is not covalently linked to the target antigen, and wherein the composition does not comprise a protective antigen of *B. anthracis* exotoxin bipartite protein.

In one embodiment, the portion of a *B. anthracis* LF polypeptide comprises at least the 60 carboxy-terminal amino acids of SEQ ID NO: 3, or a conservative substitution variant thereof that promotes transmembrane delivery.

In another embodiment, the portion of a *B. anthracis* LF polypeptide comprises at least the 80 carboxy-terminal amino acids of SEQ ID NO: 3, or a conservative substitution variant thereof that promotes transmembrane delivery.

In another embodiment, the portion of a *B. anthracis* LF polypeptide comprises at least the 104 carboxy-terminal amino acids of SEQ ID NO: 3, or a conservative substitution variant thereof that promotes transmembrane delivery.

In another embodiment, the portion of a *B. anthracis* LF polypeptide comprises the amino acid sequence corresponding to SEQ ID NO: 3 or a conservative substitution variant thereof that promotes transmembrane delivery.

In another embodiment, the portion of a *B. anthracis* LF polypeptide does not bind *B. anthracis* PA polypeptide.

In another embodiment, the portion of a *B. anthracis* LF polypeptide substantially lacks amino acids 1-33 of SEQ ID NO: 3.

In another embodiment, the portion of a *B. anthracis* LF polypeptide consists of SEQ ID NO: 4, or a conservative substitution variant thereof that promotes transmembrane delivery.

In another embodiment, the portion of a *B. anthracis* LF polypeptide consists of SEQ ID NO: 5.

In another embodiment, the cell is in vivo or present in an organism.

In another embodiment, the cell is in vitro.

In another embodiment, the composition induces a response by a cell against a target antigen, when said cell is contacted with the composition in the presence of the target antigen, and in the absence of an exotoxin protective antigen (PA).

In another embodiment, the target antigen is selected from the group consisting of pathogen antigen, a tumor antigen or a endogenous misfolded protein.

In another embodiment, the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

In another embodiment, the pathogen antigen is not an antigen expressed by *B. anthracis*.

In another embodiment, the composition optionally comprises at least one adjuvant. In another embodiment, the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol (PEG), poly(alkylenes oxides), monomethoxy-polyethylene glycol polypropylene glycol, block copolymers of polyethylene glycol, polypropylene glycol.

In another aspect, described hedrein is a method of delivering a target antigen to the cytosol of a cell, the method comprising contacting said cell with a target antigen in the presence of a portion of a *B. anthracis* LF polypeptide lacking LF enzymatic activity, wherein the portion of a *B. anthracis* LF polypeptide lacking LF enzymatic activity is not covalently linked to the target antigen, and wherein said cell is not contacted with a protective antigen (PA) of an exotoxin bipartite protein, whereby the target antigen is delivered to the cytosol of the cell.

In one embodiment, the delivery of said target antigen induces a cell-mediated immune (CMI) response to said target antigen by said cell.

In another embodiment, the portion of an LF polypeptide corresponds to SEQ ID NO: 5 or a functional fragment thereof.

In another embodiment, the portion of a *B. anthracis* LF polypeptide comprises at least the 60 carboxy-terminal amino acids of SEQ ID NO: 3, or a conservative substitution variant thereof that promotes transmembrane delivery.

In another embodiment, the portion of a *B. anthracis* LF polypeptide comprises at least the 80 carboxy-terminal amino acids of SEQ ID NO: 3, or a conservative substitution variant thereof that promotes transmembrane delivery.

In another embodiment, the portion of a *B. anthracis* LF polypeptide comprises at least the 104 carboxy-terminal amino acids of SEQ ID NO: 3, or a conservative substitution variant thereof that promotes transmembrane delivery.

In another embodiment, the portion of a *B. anthracis* LF polypeptide comprises the amino acid sequence corresponding to SEQ ID NO: 3 or a conservative substitution variant thereof that promotes transmembrane delivery.

In another embodiment, the portion of a *B. anthracis* LF polypeptide does not bind *B. anthracis* PA polypeptide.

In another embodiment, the portion of a *B. anthracis* LF polypeptide substantially lacks amino acids 1-33 of SEQ ID NO: 3.

In another embodiment, the portion of a *B. anthracis* LF polypeptide consists of SEQ ID NO: 4, or a conservative substitution variant thereof that promotes transmembrane delivery.

In another embodiment, the portion of a *B. anthracis* LF polypeptide consists of SEQ ID NO: 5.

In another embodiment, the cell is in vivo or present in an organism.

In another embodiment, the cell is in vitro.

In another embodiment, the method further comprises administering to the cell at least one other adjuvant, wherein the adjuvant does not comprise SEQ ID NO: 3 or SEQ ID NO: 4. In another embodiment, the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.

In another embodiment, the target antigen is selected from the group consisting of pathogen antigen, a tumor antigen or a endogenous misfolded protein.

In another embodiment, the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

In another embodiment, the pathogen antigen is not an antigen expressed by B. anthracis.

In another aspect, described herein is the use of a composition as described herein to induce a cell mediated response against a target antigen by a cell, wherein the cell is contacted with the composition in the presence of the target antigen, and in the absence of an exotoxin protective antigen (PA). The composition can be, for example, a composition comprising at least one isolated target antigen and a portion of a Lethal Factor (LF) polypeptide lacking LF enzymatic activity, wherein the portion of an LF polypeptide is not covalently linked to the target antigen, and wherein the composition does not comprise a protective antigen (PA) of an exotoxin bipartite protein In one embodiment, composition further comprises at least one additional immune adjuvant. In another embodiment, the immune adjuvant is selected from the group consisting of; Alum, Complete Freud's Adjuvant, Incomplete Freud's Adjuvant, CM-CSF, QS21, CpG, RIBI Detox.

In another embodiment, the immune adjuvant is a cytokine selected from the group consisting of; IL-2, Ig-IL-2.

In another embodiment, the immune adjuvant is a co-stimulatory molecule selected from the group consisting of; B7, ICAM, LFS.

In another embodiment, the immune adjuvant is a non-antigenic polymeric substance selected from the group consisting of; dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.

In another aspect, the method of any of the above uses an LF polypeptide of SEQ ID NO: 3 or SEQ ID NO: 4 that is codon optimized for production in bacterial cells.

BRIEF DESCRIPTION OF THE DRAWINGS

FIGS. 2A-E show the amino acid sequence of various Lethal Factor (LF) polypeptides (SEQ ID NO:1). FIG. 2A shows the full length amino acid sequence of LF. FIG. 2B shows the amino acid sequence of the first 288 amino acids of LFn (SEQ ID NO:2). FIG. 2C shows the sequence of amino acids 185-288 of Lethal Factor, sometimes referred to as Fragment 3 (SEQ ID NO:3). FIG. 2D shows the amino acid sequence of LFn lacking the amino-terminal signal peptide (SEQ ID NO: 4). FIG. 2E shows the amino acid sequence of one example of a functional fragment of LFn that transports or increases transport of an antigen across a target cell membrane. The fragment is a C-terminal fragment (SEQ ID NO: 5).

DETAILED DESCRIPTION OF THE INVENTION

Figure 1:
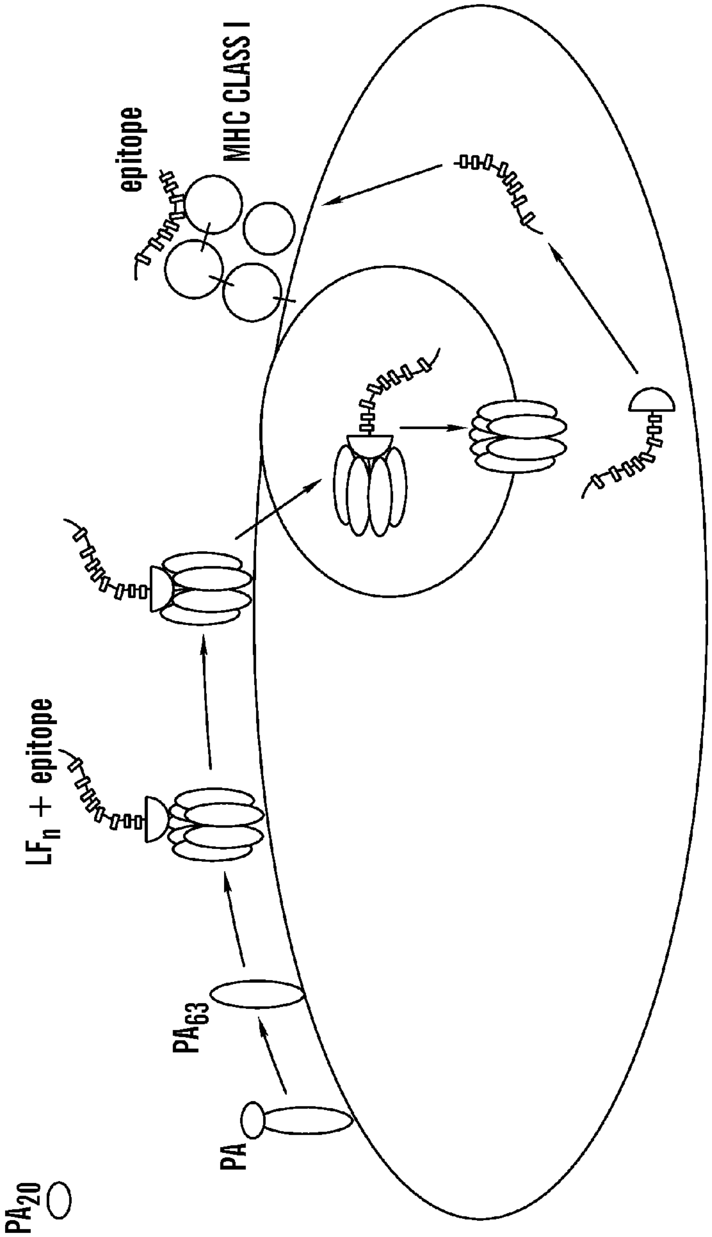
FIG. 1 is a drawing depicting the PA-mediated entry of LFn into a cell via endocytosis, and subsequent presentation by MHC Class I molecules.

One aspect of the present invention provides compositions for delivering a target antigen to the cytosol of a cell and uses thereof. In particular, one aspect relates to a composition comprising an LF polypeptide and a target antigen, and methods of use of using such compositions to direct an immune response against an antigen, where the composition comprises an LF polypeptide and a non-linked or non-covalently linked antigen. The LF polypeptide or a fragment thereof function to enhance the efficacy of an antigen to direct an immune response to the target antigen. In particular, the compositions of the present invention comprise at least one LF polypeptide, for example, the N-terminal Lethal Factor (LFn) of a bipartite exotoxin such as *B. anthracis*, or a fragment or variant thereof, and at least one non-linked or non-covalently linked target antigen.

Accordingly, one aspect of the present invention relates to a composition consisting essentially of LF polypeptide, for example, the N-terminal Lethal Factor (LFn) of a bipartate exotoxin such as *B. anthracis*, where the LFn is not covalently linked to the target antigen and the composition does not comprise a protective antigen (PA) of *B. anthracis*.

One aspect of the present invention provides a means for eliciting a specific immune response, in particular a CMI response to a target antigen, whereby the target antigen is delivered to the cytosol of a cell by a composition consisting essentially of an LF polypeptide, such as for example, the N-terminal Lethal Factor (LFn) polypeptide or a fragment or variant thereof, and a target antigen that is not covalently linked to the LF polypeptide.

In some embodiments of this aspect, the composition comprises an LF polypeptide such as LFn and a non-linked or non-covalently linked target antigen, meaning that the LF polypeptide such as LFn is not linked to the target antigen by any covalent bond. In one aspect, the LF polypeptide is not physically associated with the target antigen in the subject composition, or, alternatively, not substantially physically linked to the target antigen polypeptide. In alternative embodiments, an LF polypeptide can be in a non-covalently linked complex with a target antigen. For example and as discussed in more detail herein below, in some embodiments, a composition can form an LFn:target antigen complex. In some embodiments, the composition comprises an LFn:target antigen complex, where an LFn polypeptide, or fragment thereof is associated with the target antigen by non-covalent interactions, for example van der Waals forces or other interactions, such as electrostatic interactions, hydrophilic interactions, hydrophobic interactions and any non-covalent bond association known by a skilled artisan.

In another embodiment the composition comprises an LFn:target antigen complex, where an LF polypeptide such as LFn and a non-covalently linked target antigen are in a complex with at least one additional moiety, for example, a linked polypeptide, where both the target antigen and the LF polypeptide interacts with the additional moiety. Such interactions can be any non-covalent bond association known by a skilled artisan, including but not limited to, van der Waals forces, hydrophilic interactions, hydrophobic interactions and other non-covalent interactions.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which the invention belongs.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

As used herein, the term "fusion polypeptide" means a protein created by joining two polypeptide coding sequences together. A fusion polypeptide can be formed by joining a coding sequence of one polypeptide with a coding sequence of a second polypeptide to form a fusion coding sequence. The fusion coding sequence, when transcribed and translated, expresses a fusion polypeptide.

As used herein, the term "promotes transmembrane delivery" refers to the ability of a first polypeptide to facilitate a second polypeptide to traverse the membrane of an intact, living cell. As used in the compositions and methods described herein, the second protein (i.e. target antigen) is either not linked or is non-covalently linked to the first polypeptide (i.e. an LF polypeptide).

As used herein, the term "cytosol" refers to the interior of an intact cell. The "cytosol" comprises the cytoplasm and the organelles inside a cell.

As used herein, the term " an intact cell " refers to a living cell with an unbroken, uncompromised plasma membrane, and that has a differential membrane potential across the membrane, with the inside of the cell being negative with respect to the outside of the cell.

The term "adjuvant" as used herein refers to any agent or entity which increases the antigenic response by a cell or a subject to a target antigen.

As used herein, the term "substantially lacks amino acids 1-33" in the context of an LF polypeptide described herein refers to an LF polypeptide that lacks signal peptide activity.

As used herein, the term "intracellular pathogen" refers to a pathogen or components thereof that can reside inside an intact cell.

As used herein, the term "pathogen" refers to an organism or molecule that causes a disease or disorder in a subject. For example, pathogens include but are not limited to viruses, fungi, bacteria, parasites and other infectious organisms or molecules therefrom, as well as taxonomically related macroscopic organisms within the categories algae, fungi, yeast and protozoa or the like.

As used herein, the term "prokaryotic pathogen" refers to a bacterial pathogen.

As used herein, the term "viral pathogen" refers to a virus that causes illness or disease, such as HIV.

As used herein, the term "parasitic pathogen" refers to a microorganism that is parasitic, residing for an extended period inside a host cell or host organism, that gains benefits from the host and at the same time causes illness or disease. A parasitic pathogen can be bacteria, viruses, fungi, and protists.

An "antigen presenting cell" is a cell that expresses the Major histocompatibility complex (MHC) molecules and can display foreign antigen complexed with MHC on its surface. Examples of antigen displaying cells are dendritic cells, macrophages, B cells, fibroblasts (skin), thymic epithelial cells, thyroid epithelial cells, glial cells (brain), pancreatic beta cells, and vascular endothelial cells.

The terms "protective antigen" or "PA" are used interchangeably herein to refer to part of the B. anthracis exotoxin bipartite protein which binds to a mammalian cell's surface by cellular receptors. A "PA," as the term is used has its receptor binding site intact and functional. U.S. Pat. Nos. 5,591,631 and 5,677,274 (incorporated by reference in their entirety) describe PA fusion proteins that target PA to particular cells, such as cancer cells and HIV-infected cells, using as fusion partners ligands for receptors on the targeted cells.

The term "lethal factor" or "LF" as used herein refers generally to a non-PA polypeptide of the bipartite *B. anthracis* exotoxin. Wild-type, intact *B. anthracis* LF polypeptide has the amino acid sequence set out in GenBank Accession Number M29081 (Gene ID No: 143143), which corresponds to SEQ ID NO: 1. SEQ ID NO: 1 corresponds to LF with a signal peptide located at residues 1 to 33 at its N-terminus. Stated another way, immature wild-type LF corresponds to an 809 amino acid protein, which includes a 33 amino acid signal peptide at the N-terminus. The amino acid sequence of immature wild-type LF (SEQ ID NO: 1) with the signal peptide highlighted in bold is as follows:

(SEQ ID NO: 1)

MNIKKEFIKVISMSCLVTAITLSGPVFIPLVQGAGGHGDVGMHVKEKEKNKDENKRKDEERNKTQEE

HLKEIMKHIVKIEVKGEEAVKKEAAEKLLEKVPSDVLEMYKAIGGKIYIVDGDITKHISLEALSEDKKKIK

DIYGKDALLHEHYVYAKEGYEPVLVIQSSEDYVENTEKALNVYYEIGKILSRDILSKINQPYQKFLDVLN

TIKNASDSDGQDLLFTNQLKEHPTDFSVEFLEQNSNEVQEVFAKAFAYYIEPQHRDVLQLYAPEAFNYM

DKFNEQEINLSLEELKDQRMLSRYEKWEKIKQHYQHWSDSLSEEGRGLLKKLQIPIEPKKDDIIHSLSQEE

KELLKRIQIDSSDFLSTEEKEFLKKLQIDIRDSLSEEEKELLNRIQVDSSNPLSEKEKEFLKKLKLDIQPYDI

NQRLQDTGGLIDSPSINLDVRKQYKRDIQNIDALLHQSIGSTLYNKIYLYENMNINNLTATLGADLVDST

DNTKINRGIFNEFKKNFKYSISSNYMIVDINERPALDNERLKWRIQLSPDTRAGYLENGKLILQRNIGLEIK

DVQIIKQSEKEYIRIDAKVVPKSKIDTKIQEAQLNINQEWNKALGLPKYTKLITFNVHNRYASNIVESAYLI

LNEWKNNIQSDLIKKVTNYLVDGNGRFVFTDITLPNIAEQYTHQDEIYEQVHSKGLYVPESRSILLHGPSK

GVELRNDSEGFIHEFGHAVDDYAGYLLDKNQSDLVTNSKKFIDIFKEEGSNLTSYGRTNEAEFFAEAFRL

MHSTDHAERLKVQKNAPKTFQFINDQIKFIINS

Cleavage of the immature LF protein results in a mature wild-type LF polypeptide of 776 amino acids in length. The 776 amino acid polypeptide sequence of mature wild-type LF polypeptide (i.e. lacking the N-terminal signal peptide) corresponds to SEQ ID NO: 2, as follows:

(SEQ ID NO: 2)

AGGHGDVGMHVKEKEKNKDENKRKDEERNKTQEEHLKEIMKHIVKIEVKGEEAVKKEAAEKLLEKVP

SDVLEMYKAIGGKIYIVDGDITKHISLEALSEDKKKIKDIYGKDALLHEHYVYAKEGYEPVLVIQSSEDY

-continued

```
VENTEKALNVYYEIGKILSRDILSKINQPYQKFLDVLNTIKNASDSDGQDLLFTNQLKEHPTDFSVEFLEQ

NSNEVQEVFAKAFAYYIEPQHRDVLQLYAPEAFNYMDKFNEQEINLSLEELKDQRMLSRYEKWEKIKQ

HYQHWSDSLSEEGRGLLKKLQIPIEPKKDDIIHSLSQEEKELLKRIQIDSSDFLSTEEKEFLKKLQIDIRDSL

SEEEKELLNRIQVDSSNPLSEKEKEFLKKLKLDIQPYDINQRLQDTGGLIDSPSINLDVRKQYKRDIQNIDA

LLHQSIGSTLYNKIYLYENMNINNLTATLGADLVDSTDNTKINRGIFNEFKKNFKYSISSNYMIVDINERP

ALDNERLKWRIQLSPDTRAGYLENGKLILQRNIGLEIKDVQIIKQSEKEYIRIDAKVVPKSKIDTKIQEAQL

NINQEWNKALGLPKYTKLITFNVHNRYASNIVESAYLILNEWKNNIQSDLIKKVTNYLVDGNGRFVFTDI

TLPNIAEQYTHQDEIYEQVHSKGLYVPESRSILLHGPSKGVELRNDSEGFIHEFGHAVDDYAGYLLDKNQ

SDLVTNSKKFIDIFKEEGSNLTSYGRTNEAEFFAEAFRLMHSTDHAERLKVQKNAPKTFQFINDQIKFIINS
```

The term "LF polypeptide" applies not only to full length, wild-type LF (with or without the signal sequence), but also to fragments thereof that mediate intracellular delivery of non-covalently linked polypeptides to a cell. Also included in the term "LF polypeptide" are conservative substitution variants of LF, including conservative substitution variants that mediate such intracellular delivery.

The term "substitution" when referring to a peptide, refers to a change in an amino acid for a different amino-acid moiety. Substitutions can be conservative or non-conservative substitutions, as described further herein below.

The term "LFn polypeptide" refers to an N-terminal fragment of *B. anthracis* LF that does not display zinc metalloproteinase activity, mitogen-activated kinase activity, or both, yet does mediate intracellular or transmembrane delivery of non-covalently linked polypeptides. Thus, LFn polypeptides are a subset of LF polypeptides. Each method and/or kit described herein is contemplated to use one or more LF polypeptides, and not linked or non-covalently linked target antigen. LFn polypeptides as defined and described herein are preferred. In one aspect, "LFn polypeptide" includes SEQ ID NO: 3, which corresponds to a 288 amino acid immature LFn protein; this LFn protein is "immature" in that it includes a signal peptide located at residues 1 to 33 of the N-terminus. Stated another way, immature LFn corresponds to a 288 amino acid protein, which includes a 33 amino acid signal peptide at the N-terminus. Signal peptide cleavage of the immature LFn protein of SEQ ID NO: 3 results in a mature LFn polypeptide of 255 amino acids in length. It should be emphasized that, for the purposes of the methods and compositions described herein, the LF and/or LFn polypeptides can either include or lack the signal peptide—that is, the presence or absence of the signal peptide is not expected to influence the activity of LF polypeptides as transmembrane transport facilitators in the methods described herein. The amino acid sequence of immature LFn (SEQ ID NO: 3) with the signal peptide highlighted in bold is as follows:

(SEQ ID NO: 3)

MNIKKEFIKVISMSCLVTAITLSGPVFIPLVQGAGGHGDVGMHVKEKEKNKDENKRKDEERNKTQEE

HLKEIMKHIVKIEVKGEEAVKKEAAEKLLEKVPSDVLEMYKAIGGKIYIVDGDITKHISLEALSEDKKKIK

DIYGKDALLHEHYVYAKEGYEPVLVIQSSEDYVENTEKALNVYYEIGKILSRDILSKINQPYQKFLDVLN

TIKNASDSDGQDLLFTNQLKEHPTDFSVEFLEQNSNEVQEVFAKAFAYYIEPQHRDVLQLYAPEAFNYM

DKFNEQEINLS

The polypeptide sequence of a mature LFn polypeptide (which lacks the N-terminal signal peptide) is 255 amino acids in length and corresponds to SEQ ID NO: 4 is as follows:

```
                                                          (SEQ ID NO: 4)
AGGHGDVGMHVKEKEKNKDENKRKDEERNKTQEEHLKEIMKHIVKIEVKGEEAVKKEAAEKLLEKVP

SDVLEMYKAIGGKIYIVDGDITKHISLEALSEDKKKIKDIYGKDALLHEHYVYAKEGYEPVLVIQSSEDY

VENTEKALNVYYEIGKILSRDILSKINQPYQKFLDVLNTIKNASDSDGQDLLFTNQLKEHPTDFSVEFLEQ

NSNEVQEVFAKAFAYYIEPQHRDVLQLYAPEAFNYMDKFNEQEINLS
```

The term "functional fragment" as used in the context of a "functional fragment of LFn" refers to a fragment of an LFn polypeptide that mediates, effects or facilitates transport of an antigen across an intact, alive cell's membrane. One example of such a fragment of an LFn polypeptide is a 104 amino acid C-terminal fragment of LFn corresponding to SEQ ID NO: 5 as follows (this sequence is also disclosed as SEQ ID NO: 3 in U.S. patent application Ser. No. 10/473, 190, which is incorporated herein by reference):

(SEQ ID NO: 5)
GKILSRDILSKINQPYQKFLDVLNTIKNASDSDGQDLLFTNQLKEHPTDFSVEFLEQNSNEVQEVFAKAFA

YYIEPQHRDVLQLYAPEAFNYMDKFNEQEINLS

The term "LFn polypeptide" as used herein encompasses each of the "immature" LFn and "mature" LFn molecules described herein, as well as fragments, variants (including conservative substitution variants) and derivatives thereof that mediate, effect or facilitate transport of a target antigen which is not linked, or non-covalently linked, to the LF polypeptide across the membrane of an intact, living cell. Additional fragments of LFn polypeptides specifically contemplated for use in the methods, compositions and kits described herein include a fragment comprising, or optionally, consisting essentially of the C-terminal 60, 80, 90, 100 or 104 amino acids of SEQ ID NO: 3 or a conservative substitution variant thereof that mediates, effects or facilitates transfer of a not-linked or non-covalently linked target antigen polypeptide across an intact membrane of a living cell, intact cell.

A "fragment" of a target antigen as that term is used herein will be at least 15 amino acids in length, and can be, for example, at least 16, at least 17, at least 18, at least 19, at least 20 or at least 25 amino acids or greater. Thus, in instances where, for example, a panel of target antigen fragment-LF polypeptides are prepared, the target antigen fragments will be at least 15 amino acids in length.

The term "Cytotoxic T Lymphocyte" or "CTL" refers to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of macrophages, natural killer cells (NK), antigen-specific cytotoxic T-lymphocytes (T-cells), and the release of various cytokines in response to a target antigen. Stated another way, CMI refers to immune cells (such as T cells and lymphocytes) which bind to the surface of other cells that display the antigen (such as antigen presenting cells (APS)) and trigger a response. The response can involve either other lymphocytes and/or any of the other white blood cells (leukocytes) and the release of cytokines. Accordingly, cell-mediated immunity (CMI) is an immune response that does not involve antibodies but rather involves the activation of macrophages and NK-cells, the production of antigen-specific cytotoxic T-lymphocytes, and the release of various cytokines in response to an antigen. Cellular immunity protects the body by: (i) activating antigen-specific cytotoxic T-lymphocytes (CTLs) that are able to destroy body cells displaying epitopes of foreign antigen on their surface, such as virus-infected cells, cells with intracellular bacteria, and cancer cells displaying tumor antigens; (2) activating macrophages and NK cells, enabling them to destroy intracellular pathogens; and (3) stimulating cells to secrete a variety of cytokines that influence the function of other cells involved in adaptive immune responses and innate immune responses. Without wishing to be bound by theory and by way of background, the immune system was separated into two branches: humoral immunity, for which the protective function of immunization could be found in the humor (cell-free bodily fluid or serum) and cellular immunity, for which the protective function of immunization was associated with cells.

The term "immune cell" as used herein refers to any cell which can release a cytokine in response to a direct or indirect antigenic stimulation. Included in the term "immune cells" herein are lympocytes, including natural killer (NK) cells, T-cells (CD4+ and/or CD8+ cells), B-cells, macrophages and monocytes, Th cells; Th1 cells; Th2 cells; Tc cells; stromal cells; endothelial cells; leukocytes; dendritic cells; macrophages; mast cells and monocytes and any other cell which is capable of producing a cytokine molecule in response to direct or indirect antigen stimulation. Typically, an immune cell is a lymphocyte, for example a T-cell lymphocyte.

The term "cytokine" as used herein is used interchangeably with the term "effector molecule," and refers to a molecule released from an immune cell in response to stimulation with an antigen. Examples of such cytokines include, but are not limited to; GM-CSF; IL-1α; IL-1β; IL-2; IL-3; IL-4; IL-5; IL-6; IL-7; IL-8; IL-10; IL-12; IFN-α; IFN-β; IFN-γ; MIP-1α; MIP-1β; TGF-β; TNFα and TNFβ.

The term "covalently bonded" is meant joined either directly or indirectly (e.g., through a linker) by a chemical bond. Stated another way, a covalent bond is a bond between two or more atoms that is provided by electrons that travel between the atom's nuclei, holding them together but keeping them a stable distance apart. Covalent bonds share electrons between two or more atoms.

The term "complex" as used herein refers to a collection of two or more molecules, that are physically associated with each other by means other than a covalent interaction; for example they can be connected by electrostatic interactions such as van der Waals forces, etc.

The term "fusion protein" as used herein refers to a recombinant protein of two or more proteins which are joined by a peptide bond. Fusion proteins can be produced, for example, by a nucleic acid sequence encoding one protein joined to the nucleic acid encoding another protein such that they constitute a single open-reading frame that can be translated into a single polypeptide harboring all the intended proteins.

The term "translocated into a cell" refers to the movement of a moiety, such as the target antigen, and optionally LFn, an LFn homologue or mimetic, or variant thereof from a location the outside the cell, across the plasma membrane to the inside the cell.

The term "transduction" refers to any method whereby a nucleic acid is introduced into a cell, e.g., by transfection, lipofection, electroporation, biolistics, passive uptake, lipid: nucleic acid complexes, viral vector transduction, injection, contacting with naked DNA, and the like.

The term "in vivo" refers to assays or processes that occur in an animal.

The term "ex vivo" refers to assays that are performed using a living cell with an intact membrane that is outside of the body, e.g., explants, cultured cells, including primary cells and cell lines, transformed cell lines, and extracted tissue or cells, including blood cells, among others.

The term "in vitro" refers to assays that do not require the presence of a cell with an intact membrane.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene or genes. Transformation/cancer is associated with, e.g., morphological changes, immortalization of cells, aberrant growth control, foci formation, anchorage independence, proliferation, malignancy, contact inhibition and density limitation of growth, growth factor or serum independence, tumor specific markers levels, invasiveness, tumor growth or suppression in suitable animal hosts such as nude mice, and the like, in vitro, in vivo, and ex vivo (see also Freshney, Culture of Animal Cells: A Manual of Basic Technique (3rd ed. 1994)).

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In some embodiments, a mammal is a human. In alternative embodiments, a mammal is not a human.

The term "subject" as used herein refers to any animal in which it is useful to deliver an exogenous protein to the cytosol of a cell, or to diagnose a CMI response, for example to diagnose if the subject has a disease or condition, or is likely to develop a disease or condition. The subject can be a mammal, for example a human, or can be a wild, domestic, commercial or companion animal. While in one embodiment it is contemplated that CMI assays are suitable for diagnostic use in humans, it is also applicable to all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is a wild animal, for example a bird such as for the diagnosis of avian flu. In some embodiments, the subject is an experimental animal or animal substitute as a disease model. The subject can be a subject in need of veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates, or livestock animals such as pigs, cattle and sheep, where the detection of a CMI response to a pathogen is useful to prevent a disease and/or to control the spread of a disease, for example SIV, STL1, SFV, or in the case of live-stock, hoof and mouth disease and other such diseases. In some embodiments, a subject is not a human subject.

The term "biological sample" refers to a sample of biological tissue, cells, or fluid that, in a healthy and/or pathological state, contains immune cells as they are described herein and cells capable of processing and displaying an intracellular polypeptide antigen. Such samples include, but are not limited to, whole blood, cultured cells, primary cell preparations, sputum, amniotic fluid, tissue or fine needle biopsy samples, peritoneal fluid, and pleural fluid, among others. In some embodiments a biological sample is taken from a human patient, and in alternative embodiments the biological sample is taken from any mammal, such as rodents, animal models of diseases, commercial animals, companion animals, dogs, cats, sheep, cattle, and pigs, etc. The biological sample can be pretreated as necessary for storage or preservation, by dilution in an appropriate buffer solution or concentrated, if desired. However, the sample must contain living cells. Any of a number of standard aqueous buffer solutions, employing one of a variety of buffers, such as phosphate, Tris, or the like, at physiological pH can be used. The biological sample can in certain circumstances be stored prior to use in assays as disclosed herein. Such storage can be at +4C or frozen, for example at −20C or -80C, provided suitable cryopreservation agents are used to maintain cell viability once the cells are thawed.

The term "tissue" refers to a group or layer of similarly specialized cells, which together perform certain special functions. The term "tissue-specific" refers to a source of cells from a specific tissue. The term "tissue" is intended to include, blood, blood preparations such as plasma and serum, bones, joints, muscles, smooth muscles, and organs.

The term "wild type" refers to the naturally-occurring, normal polynucleotide sequence encoding a protein, or a portion thereof, or protein sequence, or portion thereof, respectively, as it normally exists in vivo. Accordingly, as disclosed herein, the wild type amino acid sequence for LFn protein corresponds to SEQ ID NO: 3 (with signal peptide) and/or SEQ ID NO: 4 (without signal peptide), which correspond to an N-terminal fragment of the Lethal Factor (LF) from *B. anthracis.*

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The terms "polypeptide" and "protein" are used interchangeably to refer to a polymer of amino acid residues linked by peptide bonds, and for the purposes of the claimed invention, have a minimum length of at least 15 amino acids. Oligopeptides, oligomer multimers, and the like, typically refer to longer chains of amino acids and are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. For the methods, kits and compositions described herein, the term "peptide" refers to a sequence of peptide-linked amino acids containing at least two and less than 15 amino acids in length.

It will be appreciated that a protein or polypeptide often contains amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides as described herein include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectively. A sequence which is "unrelated" or "non-homologous" shares less than 40% identity, though preferably less than 25% identity with the sequences as disclosed herein.

The term "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 60% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 60 at least 70%, at least 80%, at least 90%, at least 95% identical, at least 97% identical, or at least 99% identical. Determination of homologs of the genes or peptides of the present invention can be easily ascertained by the skilled artisan.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Where necessary or desired, optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G, U or I) or amino acid residue occurs in both sequences to yield the number of matched positions, dividing the number of matched positions by the total number of positions in the comparison window (i.e., the window size), and multiplying the result by 100 to yield the percentage of sequence identity.

The term "variant" as used herein refers to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild- type polynucleotide or polypeptide). A "variant" of an LFn polypeptide refers to a molecule substantially similar in structure and function to that of a polypeptide of SEQ ID NO: 3, where the function is the ability to mediate, effect or facilitate transport of a non linked or non-covalently linked polypeptide across a cell membrane of a living cell or a living cell present in a subject. In some embodiments, a variant of SEQ ID NO: 3 or SEQ ID NO: 4 is a fragment of SEQ ID NO: 3 or 4 as disclosed herein, such as SEQ ID NO: 5.

A molecule is said to be "substantially similar" to another molecule if both molecules have substantially similar structures (i.e., they are at least 50% similar in amino acid sequence as determined by BLASTp alignment set at default parameters) and are substantially similar in at least one relevant function (here, for example, at least 50% as active in mediating, effecting or facilitating transport of a non-covalently linked polypeptide across the membrane of an intact, living cell). Measurement of transmembrane transp; ort can be made, for example, as described by Kushner et al., 2003, Proc. Natl. Acad. Sci. USA, 100(11): 6652-6657, which is incorporated herein by reference.

The term "substantially similar," when used in reference to a variant of an LF polypeptode, e.g., LFn, or a functional derivative of LFn as compared to the LFn protein encoded by SEQ ID NO: 3 means that a particular subject sequence, for example, an LFn fragment or LFn variant or LFn derivative sequence, varies from the sequence of the LFn polypeptide encoded by SEQ ID NO: 3 by one or more substitutions, deletions, or additions relative to SEQ ID NO: 3, but retains at least 50% of the transmembrane transport facilitation activity, and preferably higher, e.g., at least 60%, 70%, 80%, 90% or more exhibited by the LFn protein of SEQ ID NO: 3. (It is acknowledged that LFn does not occur naturally—reference to a "native" or "natural" LFn sequence is intended to convey that the sequence is identical to the portion of naturally-occurring LF polypeptide designated as LFn herein.) In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given LFn nucleic acid sequence if: (a) the nucleotide sequence specifically hybridizes to the coding regions of the native LFn sequence, or (b) the nucleotide sequence is capable of hybridization to nucleotide sequence of LFn encoded by SEQ ID NO: 1 under moderately stringent conditions and has biological activity similar to the native LFn protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another having similar structural and/or chemical properties. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).)

The choice of conservative amino acids can be selected based on the location of the amino acid to be substituted in the polypeptide, for example if the amino acid is on the exterior of the polypeptide and exposed to solvents, or on the interior and not exposed to solvents. Selection of such conservative amino acid substitutions is within the skill of one of ordinary skill in the art and is described, for example by Dordo et al., J. Mol Biol, 1999, 217, 721-739 and Taylor et al., J. Theor. Biol. 119(1986);205-218 and S. French and B. Robson, J. Mol. Evol. 19(1983)171. Accordingly, one can select conservative amino acid substitutions suitable for amino acids on the exterior of a protein or polypeptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions suitable for amino acids on the interior of a protein or polypeptide. For example, one can use suitable conservative substitutions for amino acids in the interior of a protein or polypeptide (i.e. the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." A variant of an LFn polypeptide, for example a variant of SEQ ID NO: 3 or 4 is meant to refer to any molecule substantially similar in structure (i.e., having at least 50% homology as determined by BLASTp analysis using default parameters) and function (i.e., at least 50% as effective as a polypeptide of SEQ ID NO: 3 in transmembrane transport) to a molecule of SEQ ID NO: 3 or 4.

As used herein, the term "non-conservative" refers to substituting an amino acid residue for a different amino acid residue that has substantially different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to a protein molecule which possess a biological activity that is substantially similar to a biological activity of the entity or molecule of which it is a derivative or variant. By "substantially similar" in this context is meant that the biological activity, e.g., transmembrane transport of associated polypeptides is at least 50% as active as a reference, e.g., a corresponding wild-type polypeptide, and preferably at least 60% as active, 70% as active, 80% as active, 90% as active, 95% as active, 100% as active or even higher (i.e., the variant or derivative has greater activity than the wild-type), e.g., 110% as active, 120% as active, or more.

"Insertions" or "deletions," as the terms are used herein, are typically in the range of about 1 to 5 amino acids. Where necessary, the variation permitted in view of maintaining function can be experimentally determined by producing the polypeptide synthetically while systematically making insertions, deletions, or substitutions of nucleotides in the sequence using recombinant DNA techniques.

The term "specifically binds" refers to binding with a Kd of 10 micromolar or less, preferably 1 micromolar or less, more preferably 100 nM or less, 10 nM or less, or 1 nM or less.

By "substantially pure" is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally occurring organic molecules with which it is naturally associated. A substantially pure polypeptide can be obtained, for example, by extraction from a natural source, by expression of a recombinant nucleic acid in a cell that does not normally express that protein, or by chemical synthesis.

The terms "reduced" or "reduce" or "decrease" as used herein generally mean a decrease by a statistically significant amount relative to a reference. However, for avoidance of doubt, "reduced" or "decreased" mean a statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e. absent level as compared to a reference sample), or any decrease between 10-100% as compared to a reference level, for example a control sample, such as a negative control which has a absence of an agent or absence of a condition (such as absence of a LF polypeptide).

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e. absent level as compared to a reference sample), where the reference level can be a control sample, such as a negative control sample, such as a sample in the absence of an agent or absence of a condition (such as absence of a LF polypeptide).

The terms "increased" or "increase" as used herein generally mean an increase by a statically significant amount; for the avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, such as a control condition, such as a negative control or in the absence of a condition (such as absence of an LF polypeptide).

The term "high" as used herein generally means a higher by a statically significant amount relative to a reference; for the avoidance of doubt, "high" means a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, at least 2-fold higher, at least 3-fold higher, at least 4-fold higher, at least 5-fold higher, at least 10-fold higher or more, as compared to a reference level, such as a control condition, such as a negative control or in the absence of a condition (such as absence of an LF polypeptide).

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of heterologous nucleic acid to which it has been linked; a plasmid is a species of the genus encompassed by the term "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors that can be used in the methods as disclosed herein include, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

As used herein, the terms "treat" or "treatment" or "treating" refer to both therapeutic treatment and prophylactic or preventative measures, wherein the object is to prevent or slow the development of the disease. Without wishing to be limited by examples, if the disease is cancer, the slowing of the development of a tumor, the spread of cancer, or reducing at least one effect or symptom of a condition, disease or disorder associated with inappropriate proliferation or a cell mass, for example cancer would be considered a treatment. Where the disease is, for example, an infection, such as an HIV infection, a decrease of virus titer, or increase in white blood cells, or an improvement, or attenuating the decline in a symptom of Auto-Immune Disease syndrome (AIDS) is considered treatment. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The term "effective amount" as used herein refers to the amount of therapeutic agent or pharmaceutical composition to alleviate at least one or more symptom of a targeted disease or disorder, and relates to a sufficient amount of pharmacological composition to provide the desired effect. Alternatively, the term refers to the amount necessary to deliver an exogenous protein or polypeptide to the cytosol of a cell. The phrase "therapeutically effective amount" as used herein, e.g., of any composition as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with a disease.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, up to and including at least about 100% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not reasonable to specify the exact "effective amount". However, for any given case, an appropriate "effective amount" can be determined by one of ordinary skill in the art using only routine experimentation. The efficacy of treatment can be judged by an ordinarily skilled practitioner. For example, efficacy can be assessed in animal models of cancer and tumor, for example treatment of a rodent having an experimental cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., mice or rats, or for example, transplantation of tumor cells, e.g. xenograft animal cancer models, or an animal model which has been genetically modified to develop cancer. Further, in some embodiments an experimental model could be an in vitro model, such as organ culture, cells or cell lines. When using an experimental animal model, efficacy of treatment is evidenced when a reduction in a symptom of the cancer, for example a reduction in the size of the tumor or when a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the terms "administering," and "introducing" are used interchangeably and refer to the placement of agents as disclosed herein into a subject by a method or route which results in delivering of such agent(s) at a desired site. The compounds can be administered by any appropriate route which results in an effective treatment in the subject.

The terms "composition" or "pharmaceutical composition" used interchangeably herein refer to compositions or formulations that comprise an LF polypeptide and at least one target antigen that is not covalently linked to the LF polypeptide. In some embodiments, a pharmaceutical composition can also optionally comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity or solubility of, or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery compositions can be formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition comprises an LF polypeptide and at least one target antigen that is not covalently bound to the LF polypeptide, and in some embodiments, in combination with one or more pharmaceutically acceptable ingredients. The carrier can be in the form of a solid, semi-solid or liquid diluent, cream or a capsule.

As used herein, the term "an intact cell" refers to a living cell with an unbroken, uncompromised plasma membrane, which cell has a differential membrane potential across the membrane, with the inside of the cell being negative with respect to the outside of the cell.

As used herein, the term "N-glycosylated" or "N-glycosylation" refers to the covalent attachment of a sugar moiety to asparagine residues in a polypeptide. Sugar moieties can include but are not limited to glucose, mannose, and N-acetylglucosamine. Modifications of the glycans are also included, e.g., siaylation. The LFn polypeptide has three N-glycosylation sites: asparagine positions 62, 212, and 286 in the 809 amino acid polypeptide.

As used herein, the terms "N-glycosylated LFn-fusion polypeptide," "N-glycosylated LF-fusion polypeptide" or "N-glycosylated fused polypeptide" refer to a fusion polypeptide, as defined herein, that has at least one sugar moiety covalently attached to an asparagine residue. For example, Asn-62, Asn-212, and Asn-286 can be glycosylated in an N-glycosylated LF-fusion polypeptide.

The articles "a" and "an" are used herein to refer to one or to more than one (i.e., to at least one) of the grammatical object of the article. By way of example, "an element" means one element or more than one element.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment. Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Methods and Compositions Involving Lfn Adjuvant

The various components required to perform the methods described herein and considerations for various aspects of the methods and compositions are described in the following sections.

I. LF Polypeptides

By way of background and without wishing to be limited by theory, *B. anthracis* is the causative agent of anthrax in animals and humans. The toxin produced by *B. anthracis* consists of two bipartite protein exotoxins, lethal toxin (LT) and edema toxin. LT is composed of protective antigen (PA) and lethal factor (LF), whereas edema toxin consists of PA and edema factor (EF). None of these three components, PA, LF, and EF, alone is toxic. Once combined however, edema toxin causes edema and LT causes death by systemic shock in animals and humans. Consistent with its critical role in forming both toxins, PA has been identified as the protective component in vaccines against anthrax. The molecular mechanism of anthrax toxin action is as follows: PA is a 735-amino acid polypeptide that binds to the surface of mammalian cells by cellular receptors. Once bound, PA is activated by proteolytic cleavage by cellular proteases to a 63-kDa molecule capable of forming a ring-shaped heptamer in the plasma membrane of the targeted cell (FIG. 1) (Milne et al., (1994) J. Biol. Chem. 269, 20607-20612, Petosa, et al., (1997) Nature (London) 385, 833-838). The PA heptamer then binds either EF or LF, which are internalized by endocytosis. After endosomal acidification, PA enables EF or LF to enter the cytosol, presumably by means of a pore formed by the heptamer. Within the cytosol, EF acts as an adenylate cyclase (Leppla, S. H. (1982) Proc. Natl. Acad. Sci. USA 79, 3162-3166) to convert ATP to cAMP. Abnormally elevated levels of cAMP perturb cellular metabolism.

Anthrax lethal factor or LF is a protein encoded by GenBank Accession number M29081 (GeneID No: 14343) that is naturally produced by *B. anthracis* and that has MAPKK protease activity. Deletion analysis of LF shows that the PA binding domain is located within the amino-terminus of LFn, and that mutational studies demonstrate the PA binding domain is located within the region of 34 to 254 of the LF polypeptide of SEQ ID NO: 1, and within the region of 34 to 288 of the LF polypeptide of SEQ ID NO: 2 (Arora et al., J. Biol. Chem. 268:3334 3341 (1993); Milne, et al., (1995) Mol. Microbiol. 15, 661-66).

The action of LF in the cytosol causes the death of host cells by a mechanism that is not well understood. LF induces over-production of a number of lymphokines (Klimpel, et al., (1994) Mol. Microbiol. 13, 1093-1100), contributing to lethal systemic shock in host animals. Recent studies also show that LF has two enzymatic activities: it can act as a zinc metalloprotease (Duesbery, et al., (1998) Science 280, 734-737), and it inactivates mitogen-activated protein kinase (Hanna, et al.,. (1994) Mol. Med. 1, 7-18). Although it is still not clear how these two enzymatic activities of LF are connected, both are required for LF toxicity. It has previously been reported that anthrax toxin B moieties can be used to deliver eptiopes which in turn elicit an antibody response by the immune system, in the presence of PA (WO 97/23236).

*B. anthracis* LF is a 796-aa polypeptide, and the functional domain for both enzymatic activities is located between amino acids 383 and 796 of SEQ ID NO: 1. The N-terminal truncated LF without this catalytic domain completely lacks any toxic effect when mixed with PA and added to cultured macrophages or when injected into animals. It does, however, still bind to PA effectively. The PA binding domain of LFn occurs within residues 34-288 of SEQ ID NO: 2 (Milne, et al., (1995) Mol. Microbiol. 15, 661-66).

The 83 kDa PA polypeptide binds at its carboxyl-terminus to a cell surface receptor, where it is specifically cleaved by a protease, e.g., furin, clostripain, or trypsin. This enzymatic cleavage releases a 20 kDa amino-terminal PA fragment, while a 63 kDa carboxyl-terminal PA fragment remains bound to the cell surface receptor. The 63 kDa fragment is also referred to as "processed protective antigen." Processed PA contains both a cell surface receptor binding site at its carboxyl-terminus and a lethal factor binding site at its new amino-terminus (see, e.g., Singh et al., J. Biol. Chem. 264:19103 19107 (1989)). Processed PA can be produced by enzymatic cleavage in vitro, ex vivo or in vivo, or as a recombinant protein. As used herein the term PA refers PA molecules that have the lethal factor binding site, e.g., recombinant PA, naturally occurring PA, functional equivalents of PA that contain the lethal factor binding site, and PA fusion proteins that contain the lethal factor binding site.

II. Compositions Comprising LF Polypeptides and Target Antigen

The inventors have established that a fragment of the lethal factor (LF) polypeptide of *Bacillus anthracis* (*B. anthracis*) can deliver a fused target antigen to the cytosol of an intact cell. In particular, the inventors have previously demonstrated that in the absence of PA, a target antigen which is covalently attached (i.e. by a covalent bond or fused) to an LF polypeptide such as LFn or a fragment thereof can be used to deliver an antigen to the cytosol of an intact, living cell and elicit a CTL response to the fused antigen. Surprisingly, the inventors herein have discovered that it is not necessary for the target antigen to be fused to an LF polypeptide to be delivered to the cell cytosol in the absence of PA. Thus, the inventors have now surprisingly discovered that LF polypeptides, such as LFn and fragments or variants thereof can be used to deliver non-linked (i.e. non-fused) target antigens to the cytosol of a cell in the absence of PA. Accordingly, one aspect of the present invention described herein relates to the use of LF polypeptides, such as LFn or fragments or variants of LFn as an immune adjuvant to deliver non-linked (i.e. non-fused) antigens to the cytosol of a cell to elicit a CMI response against the antigen.

The methods, compositions and kits described herein employ an LF polypeptide to deliver a target antigen to the cytosol of a cell from a subject. The LF polypeptide compositions involved generally comprise an LF polypeptide and a target antigen, where the LF polypeptide, e.g., LFn is not covalently linked to target antigen.

Alternatively, in some embodiments of this and other aspects described herein, the LF polypeptide can be in a non-covalently linked complex or be associated with the target antigen in some way, for example, to form an LFn:target antigen complex, where the LFn and target antigen are associated by forces other than a covalent bond, such as van der Waals forces, electrostatic forces and the like. In some embodiments of this and other aspects described herein, the composition comprises an LF polypeptide:target antigen complex, where the LF polypeptide, e.g., LFn, is directly associated with the target antigen by van der Waals forces or other non-covalent interactions. In alternative embodiments, the composition comprises an LF polypeptide:target antigen complex, where the LF polypeptide, e.g., an LFn polypeptide is indirectly associated with the target antigen, for example by interaction of the LFn polypeptide with at least a third entity or moiety, and the target antigen also interacts with a separate portion of the third entity (that interacts with the LF polypeptide).

In some embodiments of this and other aspects described herein, the composition comprises an LF polypeptide or LFn polypeptide and a target antigen, where the LF polypeptide is not covalently linked to the target antigen but the LF polypeptide is non-covalently associated or complexed with the target antigen in some way. For example, to form an LFn:target antigen complex. In some embodiments, the composition comprises an LFn:target antigen complex, where the LFn (or fragment or variant thereof) is directly associated with the target antigen by van der Waals forces or other non-covalent interactions. In alternative embodiments, the composition comprises an LFn:target antigen complex, where the LFn (or fragment or variant thereof) is indirectly associated with the target antigen, such as for example by interaction of the LFn (or fragment or variant thereof) with at least one third moiety, and the target antigen interacts with the same third moiety that interacts with the LFn polypeptide. Such interactions can be any non-covalent bond association known by a skilled artisan, such as, for example but not limited to, van der Waals forces, hydrophilic interactions, hydrophobic interactions and other non-covalent interactions. In some embodiments, at least one, or at least two, or at least 3, or at least 4 or more third entities can be used to associate LFn (or a fragment or variant thereof) with the target antigen. For example, the present invention comprises compositions which comprise complexes such as, an LFn:moiety:target antigen complex, or Lfn:moiety:moiety:target antigen complex, Lfn:moiety:moiety:moiety:target antigen complex, and such like complexes. In some embodiments, a moiety which associates with LFn can be the same or different from a moiety which binds with the target antigen, and all the moieties can be the same within a complex, or different within the complex.

Alternatively, in this aspect and all other aspects described herein, the present invention also encompasses a complex where a moiety is covalently linked to either (but not both simultaneously) an LF polypeptide or a target. For example, a target antigen can be covalently bonded (e.g. fused) to a moiety, and the moiety can interact via non-covalent interactions with the LF polypeptide such that the target antigen and LF polypeptide form a complex. Conversely, an LF polypeptide can be covalently bonded (e.g. fused) to a moiety, and the moiety can interact via non-covalent interactions with the target antigen such that the target antigen and LF polypeptide form a complex. Importantly, while an LF polypeptide and target antigen can not be covalently linked to the same moiety, they can be covalently linked to different moieties which non-covalently interact with each other, i.e., an LF polypeptide can be covalently linked to moiety A, and a target antigen can be covalently linked to moiety B, and moiety-A can interact with moiety B via non-covalent interactions, to form a LF-moiety-A:moiety-B-target antigen complex.

A. Lethal Factor (LF) of *Bacillus anthracis* and the N-terminal Fragment (LFn)

As discussed briefly above, anthrax Lethal Factor or LF is a protein, encoded by GenBank Accession Number M29081 (Gene ID No: 143143), that is naturally produced by *B. anthracis* and that has MAPKK protease activity. Deletion analysis of LF shows that the PA binding domain is located within the amino-terminus of LFn. Mutational studies demonstrate the PA binding domain is located within the region of 34 to 254 of the LF polypeptide of SEQ ID NO: 1, and within the region of 34 to 288 of the LF polypeptide of SEQ ID NO: 2 (Arora et al., J. Biol. Chem. 268:3334 3341 (1993); Milne, et al., (1995) Mol. Microbiol. 15, 661-66). The three-dimensional atomic resolution structures of LF have now been solved by X-ray crystallography. Andrew D. Pannifer et. al., describes the crystal structure of LF and its complex with a 16-amino acid residue (16-mer) peptide representing the N-terminus of its natural substrate, MAPKK-2, in Nature vol. 414, pg. 229-233 (2001) as a protein that comprises four structural domains: domain I binds the membrane-translocating component of anthrax toxin, the protective antigen (PA); domains II, III and IV together create a long deep groove that holds the 16-residue N-terminal tail of MAPKK-2 before cleavage. Domain I is perched on top of the other three domains, which are intimately connected and comprise a single folding unit. The only contacts between domain I and the rest of the molecule are with domain II, and these chiefly involve charged polar and water-mediated interactions. The nature of the interface is consistent with the ability of a recombinant N-terminal fragment (residues 1-254, excluding the signal peptide) to be expressed as a soluble folded domain that maintains the ability to bind PA and enables the translocation of heterologous fusion proteins into the cytosol (Ballard, J. D., et. al., 1996, Proc. Natl Acad. Sci. USA 93, 12531-12534; Goletz, T. J. et al., 1997, Proc. Natl Acad. Sci. USA 94, 12059-12064). Moreover, deletion of the first 36 residues of LFn had no effect on its binding to PA or LF ability to be translocated across membranes (D. Borden Lacy, et.al., 2002, J. Biol. Chem., 277:3006-3010). Domain I consists of a 12-helix bundle that packs against one face of a mixed four-stranded β-sheet, with a large (30-residue) ordered loop, L1, between the second and third -strands forming a flap over the distal face of the sheet (see FIG. 1). The exact docking site on domain I for PA is unknown, but the integrity of the folded domain seems to be required, because a series of insertion and point mutants of buried residues in domain I that presumably disrupt the fold abrogate binding of PA and toxicity (Quinn, C. P., et. al., 1991, J. Biol. Chem., 266: 20124-20130; Gupta, P., et. al., 2001, Biochem. Biophys. Res. Comm , 280:158-163). In addition, LFn has been shown to deliver exogenous protein antigens to the major histocompatibility complex class I pathway in the cytosol of B-cells, CTL-cells and macrophages in the absence of PA (Huyen Cao, et. al., 2002, The Journal of Infectious Diseases; 185:244-251; N. Kushner, et. al., 2003, Proc Natl Acad Sci U S A. 100: 6652-6657). The PA-independent LFn mediated delivery of target antigen polypeptide depends on functional transport-associated proteins for intracellular antigen processing and transport into the endoplasmic reticulum for binding to MHC class I molecules.

An abrupt turn at the end of the last helix of domain I leads directly into the first helix of domain II (residues 263-297 and 385-550). Although sequence-based comparisons failed to yield any homology, the structural similarity with the catalytic domain of the *B. cereus* toxin, VIP2 (Protein Data Bank accession code 1QS2), is outstanding. Domain II and VIP2 superimpose with an RMSD of 3.3 Å and a sequence identity of 15%, as determined by DALI (Holm, L. & Sander, 1997, Nucleic Acids Res. 25, 231-234). VIP2 contains an NAD-binding pocket and conserved residues involved in NAD binding and catalysis. Domain II lacks these conserved residues; moreover, a critical glutamic acid that is conserved throughout the family of ADP ribosylating toxins (Carroll, S. F. & Collier, R. J., 1984, Proc. Natl Acad. Sci. USA 81, 3307-3311) is replaced by a lysine (K518). We therefore expect that domain II does not have ADP-ribosylating activity.

Domain III is a small α-helical bundle with a hydrophobic core (residues 303-382), inserted at a turn between the second and third helices of domain II. Sequence analysis has revealed the presence of a 101-residue segment comprising five tandem repeats (residues 282-382), and suggested that repeats 2-5 arose from a duplication of repeat 1. The crystal structure reveals that repeat 1 actually forms the second helix-turn element of domain II, whereas repeats 2-5 form the four helix-turn elements of the helical bundle, suggesting a mechanism of creating a new protein domain by the repeated replication of a short segment of the parent domain. Domain III is required for LF activity, because insertion mutagenesis and point mutations of buried residues in this domain abrogate function (Quinn, C. P., et. al., 1991, J. Biol. Chem. 266, 20124-20130). It makes limited contact with domain II, but shares a hydrophobic surface with domain IV. Its location is such that it severely restricts access to the active site by potential substrates such as the loops of a globular protein; that is, it contributes towards specificity for a flexible 'tail' of a protein substrate. It also contributes sequence specificity by making specific interactions with the substrate (see below).

Domain IV (residues 552-776) consists of a nine-helix bundle packed against a four-stranded -sheet. Sequence comparisons had failed to detect any homology with other proteins of known structure beyond the HExxH motif. The three-dimensional structure reveals that the β-sheet and the first six helices can be superimposed with those of the metalloprotease thermolysin, with an RMSD of 4.9 Å over 131 residues. Large insertions and deletions occur elsewhere within the loops connecting these elements, so that the overall shapes of the domains are quite different. In particular, a large ordered loop (L2) inserted between strands 42 and 43 of the sheet partly obscures the active site, packs against domain II, and provides a buttress for domain III.

A zinc ion (Zn2+) is coordinated tetrahedrally by a water molecule and three protein side chains, in an arrangement typical of the thermolysin family. Two coordinating residues are the histidines from the HExxH motif (His 686 and His 690) lying on one helix (44), as expected. The structure reveals that the third coordinating residue is Glu 735 from helix 46. Glu 687 from the HExxH motif lies 3.5 Å from the water molecule, well positioned to act as a general base to activate the zinc-bound water during catalysis. The hydroxyl group of a tyrosine residue (Tyr 728) forms a strong hydrogen bond (O—O distance 2.6 Å) to the water molecule, on the opposite side of Glu 687, and probably functions as a general acid to protonate the amine leaving group.

*B. anthracis* encodes an 809 amino acid LF polypeptide. The mature *B. anthracis* LF is a 796 amino acid polypeptide produced by cleavage of the N-terminal leader peptide. The functional domain for both enzymatic activities is located between amino acids 383 and 796 of SEQ ID NO: 1. The N-terminal truncated LF without this catalytic domain completely lacks any toxic effect when mixed with PA and added to cultured macrophages or when injected into animals. It does, however, still bind to PA effectively. The PA binding domain of LFn occurs within residues 34-288 of SEQ ID NO:2 (Milne, et al., (1995) Mol. Microbiol. 15, 661-66).

The gene encoded 809 amino acid polypeptide *B. anthracis* LF has seven potential N-glycosylation sites located at asparagine positions 62, 212, 286, 478, 712 736, and 757. Within the LFn (1-288), there are three potential N-glycosylation sites, at asparagine positions 62, 212, and 286, all of which have the potential of >0.51 according to the NetNGlyc 1.0 Prediction software from the Technical University of Denmark. The NetNglyc server predicts N-Glycosylation sites in proteins using artificial neural networks that examine the sequence context of Asn-Xaa-Ser/Thr sequons.

The term "LFn polypeptide" includes LF polypeptide fragments represented by SEQ ID NOs 3 and 4, as well as recombinant LFn, and functional LFn equivalents, fragments, and variants that retain the function to deliver the polypeptide target antigen (that is not covalently linked to the LFn polypeptide) to the cytosol of an intact cell, preferably a living cell. The term "LFn polypeptide" therefore includes functional LFn homologues such as polymorphic variants, alleles, mutants, and closely related interspecies variants that have at least about 60% amino acid sequence identity to LFn and have the function to deliver polypeptide target antigen that is not covalently linked to the LFn polypeptide to the cytosol of a cell, as determined using the assays described herein. In particular embodiments, the LFn polypeptides are substantially identical to LFn of SEQ ID NO: 3 and SEQ ID NO: 4 as disclosed herein. In some embodiments, some functional polymorphic variants, alleles, mutants, and closely related interspecies variants of LFn that function to deliver a polypeptide target antigen to an intact cell can be determined by the methods and assays as disclosed in U.S. patent application Ser. No. 10/473,190 which is incorporated herein by reference.

In some embodiments, an LFn mimetic is useful in the compositions and methods described herein. An "LFn mimetic" refers to a compound or molecule, e.g., a peptide, polypeptide, or small chemical molecule that functions as LFn to deliver a target antigen to the cytosol of a cell to induce a CMI response against the antigen. LFn mimetics thus include LFn homologues. LFn mimetics would also include small LFn peptides that retain the LFn function to deliver polypeptide antigens (not linked to the LFn mimetic) to the cytosol of the cell, and conservatively substituted variants thereof, as well as truncated versions of LFn that retain ability of LFn to deliver polypeptide antigens (not linked to the LFn mimetic) to the cytosol of a cell. LFn mimetics are tested using assays for a CMI response to the target antigen as disclosed herein and in the Examples of U.S. patent application Ser. No. 10/473,190 (which is incorporated herein in its entirety by reference), e.g., induction of a CTL response to the delivered target antigen. When testing for an LFn mimetic, LFn is typically used as a positive control for delivery of the target antigen to a cell.

Figure 3:
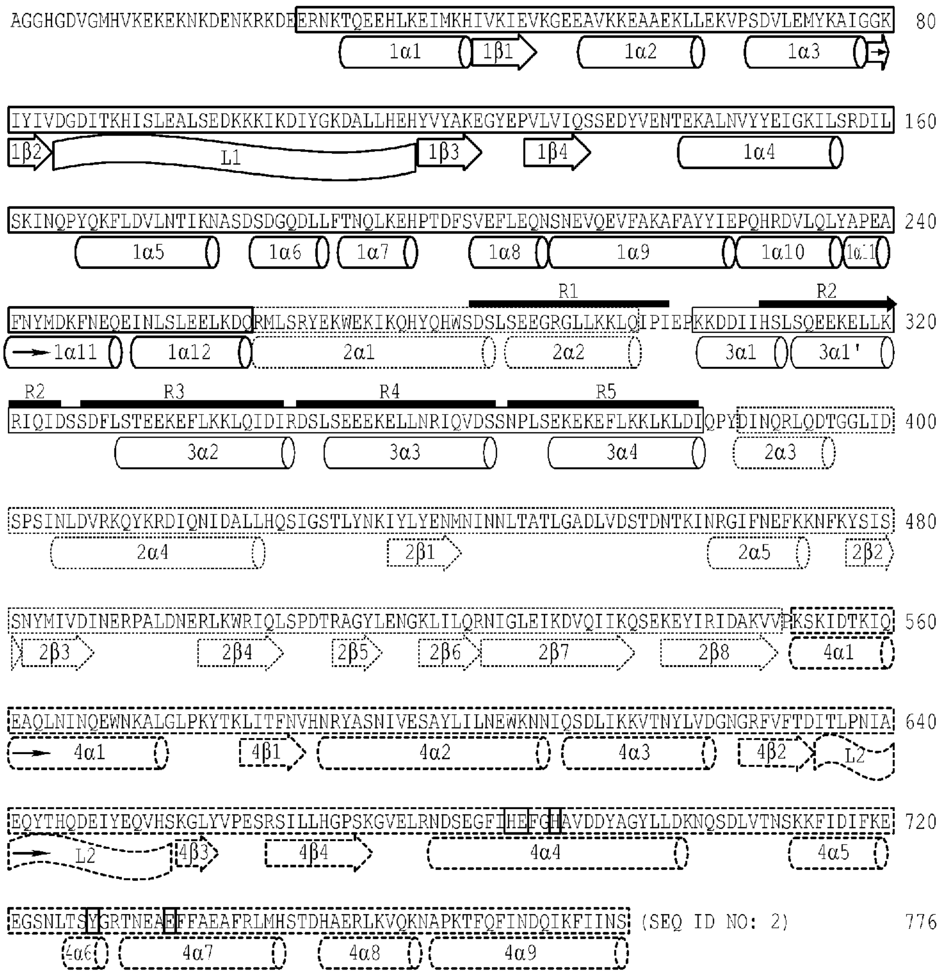
FIG. 3 shows the domains and secondary structure of the *Bacillus anthracis* Lethal Factor polypeptide based on the X-ray crystallography data from Andrew D. Pannifer et. al., (2001). Nature 414, 229-233. The N-terminal 1-33 amino acid residues are not shown. The consecutive varying gray-toned regions represent the domains I-IV from N-terminus to C-terminus.

While the whole of the N-terminal amino acid residues 1-288 (i. e. domain I, see FIG. 3) of the LF polypeptide promotes the transmembrane delivery of other proteins, it should be understood that smaller fragments of domain I can be sufficient to translocate across cell membrane and promote the transmembrane delivery of other proteins when non-covalently linked to the LF polypeptide. The x-ray crystal structure of domain I shows 12 alpha helices and four beta sheet secondary protein structure. Smaller fragments of domain I of an LF polypeptide that preserve alpha helices and/or beta sheet secondary protein structures of domain I can be used to translocate across cell membrane and promote the transmembrane delivery of other non-covalently linked proteins (i.e. target antigens). One skilled in the art can determine the presence of alpha helices and beta sheet secondary protein structure in an LF polypeptide using methods known in the art, such as circular dichroism (CD).

One aspect described herein is a means for eliciting a specific immune response, in particular a cell mediated cytotoxic immune response (CMI) to a target antigen, whereby a target antigen is delivered to the cytosol of a cell by being present in a non-covalently-linked form composition comprising an LF polypeptide, such as an LFn polypeptide or a fragment or variant thereof. In some embodiments of this and other aspects described herein, a preferred protein for delivery of non-fused (i.e. non-covalently linked) target antigens to the cytosol of a cell is an N-terminal fragment of the lethal Factor, herein referred to "LFn" and corresponds to amino acid SEQ ID NO: 4.

In some embodiments, the present invention relates to a means to elicit an immune response to a target antigen, where the target antigen is not fused to LFn, and where LFn contacts the target antigen and transduces the target antigen to the cytosol of a cell in the absence of PA.

One aspect of the present invention relates to a composition comprising an LFn polypeptide, or a homologue or fragment thereof and a target antigen, where the LFn is not covalently linked to the target antigen, and the LFn polypeptide or fragment thereof is not directly linked to the target antigen. In some embodiments, the composition does not comprise PA.

The inventors have discovered that a fragment of LFn which is at least about 250 amino acids or less, or at least about 150 amino acids or less, or at least about 104 amino acids or less, is able to deliver a target antigen to the cell and is useful in the methods and compositions described herein.

In one embodiment, the LFn polypeptide used in the delivery of the target antigen polypeptide comprises at least the 60 carboxy-terminal amino acids of SEQ. ID. No. 3, or a conservative substitution variant thereof. In another embodiment, the LFn polypeptide consists essentially of 60 carboxy-terminal amino acids of SEQ. ID. No. 3, or a conservative substitution variant thereof. In yet another embodiment, the LFn polypeptide consists of 60 carboxy-terminal amino acids of SEQ. ID. No. 3, or a conservative substitution variant thereof.

In one embodiment, the LFn polypeptide used to deliver the target antigen polypeptide comprises at least the 80 carboxy-terminal amino acids of SEQ. ID. No. 3, or a conservative substitution variant thereof. In another embodiment, the LFn polypeptide consists essentially of 80 carboxy-terminal amino acids of SEQ. ID. No. 3, or a conservative substitution variant thereof. In yet another embodiment, the LFn polypeptide consists of 80 carboxy-terminal amino acids of SEQ. ID. No. 3, or a conservative substitution variant thereof.

In one embodiment, the LFn polypeptide used to deliver the target antigen polypeptide comprises at least the 104 carboxy-terminal amino acids of SEQ. ID. No. 3, or a conservative substitution variant thereof. In another embodiment, the LFn polypeptide consists essentially of 104 carboxy-terminal amino acids of SEQ. ID. No. 3, or a conservative substitution variant thereof. In yet another embodiment, the LFn polypeptide consists of 104 carboxy-terminal amino acids of SEQ. ID. No. 3, or a conservative substitution variant thereof.

In one embodiment, the LFn polypeptide used to deliver the target antigen polypeptide consists of the amino acid sequence corresponding to SEQ. ID. No. 5, or a conservative substitution variant thereof. In another embodiment, the LFn polypeptide consists essentially of the amino acid sequence corresponding to SEQ. ID. No. 5, or a conservative substitution variant thereof. In yet another embodiment, the LFn polypeptide comprises of the amino acid sequence corresponding to SEQ. ID. No. 5, or a conservative substitution variant thereof.

In one embodiment, the LFn polypeptide used to deliver the target antigen polypeptide comprises the amino acid sequence corresponding to SEQ. ID. No. 4, or a conservative substitution variant thereof. In another embodiment, the LFn polypeptide consists essentially of the amino acid sequence corresponding to SEQ. ID. No. 4, or a conservative substitution variant thereof. In yet another embodiment, the LFn polypeptide consists of the amino acid sequence corresponding to SEQ. ID. No. 4, or a conservative substitution variant thereof.

In one embodiment, the LFn polypeptide used to deliver the target antigen polypeptide comprises the amino acid sequence corresponding to SEQ. ID. No. 3, or a conservative substitution variant thereof. In another embodiment, the LFn polypeptide consists essentially of the amino acid sequence corresponding to SEQ. ID. No. 3, or a conservative substitution variant thereof. In yet another embodiment, the LFn polypeptide consists of the amino acid sequence corresponding to SEQ. ID. No. 3, or a conservative substitution variant thereof.

In some embodiments, an LFn polypeptide as described herein comprises a non-functional binding site for PA, and thus is a mutant of LFn which does not result in functional binding with PA. Such mutants include, but are not limited to mutants altered at one or more of the residues critical for interacting with PA, such as a mutation in one or more of the following residues: Y22; L188; D187; Y226; L235; H229 (see Lacy et al., J. Biol. Chem., 2002; 277; 3006-3010); D106A; Y108K; E135K; D136K; N140A and K143A (see Melnyk et al., J. Biol. Chem., 2006; 281; 1630-1635 and Cunningham et al., PNAS, 2002; 99; 70497052, which are incorporated herein in their entirety by reference).

LFn polypeptides as described herein, or a conservative substitution variants thereof, promote transmembrane delivery of a target antigen that is not covalently linked to the LFn polypeptide. Methods of determining membrane translocation are well known in the art, as described, for example, in Wesche, J., et. al., 1998, Biochemistry 37: 15737-15746 and Sellman, B. R.,et. al., 2001 J. Biol. Chem. 276: 8371-8376. By way of brief explanation, CHO-K1 cells in a 24-well plate are chilled on ice, washed, and incubated on ice for 2 h with any of the LF polypeptide (or a conservative substitution variant thereof or fragments of domain I) and a target antigen as described herein that have been labeled with [35S]methionine in an in vitro transcription/translation system (Promega). The cells then are washed with ice-cold PBS at pH 5.0 or 8.0, incubated at 37° C. for 1 min, and either treated with Pronase to digest residual untranslocated 35S at the cell surface or left untreated as controls. The cells are then lysed, and 35S liberated into the lysis buffer is assayed. The percent translocation is defined as dpm protected from Pronase/dpm bound to cells x 100. The cell lysate of cells incubated with LF polypeptides or fragments of domain I that facilitate transmembrane delivery would have higher percent translocation.

Alternatively, a target antigen and/or an LFn polypeptide can be modified or labeled to allow each to be monitored for transmembrane delivery. For example, an LF polypeptide (such as LFn, LF or smaller fragments of domain I) can be fused to a fluorescent molecule, such as a green fluorescent protein which is useful to assay for membrane translocation capability, as described in N. Kushner, et. al., 2003, Proc Natl Acad Sci U S A. 100: 6652-6657. Briefly, HeLa cells (American Type Culture Collection) are grown on collagen-treated chamber slides (BD Science) to reach ~80% confluence and incubated with 40 μg/m1 purified GFP or LFn-GFP at 37° C. for 1 or 2 h. After washing, GFP fluorescence is compared between GFP and GFP-LFn treated samples. Membrane translocation is evidenced by GFP signal greater in the LFn-GFP-treated cells than in cells treated with GFP alone. Some incubations can also be performed in the presence of 100 μg/m1 Texas red-conjugated transferrin (Invitrogen Inc., Molecular Probes) as a marker for the endocytic pathway. For the transferrin experiments, cells are washed four times with cold DMEM and then fixed for 15 min in 4% paraformaldehyde in cold PBS. For antibody labeling, slides are then incubated on ice for 15 min in 50 mM $NH_4Cl$ in PBS and then in PBS containing 0.1% saponin for 20 min on ice. After further washing in PBS, slides are incubated at room temperature for 1 hr in a moisture chamber with PBS containing 4% donkey serum and the following primary antibodies: mouse anti-early endosome antigen 1 (EEA-1) (BD Laboratory) to stain early endosomes, mouse anti-Lamp1 and anti-Lamp2 (Developmental Studies Hybridoma Banks, University of Iowa, Iowa City) to stain late endosomes and lysosome, mouse Ab-1 (Oncogene) to stain the Golgi apparatus, mouse anti-mitochondrial antibody from Calbiochem, and rabbit anti-calreticulin (StressGen Biotechnologies, Victoria, Canada). Cells are then processed for secondary antibody staining and microscopy. Fusion LFn-GFP that promotes transmembrane delivery would be visualized in the interior of the cell. The antibody markers will further indicate sub-cellular localization of the translocated GFP.

As discussed above briefly, in one embodiment, an LFn polypeptide useful in the compostions and methods described herein does not bind *B. anthracis* protective antigen (PA) protein. The PA protein is the natural binding partner of LF, forming bipartite protein exotoxin, lethal toxin (LT). The PA protein is a 735-amino acid polypeptide, a multi-functional protein that binds to cell surface receptors, mediates the assembly and internalization of the complexes, and delivers them to the host cell endosome. Once PA is attached to the host receptor, it is cleaved by a host cell surface (furin family) protease before it is able to bind LF. The cleavage of the N-terminus of PA enables the C-terminal fragment to self-associate into a ring-shaped heptameric complex (prepore) that can bind LF and delivers LF into the cytosol. The N-terminal fragment (residues 1-288, domain I) can be expressed as a soluble folded domain that maintains the ability to bind PA and enables the translocation of non-covalently linked target antigen proteins into the cytosol. Smaller fragments of this residue 1-288 N-terminal fragment have been shown to also translocate heterologous fusion proteins into the cytosol in the absence of PA. Hence, in one embodiment, smaller fragments of LF described herein can translocate across membranes but do not bind PA. Methods of measuring or detecting protein-protein interaction are well known. One skilled in the art can determine PA binding activity, for example, by mixing and incubating PA63 with LFn for a period of time, chemically cross-linking of any complex formed and analysis of the covalently linked complex by gel electrophoresis or by radioactivity counting as described by Quinn C P. et. al., 1991, J. Biol. Chem. 266:20124-20130. Briefly, the binding assay is determined at 5° C. by competition with radiolabeled 125 I-LFn. Native LF or full-length N-terminal (amino acid 1-288) LFn is radiolabeled (~7.3x106 cpm/μg protein) using Bolton-Hunter reagent (Amersham Corp). For binding studies, J774A.1 cells cultured in 24-well tissue culture plates are cooled by incubating at 4° C. for 60 min and then placing the plates on ice. The medium is then replaced with cold (4° C.) minimal essential medium containing Hanks' salts (GIBCO/BRL) supplemented with 1% (w/v) bovine serum albumin and 25 mM HEPES (binding medium). Native PA (0.1 g/ml) is added with radiolabeled native LF (125I-LF, 0.1 μg/ml, $7.3\times10^6$ cpm/μg) and the plates incubated for 14 h on wet ice. Mutant LF proteins are assayed at varying concentrations for their ability to compete with native 125I-LF. For quantitation of bound, radiolabeled LF, cells are gently washed twice in cold binding medium, once in cold Hanks' balanced salt solution, solubilized in 0.50 ml of 0.1 M NaOH, and counted in a gamma counter (Beckman Gamma 9000).

In one embodiment, an LFn polypeptide substantially lacks the amino acids 1-33 of SEQ. ID. No. 3. Amino acids 1-33 of SEQ. ID. No. 3 encompass the signal peptide that is predicted to direct the post-translational transport of the LF protein. In some embodiments, an LFn polypeptide lacks a signal peptide that functions to direct the post-translational transport of the LF polypeptide. In other embodiments, an LFn polypeptide comprises a signal peptide for co-translation on the ER. The signal peptide is also called a leader peptide in the N- terminus, which can or can not be cleaved off after the translocation through the ER membrane. One example of a signal peptide is MAPFEPLASGILLLL-WLIAPSRA (SEQ ID NO: 6). Other examples of signal peptides can be found at SPdb, a Signal Peptide Database, which is found at the world wide web site of http colon "forward slash" "forward slash" proline "dot" bic "dot" nus "dot" edu "dot" sg "forward slash" spdb "forward slash".

In some embodiments, an LFn polypeptide as described herein is immune silent, or substantially inert, meaning that the LFn polypeptide does not function as an immunogen (i.e. it is not a target antigen) and does not substantially generate a CMI response to itself.

In one embodiment, the LF polypeptide is N-linked glycosylated. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. One skilled in the art can use bioinformatics software such as NetNGlyc 1.0 Prediction software from the Technical University of Denmark to find the N-glycosylation sites in an LF polypeptide of the present invention. The NetNglyc server predicts N-Glycosylation sites in proteins using artificial neural networks that examine the sequence context of Asn-Xaa-Ser/Thr sequons. The NetNGlyc 1.0 Prediction software can be accessed at the EXPASY website. In one embodiment, N-glycosylation occurs in the target antigen polypeptide as described herein. In another embodiment, N-glycosylation occurs in an LF polypeptide such as an LFn polypeptide as described herein, for example, at asparagine positions 62, 212, and/or 286, all of which have the potential of >0.51 according to the NetNGlyc 1.0 Prediction software. Various combinations of N-glycosylation in LF polypeptides of the present invention are possible. In some embodiments, an LF polypeptide described herein has a single N-glycosylation at one of these three sites: asparagine positions 62, 212, and 286. In some other embodiments, an LF polypeptide described herein is N-glycosylated at two of these three sites: asparagine positions 62, 212, and 286. In another embodiment, an LF polypeptide described herein is N-glycosylated at all three sites: asparagine positions 62, 212, and 286. In yet another embodiment, N-glycosylation occurs in both the target antigen polypeptide and the LFn polypeptide. In some embodiments, the glycans of the LF polypeptide and/or target antigen as described herein are modified, for example, sialyated or asialyated. Glycosylation analysis of proteins is known in the art. For example, via glycan hydrolysis (using enzymes such as N-glycosidase F, EndoS endoglycosidase, sialidase or with 4N trifluroacetic acid), derivitization, and chromatographic separation such as LC-MS or LC-MS/MS (Pei Chen et. al., 2008, J. Cancer Res. Clin. Oncology, 134: 851-860; Kainz, E. et. al., 2008, Appl Environ Microbiol., 74: 1076-1086).

The gene encoded 809-aa polypeptide *B. anthracis* LF is not predicted to have any O-glycosylation sites according to the NetOGlyc 3.1 Prediction software from the Technical University of Denmark. The NetOglyc server produces neural network predictions of mucin type GalNAc O-glycosylation sites in proteins. However, in some embodiments, the LFn used herein is N-glycosylated.

In one embodiment, the LFn and/or antigen compositions described herein comprise glycosylated proteins. In other words, the LF, LFn or the target antigens can each be glycosylated proteins, e.g., with O-linked glycosylation or N-linked glycosylation. In yet another embodiment, the LF, LFn or the target antigens can be both O-linked and N-linked glycosylated. In other embodiments, other types of glycosylations are possible, e.g. C-mannosylation. In one embodiment of the vaccine compositions described herein, the LFn polypeptide is N-glycosylated. Glycosylation of proteins occurs predominantly in eukaryotic cells. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. O-linked glycosylation occurs at a later stage during protein processing, probably in the Golgi apparatus. In O-linked glycosylation, N-acetyl-galactosamine, O-fucose, O-glucose, and/or N-acetylglucosamine is added to serine or threonine residues. One skilled in the art can use bioinformatics software such as NetNGlyc 1.0 and NetOGlyc Prediction softwares from the Technical University of Denmark to find the N- and O-glycosylation sites in a polypeptide in the present invention. The NetNglyc server predicts N-Glycosylation sites in proteins using artificial neural networks that examine the sequence context of Asn-Xaa-Ser/Thr sequons. The NetNGlyc 1.0 and NetOGlyc 3.1 Prediction software can be accessed at the EXPASY website. In one embodiment, N-glycosylation occurs in the target antigen polypeptide of the fusion polypeptide described herein. In another embodiment, N-glycosylation occurs in the LFn polypeptide of a fusion polypeptide described herein, for example, at asparagine positions 62, 212, and/or 286, all of which have the potential of >0.51 according to the NetNGlyc 1.0 Prediction software.

Various combinations of N-glycosylation in the fusion polypeptide of the present invention are possible. In some embodiments, the individual and fusion polypeptides described herein have a single N-glycosylation at one of these three sites: asparagine positions 62, 212, and 286 of LFn. In other embodiments, the individual and fusion polypeptides described herein are N-glycosylated at two of these three sites: asparagine positions 62, 212, and 286 of LFn. In another embodiment, the individual and fusion polypeptides described herein is N-glycosylated at all three sites: asparagine positions 62, 212, and 286 of LFn. In yet another embodiment, N-glycosylation occurs in both the target antigen polypeptide and the LFn polypeptide. In some embodiments, the glycans of the LFN and target antigent polypeptides described herein are modified, for example, sialyated or asialyated. Glycosylation analysis of proteins is known in the art, for example, via glycan hydrolysis (using enzymes such as N-glycosidase F, EndoS endoglycosidase, sialidase or with 4N trifluroacetic acid), derivitization, and chromatographic separation such as LC-MS or LC-MS/MS (Pei Chen et. al., 2008, J. Cancer Res. Clin.Oncology, 134: 851-860; Kainz,E. et. al., 2008, Appl. Environ. Microbiol., 74: 1076-1086). LFn is predicted to have no O-linked glycosylation sites of >0.50 potential.

In one embodiment, an LFn polypeptide as described herein is expressed bacterial cells and purified from a protein expression system using host cells selected from the group consisting of: mammalian cells, insect cells, yeast cells, and plant cells. The cloning, protein expression, and purification of recombinant proteins are known. One skilled in the art can use modern molecular techniques to construct an isolated polynucleotide encoding any of the LF polypeptides described herein, and ligate the isolated polynucleotide into a vector to form a recombinant vector, wherein the recombinant vector is an expression vector that is compatible with a protein expression system using host cells selected from the group consisting of: bacterial cells; mammalian cells; insect cells; yeast cells; and plant cells. Thus, mammalian cells, insect cells, yeast cells and plant cells are preferred. It is preferred that the host cell can N-glycosylate the recombinant LF polypeptide. There are many options for an expression vector depending on the choice of protein expression system and the types of host cells used. In one embodiment, the recombinant vector is a viral vector, such as, a recombinant baculovirus vector, an adeno-associated virus (AAV) vector or a lentivirus vector. Viral vectors provide ease of introducing the coding polynucleotide construct into the desired host cells. For example, adeno-associated virus (AAV) vector or a lentivirus vector infects mammalian cells and baculovirus vectors infect lepidopteran insect cells, such as, Spodoptera frugiperda cells. Expression of an LFn polypeptide as described herein in eukaryotic host cells, e. g, mammalian cells and insect cells can result in N-glycosylation of the LFn polypeptide thus expressed.

B. Production of LF Polypeptides i. Expression Systems:

Recombinant proteins, such an LF polypeptide as described herein can be readily produced by routine methods by one or ordinary skill in the art, such as by routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Nucleic acid sequences encoding an LF polypeptide which is not commercially available can be chemically synthesized according to the solid phase phosphoramidite triester method first described by Beaucage & Caruthers, Tetrahedron Letts. 22:1859 1862 (1981), using an automated synthesizer, as described in Van Devanter et. al., Nucleic Acids Res. 12:6159 6168 (1984). Purification of oligonucleotides is by either native acrylamide gel electrophoresis or by anion-exchange HPLC as described in Pearson & Reanier, J. Chrom. 255:137 149 (1983). The sequence a synthetic oligonucleotide or a cloned gene encoding an LF polypeptide can be verified after cloning using, e.g., the chain termination method for sequencing double-stranded templates of Wallace et al. Gene 16:21 26 (1981).

A. Cloning Methods for the Isolation of Nucleotide Sequences Encoding LFn.

In general, the nucleic acid sequences encoding an LF polypeptide such as LFn can be cloned from cDNA and genomic DNA libraries or isolated using amplification techniques with oligonucleotide primers. For example, LFn sequences are typically isolated from *B. anthracis* nucleic acid (genomic or cDNA) libraries.

The coding DNA sequences are typically cloned into intermediate vectors before transformation into prokaryotic or eukaryotic cells for replication and/or expression. These intermediate vectors are typically prokaryote vectors, e.g., plasmids, or shuttle vectors, as described below.

Amplification techniques using primers can also be used to amplify and isolate LFn coding sequences from DNA or RNA (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of LF directly from mRNA, from cDNA, from genomic libraries or cDNA libraries, and from plasmids. Degenerate oligonucleotides can be used to amplify homologues. These primers can be used, e.g., to amplify a probe of several hundred nucleotides, which is then used to screen a human library for full-length LF, which can be then be used to generate LFn. Alternatively, the nucleic acid for LFn can be directly amplified.

Nucleic acids encoding an LF polypeptide such as LFn can also be isolated from expression libraries using antibodies as probes. Synthetic oligonucleotides can be used to construct recombinant LFn genes for use as probes, for expression of protein, and for construction of polymorphic variants or mutants such as deletion mutants. This method is performed using a series of overlapping oligonucleotide: usually 40 120 by in length, representing both the sense and nonsense strands of the gene. These DNA fragments are then annealed, ligated and cloned.

Polymorphic variants, alleles, and interspecies homologues that are substantially identical to LFn can be isolated using LFn nucleic acid probes and oligonucleotides under stringent hybridization conditions, by screening libraries using probes, or using amplification techniques as described above. Alternatively, expression libraries can be used to clone polymorphic variant, alleles, and interspecies homologues, by detecting expressed homologues immunologically with antisera or purified antibodies, which also recognize and selectively bind to the homologue.

The gene encoding LF has been cloned and sequenced, and has been assigned Genebank accession no. M29081 (Robertson & Leppla, Gene 44:71 78 (1986); Bragg & Robertson, Gene 81:45 54 (1989); see also U.S. Pat. Nos. 5,591,631, 5,677,274; see generally Leppla, Anthrax Toxins, in Bacterial Toxins and Virulence Factors in Disease (Moss et al., eds., 1995)).

The nucleic acids of interest are typically cloned into intermediate vectors before transformation into prokaryotic or eukaryotic cells for replication and/or expression. These intermediate vectors are typically prokaryote vectors, e.g., plasmids, or shuttle vectors, as described below.

To obtain high level expression of a cloned gene, such as those cDNAs encoding LFn, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the LFn protein are available in, e.g., *E. coli, Bacillus* sp., and *Salmonella* (Palva et al., Gene 22:229 235 (1983); Mosbach et al., Nature 302:543 545 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application and is not critical. Exemplary promoters include the SV40 early promoter, SV40 later promoter, metallothionein promoter, murine mammary tumor virus promoter, Rous sarcoma virus promoter, polyhedrin promoter, or other promoters shown effective for expression in eukaryotic cells, as well as prokaryotic promoters. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus also contains signals required for efficient polyadenylation of the transcript, ribosome binding sites, and translation termination. The nucleic acid sequence encoding the gene of choice can typically be led to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of Heliothis virescens. Additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

Additional elements that are typically included in expression vectors also include a replicon that functions in E. coli, a gene encoding antibiotic resistance to permit selection of bacteria that harbor recombinant plasmids, unique restriction sites in nonessential regions of the plasmid to allow insertion of eukaryotic sequences. In addition, some expression systems have markets that provide gene amplification such as thymidine kinase, hygromycin B phosphotransferase, and dihydrofolate reductase. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

The particular expression vector used to transport the genetic information into the cell is not particularly critical. Any of the conventional vectors used for expression in eukaryotic or prokaryotic cells can be used. Standard bacterial expression vectors include plasmids such as pBR322 based plasmids, pSKF, pET23D, and, in some instances fusion expression systems such as GST and LacZ. Other exemplary eukaryotic vectors include pMSG, pAV009/A.sup.+, pMTO10/A.sup.+, pMAMneo-5, baculovirus pDSVE. Tags can also be added to recombinant proteins to provide convenient methods of isolation, e.g., c-myc, or hexahistidine.

Standard transfection methods are used to produce bacterial, mammalian, yeast or insect cell lines that express large quantities of LFn protein, which are then purified using standard techniques (see.e.g. Colley et al. J. Biol. Chem. 264:17619 17622 (1989); Guide to Protein Purification, in Methods in Enzymology, vol. 182 (Deutscher, ed., 1990)). Transformation of eukaryotic and prokaryotic cells are performed according to standard techniques, e.g., calcium phosphate transfection, polybrene, protoplast fusion, electroporation, liposomes, microinjection, plasma vectors, viral vectors (see, e.g., Morrison, J. Bact. 132:349 351 (1977); Clark-Curtiss & Curtiss, Methods in Enzymology 101:347 362 (Wu et al., eds, 1983).

After the expression vector is introduced into the cells, the transfected cells are cultured under conditions favoring expression of the gene of choice, which is recovered from the culture using standard techniques identified below.

LF polypeptides as disclosed herein e.g., an LFn polypeptide can all be synthesized and purified by protein and molecular methods that are well known to one skilled in the art. Preferably molecular biology methods and recombinant heterologous protein expression systems are used. For example, recombinant protein can be expressed in mammalian, insect, yeast, or plant cells.

Some examples of recombinant cloning and truncation of LF, LFn, their expression, and specific site mutations and insertions are described, for example, in WO/2002/079417, WO/2008/048289, US patent No. 20040166120, Huyen Cao, et. al., 2002, The Journal of Infectious Diseases;185: 244-251; N. Kushner, et. al., 2003, Proc Natl Acad Sci U S A. 100: 6652-6657; Ballard, J. D., et. al., 1996, Proc. Natl Acad. Sci. USA 93, 12531-12534; and Goletz, T. J. et al., 1997, Proc. Natl Acad. Sci. USA 94, 12059-12064, which are incorporated herein by reference in their entirety. Approaches similar to those described in these references can be used to produce an LF polypeptide, such as LFn polypeptide as described herein.

In one embodiment, an isolated polynucleotide encoding an LF polypeptide, such as LFn polypeptide described herein, can be produced by conventional polymerase chain reaction (PCR) cloning techniques as commonly known by persons of ordinary skill in the art. In some embodiments, an LF polypeptide and a target antigen can be expressed from the same expression vector, where each polynucleotide (i.e. one encoding the LF polypeptide and one encoding the target antigen) are separated so they are expressed as separate (non-covalently linked) proteins. Typically, the polynucleotide encoding an LF polypeptide and the polynucleotide encoding a target antigen are separated by an IRES (internal Ribosome Entry site) nucleic acid sequence. A polynucleotide encoding an LF polypeptide (and/or a target antigen polynucleotide) can be cloned into a general purpose cloning vector such as pUC19, pBR322, pBluescript vectors (Stratagene Inc.) or pCR TOPO® from Invitrogen Inc. The resultant recombinant vector carrying the nucleic acid encoding an LF polypeptide, such as LFn polypeptide as described herein can then be used for further molecular biological manipulations such as site-directed mutagenesis to create a variant LF polypeptide as described herein or can be subcloned into protein expression vectors or viral vectors for protein synthesis in a variety of protein expression systems using host cells selected from the group consisting of mammalian cell lines, insect cell lines, yeast, bacteria, and plant cells.

Each PCR primer should have at least 15 nucleotides overlapping with its corresponding templates at the region to be amplified. The polymerase used in the PCR amplification should have high fidelity such as Strategene's PfuUltra™ polymerase for reducing sequence mistakes during the PCR amplification process. For ease of ligating several separate PCR fragments together, for example in the construction of an LF polypeptide, such as LFn polypeptide, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the LF polypeptide, such as LFn polypeptide, coding DNA sequence is in-frame and will encode the LF polypeptide from beginning to end with no stop codons. At the same time the chosen restriction digestion sites should not be found within the coding DNA sequence for the LFn polypeptide. The coding DNA sequence for the fusion polypeptide can be ligated into cloning vector pBR322 or one of its derivatives, for amplification, verification of fidelity and authenticity of the chimeric coding sequence, substitutions/or specific site-directed mutagenesis for specific amino acid mutations and substitutions in the LF polypeptide.

Alternatively the coding DNA sequence for an LF polypeptide, such as an LFn polypeptide, can be PCR cloned into a vector using for example, Invitrogen's TOPO® cloning method in topoisomerase-assisted TA vectors such as pCR®-TOPO, pCR®-Blunt II-TOPO, pENTR/D-TOPO®, and pENTR/SD/D-TOPO®. Both pENTR/D-TOPO®, and pENTR/SD/D-TOPO® are directional TOPO entry vectors which allow the cloning of the DNA sequence in the 5'→3' orientation into a Gateway® expression vector. Directional cloning in the 5'→3' orientation facilitates the unidirectional insertion of the DNA sequence into a protein expression vector such that the promoter is upstream of the 5' ATG start codon of the LF polypeptide coding DNA sequence, enabling promoter driven protein expression. The recombinant vector carrying the coding DNA sequence for the LF polypeptide can be transfected into and propagated in general cloning *E. coli* such as XL1Blue, SURE (Stratagene) and TOP-10 cells (Invitrogen).

Standard techniques known to those of skill in the art can be used to introduce mutations (to create amino acid substitutions in the polypeptide sequence of an LF polypeptide, e.g., an LFn polypeptide described, i. e. SEQ. ID. No. 3 or 4 or 5) in the nucleotide sequence encoding an LFn polypeptide, e.g., SEQ. ID. No. 3 and 4, including, for example, site-directed mutagenesis and PCR-mediated mutagenesis. Preferably, the variant LF polypeptide has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to a LF or LFn polypeptide.

Certain silent or neutral missense mutations can also be made in the DNA coding sequence that do not change the encoded amino acid sequence or the capability to promote transmembrane delivery. These types of mutations are useful to optimize codon usage, or to improve recombinant protein expression and production.

Specific site-directed mutagenesis of a coding sequence for a polypeptide in a vector can be used to create specific amino acid mutations and substitutions. Site-directed mutagenesis can be carried out using, e. g. the QUIKCHANGE® site-directed mutagenesis kit from Stratagene according to the manufacturer's instructions.

In one embodiment, disclosed herein are expression vectors comprising the coding DNA sequence for an LF polypeptide, e.g., an LFn polypeptide described herein for the expression and purification of the recombinant LF polypeptide produced from a protein expression system using host cells selected from, e.g., mammalian, insect, yeast, or plant cells. The expression vector should have the necessary 5' upstream and 3' downstream regulatory elements such as promoter sequences, ribosome recognition and TATA box, and 3' UTR AAUAAA (SEQ ID NO: 11) transcription termination sequence for efficient gene transcription and translation in its respective host cell. The expression vector can have additional sequence such as 6X-histidine, V5, thioredoxin, glutathione-S-transferase, c-Myc, VSV-G, HSV, FLAG, maltose binding peptide, metal-binding peptide, HA and "secretion" signals (e.g., Honeybee melittin, PHO, Bip), which are incorporated into the expressed LF polypeptide. In addition, there can be enzyme digestion sites incorporated after these sequences to facilitate enzymatic removal of them after they are not needed. These additional sequences are useful for the detection of the LF polypeptide expression, for protein purification by affinity chromatography, enhanced solubility of the recombinant protein in the host cytoplasm, and/or for secreting the expressed LF polypeptide out into the culture media, or the spheroplast of the yeast cells. The expression of an LF polypeptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In one embodiment, a recombinant vector comprising an LF polypeptide such as an LFn polypeptide described herein is an expression vector that facilitates protein expression. In another embodiment, the expression vector comprising an LF polypeptide described herein is a viral vector, such as adenovirus, adeno-associated virus (AAV), retrovirus, baculovirus and lentivirus vectors, among others. The expression vectors can be viral or non-viral vectors. Recombinant viruses provide a versatile system for gene expression studies and therapeutic applications.

The LF polypeptide, e.g., an LFn polypeptide described herein can be expressed in a variety of expression host cells e.g., yeasts, mammalian cells, insect cells and plant cells such as *Chlamadomonas*, or even in cell-free expression systems. From the cloning vector, the nucleic acid can be subcloned into a recombinant expression vector that is appropriate for the expression of an LF polypeptide in mammalian, insect, yeast, or plant cells or a cell-free expression system such as a rabbit reticulocyte expression system.

Subcloning can be achieved by PCR cloning, restriction digestion followed by ligation, or recombination reaction such as those of the lambda phage-based site-specific recombination using the GATEWAY® LR and BP CLONASE™ enzyme mixtures. Subcloning should be unidirectional such that the 5' ATG start codon of the nucleic acid is downstream of the promoter in the expression vector. Some vectors are designed to transfer coding nucleic acid for expression in mammalian cells, insect cells and year in one single recombination reaction. For example, some of the GATEWAY® (Invitrogen) destination vectors are designed for the construction of baculovirus, adenovirus, adeno-associated virus (AAV), retrovirus, and lentiviruses, which upon infecting their respective host cells, permit heterologous expression of an LF polypeptide in the appropriate host cells. Transferring a gene into a destination vector is accomplished in just two steps according to manufacturer's instructions. There are GATEWAY® expression vectors for protein expression in insect cells, mammalian cells, and yeast. Following transformation and selection in E. coli, the expression vector is ready to be used for expression in the appropriate host.

Examples of other expression vectors and host cells are the strong CMV promoter-based pcDNA3.1 (Invitrogen) and pClneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™ HT (Invitrogen) for the expression in *Spodopera frugiperda* 9 (Sf9), Sf11, Tn-368 and BTI-TN-5B4-1 insect cell lines; pMT/BiP/V5-His (Invitrogen) for the expression in *Drosophila Schneider* S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

In some instances, a suitable system for expressing an LF polypeptide, such as an LFn polypeptide as described herein includes a baculovirus expression system (i.e. a BEVS system). In such a bacliovirus expression system, the first step is the construction of a recombinant baculovirus vector, either by homologous recombination or by site specific transposition. To obtain a recombinant baculovirus vector by homologous recombination, a baculovirus transfer vector is needed. A baculovirus transfer vector is a temporary vector whose sole purpose is to enable the insertion of foreign coding DNA, under an appropriate gene promoter, into the baculovirus genome at a site that would not affect normal viral replication. The baculovirus transfer vector comprises a portion of the baculovirus genomic sequence that spans the intended insertion site of the foreign coding DNA. The most common regions contain the polyhedrin or p10 gene. Both are dispensable for viral replication in cell culture and insect larvae and the production of infectious extracellular virus. Both proteins are highly expressed at a very late phase of viral replication and effect high level of transcription of the foreign gene when inserted back into the viral genome. A typical baculovirus transfer vector comprises a promoter, a transcriptional terminator, and most often native viral sequences and regions flanking both sides of the promoter that are homologous to the target genes in the viral genome. The region between the promoter and the transcriptional terminator can have multiple restriction enzyme digestion sites for facilitating cloning of the foreign coding sequence, in this instance, the coding DNA sequence for an LF polypeptide, e.g., an LFn polypeptide and a target antigen. Additional sequences can be included, e.g., signal peptides and/or tag coding sequences (such as His-tag, MAT Tag, FLAG tag) recognition sequence for enterokinase, honeybee melittin secretion signal, beta-galactosidase, glutathione S-transferase (GST) tag upstream of the MCS) for facilitating the secretion, identification, proper insertion, positive selection of recombinant virus, and/or purification of the recombinant protein. Subsequent to the construction of the baculovirus transfer vector, it is mixed with AcNPV viral DNA and co-transfected into insect cells to establish an infection. The native polyhedrin gene is removed by a double-cross over homologous recombination event and replaced by the foreign coding sequence to be expressed in the insect cells. Inactivation of the polyhedrin gene by deletion or by insertion results in mutants that do not produce occlusions in infected cells. These occlusion-negative viruses form plaques that are different from plaques produced by wild-type viruses, and this distinctive plaque morphology is useful as a means to screen for recombinant viruses.

In one embodiment, an LF polypeptide described herein can be produced by expression from a recombinant baculoviruses vector. In another embodiment, any LF polypeptide described herein is expressed by an insect cell. In yet another embodiment, any LF polypeptide described herein is isolated from an insect cell. There are several benefits of protein expression with baculovirus in insect cells, including high expression levels, ease of scale-up, production of proteins with posttranslational modifications, and simplified cell growth. Insect cells do not require $CO_2$ for growth and can be readily adapted to high-density suspension culture for large-scale expression. Many of the post-translational modification pathways present in mammalian systems are also utilized in insect cells, allowing the production of recombinant protein that is antigenically, immunogenically, and functionally similar to the native mammalian protein.

As background only, and without wishing to be bound by theory, baculoviruses are DNA viruses in the family Baculoviridae. These viruses are known to have a narrow host-range that is limited primarily to Lepidopteran species of insects (butterflies and moths). The baculovirus *Autographa californica* Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics. Many baculoviruses, including AcNPV, form large protein crystalline occlusions within the nucleus of infected cells. A single polypeptide, referred to as a polyhedrin, accounts for approximately 95% of the protein mass of these occlusion bodies. The gene for polyhedrin is present as a single copy in the AcNPV viral genome. Because the polyhedrin gene is not essential for virus replication in cultured cells, it can be readily modified to express foreign genes. The foreign gene sequence is inserted into the AcNPV gene just 3' to the polyhedrin promoter sequence such that it is under the transcriptional control of the polyhedrin promoter. The Baculovirus Expression Vector System (BEVS) is a safe and rapid method for the abundant production of recombinant proteins in insect cells and insects pioneered in the laboratory of Dr. Max D. Summers.

Baculovirus expression systems are powerful and versatile systems for high-level, recombinant protein expression in insect cells. Expression levels up to 500 mg/1 have been reported using the baculovirus expression system, making it an ideal system for high-level expression. Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Baculoviruses are particularly well-suited for use as eukaryotic cloning and expression vectors. They are generally safe by virtue of their narrow host range which is restricted to arthropods. The U.S. Environmental Protection Agency (EPA) has approved the use of three baculovirus species for the control of insect pests. AcNPV has been applied to crops for many years under EPA Experimental Use Permits. AcNPV wild type and recombinant viruses replicate in a variety of insect cells, including continuous cell lines derived from the fall armyworm, *Spodoptera frugiperda* (Lepidoptera; Noctuidae). *S. frugiperda* cells have a population doubling time of 18 to 24 hours and can be propagated in monolayer or in free suspension cultures.

In one embodiment of this and other aspects as described herein, the invention provides a composition for raising or detecting a cell-mediated immune (CMI) response to a target antigen polypeptide, the composition comprising an LF polypeptide such as an LFn polypeptide or a fragment thereof which is not linked to a target antigen, or alternatively, is non-covalently linked to the target antigen and whereby the LF polypeptide promotes the transmembrane delivery of the target antigen to the cytosol of an intact cell.

A good number of baculovirus transfer vectors and the corresponding appropriately modified host cells are commercially available, for example, pAcGP67, pAcSECG2TA, pVL1392, pVL1393, pAcGHLT, and pAcAB4 from BD Biosciences; pBAC-3, pBAC-6, pBACgus-6, and pBAC-surf-1 from Novagen, and pPolh-FLAG and pPolh-MAT from Sigma Aldrich. One skilled in the art would be able to clone and ligate the coding region of the *Bacillus anthracis* lethal factor N-terminal (LFn) portion or fragment thereof using specially designed oligonucleotide probes and polymerase chain reaction (PCR) methodologies that are well known in the art. One skilled in the art would also be able to clone and ligate the coding sequence for an LF polypeptide into a selected baculovirus transfer vector. The coding sequences of LFn and the target antigen polypeptide or fragment thereof should be ligated in-frame and the chimeric coding sequence should be ligated downstream of the promoter, and between the promoter and the transcription terminator. Subsequent to that, the recombinant baculovirus transfer vector is transfected into regular cloning *Escherichia coli*, such as XL1Blue. Recombinant transfer vector DNA is then selected by antibiotic resistance to remove any non-recombinant plasmid DNA and subsequently amplified and purified for transfection into *Spodoptera frugiperda* (SF) cells.

As an example, the oligonucleotide 5'-GGAGGAACATATGGCGGGCGGTCATGGTGATG-3' (SEQ. ID. NO.9) is used to introduce an Ndel site and serve as a forward primer in the amplification of the coding DNA sequence for LFn-(amino acids 1-263) and the oligonucleotide 5'-CTAGGATCCTTACCGTTGATCTTTAAGTTCTTCC-3' (SEQ. ID. NO.10) is used to introduce a BamHI site and act as the reverse primer. PCR amplification is performed using the cDNA template according to GenBank Accession No. M29081. The forward primers for LFn-(28-263), LFn-(33-263), LFn-(37-263), LFn-(40-263), and LFn-(43-263) can be designed accordingly permit the PCR amplification of the coding sequence of the appropriate truncated LFn and also introduce an NdeI site. Accordingly, the polynucleotide coding sequence can be easily produced with a NdeI restriction site at the 5' and a BamHI restriction site a the 3' end, allowing unidirectional cloning into an appropriate expression cloning vector, such as a baculovirus expression vector. The sequences can introduce a stop sequence (TAA) after the coding region of the LF sequence. The common BamHI site at the end of the amplified coding sequence of LF facilitates the ligation of the amplified coding sequences into an appropriate expression vector, such as a selected baculovirus transfer vector that has Ndel and BamHI sites with the appropriate orientation. The newly constructed baculovirus transfer vector can be transformed into *Escherichia coli* DHS. *E. coli* transformants can be screened by digestion and verified by sequencing. After that, the baculovirus transfer vector can be isolated for co-transfection into insect cells for homologous recombination.

To obtain a recombinant baculovirus vector by site specific transposition, e. g. with Tn7 to insert foreign genes into bacmid DNA propagated in *E. coli*., Invitrogen Inc. provides the pFASTBACTM plasmid and bacmid containing DH10BAC™ competent *E. coli* for constructing a recombinant baculovirus vector by site specific transposition. The coding sequence is cloned into a pFASTBAC™ plasmid and the recombinant plasmid is transformed into an DH10BAC™ competent *E. coli* harboring bacmid, baculovirus shuttle vector, with a mini-attTn7 target site and a helper plasmid. The mini-attTn7 element on the pFASTBAC™ plasmid can transpose to the mini-attTn7 target site on the bacmid in the presence of transposition proteins provided by the helper plasmid. Colonies containing recombinant bacmids are identified by antibiotics selection and by blue/white screening, since the transposition results in the disruption of the LacZ gene that is flanked by the mini-attTn7 target site on the bacmid. The bacmid is then harvested for transfection of insect cells.

In some instances, specific site-directed mutagenesis of the chimeric coding sequence in the baculovirus transfer vector can be performed to create specific amino acid mutations and substitutions to further promote transmembrane delivery, protein expression or protein folding. Examples of amino acid substitutions include glutamate for aspartate. Site-directed mutagenesis can be carried out, e.g., using the QUIKCHANGE® site-directed mutagenesis kit from Stratagene according to manufacture's instructions or any methods known in the art.

Standard viral DNA is used to co-transfect *S. frugiperda* (SF) cells. Putative recombinant viruses containing the recombinant molecules are isolated from the virus expressed from these transfected monolayers. Because the polyhedrin structural gene has been removed, plaques containing the recombinant viruses can be easily identified since they lack occlusion bodies. Confirmation that these recombinants contain the desired chimeric coding sequence is established by methods well known in the art, such as hybridization with specific gene probes, plaque assays, and end point dilution.

A preferred host cell line for protein production from recombinant baculoviruses described herein is Sf900+. Another preferred host cell line for protein production from recombinant baculoviruses is Sf9. Sf900+ and Sf9 are non-transformed, non-tumorigenic continuous cell lines derived from the fall armyworm, *Spodoptera frugiperda* (Lepidoptera; Noctuidae).

Sf900+ and Sf9 cells are propagated at 28±2° C. without carbon dioxide supplementation. The culture medium used for Sf9 cells is TNMFH, a simple mixture of salts, vitamins, sugars and amino acids, supplemented with 10% fetal bovine serum. Aside from fetal bovine serum, no other animal derived products (i.e, trypsin, etc.) are used in cell propagation. Serum free culture medium (available as Sf900 culture media, Gibco BRL, Gaithersburg, Md.) can also be used to grow Sf9 cells and is preferred for propagation of Sf900+ cells. Sf9 cells have a population doubling time of 18-24 hours and can be propagated in monolayer or in free suspension cultures. *S. frugiperda* cells have not been reported to support the replication of any known mammalian viruses.

Plaque assays of baculovirus transfected monolayers SF cells are well known in the art. Once recombinant baculoviral vectors that express the proteins are established, then the virus can be amplified and purified for infection of SF cells.

Purification of Virus. Viral particles produced from the first passage are purified from the media using a known purification method such as sucrose density gradient centrifugation. For example, virus is harvested 24-48 hours post infection by centrifuging media of infected cells. The resulting viral pellet is resuspended in buffer and centrifuged through a buffered sucrose gradient. The virus band is harvested from the 40-45% sucrose region of the gradient, diluted with buffer and pelleted by centrifugation at 100,000×g. The purified virus pellet is resuspended in buffer and stored at −70° C. or used in large scale infection of cells for protein production.

The infection process, including viral protein synthesis, viral assembly and partial cell lysis can be complete by approximately 72 hours post-infection. This can be protein dependent and thus can occur earlier or later. The proteins produced in infected cells can radiolabeled with $^{35}$S-methionine, $^{3}$H-leucine, or $^{3}$H-mannose and both cell-associated and cell-free polypeptides can be analyzed by electrophoresis on polyacrylamide gels to determine their molecular weight. The expression of these products can also be examined at different times post-infection, prior to cell lysis.

In some embodiments, an LF polypeptide as described herein can be expressed from viral infection of mammalian cells. The viral vectors can be, for example, adenovirus, adeno-associated virus (AAV), retrovirus, and lentivirus. A simplified system for generating recombinant adenoviruses is presented by He TC. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

Recombinant lentivirus has the advantage of delivery and expression of an LF polypeptide, e.g., an LFn polypeptide that is not linked, or not covalently linked to a target antigen in either dividing and non-dividing mammalian cells. The HIV-1 based lentivirus can effectively transduce a broader host range than the Moloney Leukemia Virus (MoMLV)-base retroviral systems. Preparation of the recombinant lentivirus can be achieved using, for example, the pLenti4/V5-DEST™, pLenti6/V5-DEST™ or pLenti vectors together with ViraPower™ Lentiviral Expression systems from Invitrogen.

Recombinant adeno-associated virus (rAAV) vectors are applicable to a wide range of host cells including many different human and non-human cell lines or tissues. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors can be purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsC1 gradients.

ii. Protein Purification Systems:

An LF polypeptide, e.g., an LFn polypeptide described herein can be expressed and purified by a variety methods known to one skilled in the art. Recombinant LF or LFn polypeptides, for example, can be purified from any suitable expression system. Polypeptides can be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al. supra).

The next step is to purify the proteins for uses and compositions described herein, e. g. evaluation for use as vaccines or screening agents. If an LF polypeptide described herein is designed with secretion signal peptides, the encoded polypeptides are often released into the cell culture medium. Media from these infected cells can be concentrated and the proteins purified using standard methods. Salt precipitation, sucrose gradient centrifugation and chromatography, high or fast pressure liquid chromatography (HPLC or FPLC) can be used because these methods allow rapid, quantitative and large scale purification of proteins, and do not denature expressed products.

The efficiency of synthesis of the desired gene product is dependent on multiple factors including: (1) the choice of an expression vector system; (2) the number of gene copies that will be available in the cells as templates for the production of mRNA; (3) the promoter strength; (4) the stability and structure of the mRNA; (5) the efficient binding of ribosomes for the initiation or translation; (6) the properties of the protein product, such as, the stability of the gene product or lethality of the product to the host cells; (7) the ability of the system to synthesize and export the protein from the cells, thus simplifying subsequent analysis, purification and use.

A number of procedures can be employed when recombinant proteins are purified. For example, proteins having established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

After the protein is expressed in the host cells, the host cells can be lysed to liberate the expressed protein for purification. Methods of lysing the various host cells are featured in "Sample Preparation-Tools for Protein Research" EMD Bioscience and in the Current Protocols in Protein Sciences (CPPS). A preferred purification method is affinity chromatography such as metal-ion affinity chromatograph using nickel, cobalt, or zinc affinity resins for histidine-tagged LF polypeptides. Methods of purifying histidine-tagged recombinant proteins are described by Clontech using their TALON® cobalt resin and by Novagen in their pET system manual, 10th edition. Another preferred purification strategy is immuno-affinity chromatography, for example, anti-myc antibody conjugated resin can be used to affinity purify myc-tagged LF polypeptides. When appropriate protease recognition sequences are present, LF polypeptides can be cleaved from the histidine or myc tag, releasing the LF polypeptide from the affinity resin while the histidine-tags and myc-tags are left attached to the affinity resin. Non-tagged LF polypeptides can be affinity purified using copper affinity chromatography.

Standard protein separation techniques for purifying recombinant and naturally occurring proteins are well known in the art, e. g. solubility fractionation, size exclusion gel filtration, and various column chromatography.

Solubility Fractionation: Often as an initial step, particularly if the protein mixture is complex, an initial salt fractionation can separate many of the unwanted host cell proteins (or proteins derived from the cell culture media) from the protein of interest. The preferred salt is ammonium sulfate Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration: The molecular weight of the protein of choice can be used to isolated it from proteins of greater and lesser size using ultrafiltration through membranes of different pore size (for example. Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography: The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, LFn can be purified using a PA63 heptamer affinity column (Singh et al., J. Biol. Chem. 269:29039 29046 (1994)).

In some embodiments, a combination of purification steps comprising, for example: (i) anion exchange chromatography, (ii) hydroxyapatite chromatography, (iii) hydrophobic interaction chromatography, and (iv) size exclusion chromatography can be used to purify the LF polypeptides described herein.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin AS. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. Large scale cell-free production of the integral membrane protein EmrE multidrug transporter is described by Chang G. el. al., Science 310:1950-3 (2005).

Other commercially available cell-free expression systems include the EXPRESSWAY™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses rabbit reticulocyte-based in-vitro system.

C. Target Antigens

In one embodiment of this aspect and all other aspects described herein, a target antigen is any antigen whose delivery to the cytosol is desired. The target antigen is either not linked or non-covalently linked to an LF polypeptide. Thus, in some embodiments, antigens which are associated, for example by some form of non-covalent linkage such as electrostatic interactions, van der Waals forces etc. are also encompassed.

In some embodiments, antigens include viral, bacterial, parasitic, and tumor associated antigens. Preferred viral antigens include proteins from any virus where a cell-mediated immune response is desired. Particularly preferred viruses include HIV-1, HIV-2, hepatitis viruses (including hepatitis B and C), Ebola virus, West Nile virus, and herpes virus such as HSV-2. Preferred bacterial antigens include those from *S. typhi* and *Mycobacteria* (including *M. tuberculosis*). Preferred parasitic antigens include those from *Plasmodium* (including *P. falciparum*). An antigen can also include, for example, pathogenic peptides, toxins, toxoids, subunits thereof, or combinations thereof (e.g., tetanus, diphtheria toxoid, cholera subunit B, etc.).

In some embodiments, a target antigen polypeptide described herein is any antigen associated with a pathology, for example an infectious disease or pathogen, or cancer or an immune disease such as an autoimmune disease. In order to improve the likelihood of producing a cell mediated response to the target antigen, the amino acid sequence of a target antigen polypeptide can be analyzed in order to identify desired portions of amino acid sequence which can be involved or associated with receptor binding, such as binding to MHC receptors, or the target receptor to which the antigen binds. For example, a target antigen polypeptide sequences can be subjected to computer analysis to identify such sites.

In some embodiments, a target antigen is a whole virus or an attenuated virus, where an attenuated virus is a non-live or inactive virus. In such embodiments, a composition comprising an LF polypeptide such as an LFn polypeptide and a target antigen such as a whole virus, such as an attenuated virus which is not linked to the LF polypeptide, the LF polypeptide functions like a classic adjuvant (i.e. the LF polypeptide enhances the immunological response, such as a CMI response to the whole and/or attenuated virus target antigen).

One example of an infectious disease antigen is TbH9 (also known as Mtb 39A), a tuberculosis antigen. Other tuberculosis antigens include, but are not limited to, DPV (also known as Mtb8.4), 381, Mtb41, Mtb40, Mtb32A, Mtb9.9A, Mtb9.8, Mtb16, Mtb72f, Mtb59f, Mtb88f, Mtb71f, Mtb46f and Mtb31f ("f" indicates that it is a fusion or two or more proteins).

If an antigen is not readily soluble per se, the antigen can be present in the formulation in a suspension or even as an aggregate. In some embodiments, hydrophobic antigen can be solubilized in a detergent, for example a polypeptide containing a membrane-spanning domain. Furthermore, for formulations containing liposomes, an antigen in a detergent solution (e.g., a cell membrane extract) can be mixed with lipids, and liposomes then can be formed by removal of the detergent by dilution, dialysis, or column chromatography. Certain antigens such as, for example, those from a virus (e.g., hepatitis A) need not be soluble per se, but can be incorporated directly into a liposome in the form of a virosome (Morein and Simons, 1985).

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, or parasite).

Target bacteria include, but are not limited to: anthrax, *campylobacter*, cholera, diphtheria, enterotoxigenic *E. coli*, giardia, gonococcus, *Helicobacter pylori* (Lee and Chen, 1994), Hemophilus influenza B, Hemophilus influenzanon-typable, *meningococcus, pertussis, pneumococcus, salmonella, shigella, Streptococcus* B, group A *Streptococcus*, tetanus, *Vibrio cholerae, yersinia, Staphylococcus, Pseudomonas* species and *Clostridia* species.

Target viruses include, but are not limited to: adenovirus, dengue serotypes 1 to 4 (Delenda et al., 1994; Fonseca et al., 1994; Smucny et al., 1995), ebola (Jahrling et al., 1996), enterovirus, hepatitis serotypes A to E (Blum, 1995; Katkov, 1996;.Lieberman and Greenberg, 1996; Mast, 1996; Shafara et al., 1995; Smedila et al., 1994; U.S. Pat. Nos. 5,314,808 and 5,436,126), herpes simplex virus 1 or 2, human immunodeficiency virus (Deprez et al., 1996), influenza, Japanese equine encephalitis, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever.

Target parasites include, but are not limited to: Entamoeba histolytica (Zhang et al., 1995); *Plasmodium* (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), *Leishmania* (Frankenburg et al., 1996), Toxoplasmosis, and the Helminths.

Antigens can also comprise those used in biological warfare such as ricin, for which protection can be achieved via antibodies.

In this aspect and all other aspects described herein, a target antigen for use in the compositions of the present invention can be expressed by recombinant means, and in some embodiments, it can be expressed as a fusion with an affinity or epitope tag (Summers and Smith, 1987; Goeddel, 1990; Ausubel et al., 1996), or with a third entity for the purposes of forming a non-covalent linkage or complex with LF polypeptide; chemical synthesis of an oligopeptide, either free or conjugated to carrier proteins, can be used to obtain antigen of the invention (Bodanszky, 1993; Wisdom, 1994). Oligopeptides are considered a type of polypeptide.

In one embodiment, the target antigen is an intracellular pathogen target antigen polypeptide. A pathogen has been defined as a microorganism capable of causing damage to the host. An intracellular pathogen is a microorganism that can gain entry into the interior of a cell, live inside host cells and cause damage to the host and/or host cells. For example, the pathogen can be phagocytosed and/or endocytosed by a host cell, followed by the pathogen's escape from the phagosome or endosome. The pathogen then resides intracellularly to evade other/subsequent host defense, such as antibodies, and to multiply. Phagocytosis by macrophages is a primary frontline host defense mechanism against pathogens. When a pathogen fails to escape from the phagosome or endosome, the phagocytosed or engulfed pathogen is digested by the enzymes coming from the lysosomes. The digested, smaller peptides derived from pathogen proteins are complexed with host cell MHC molecules and displayed extracellularly to other immune cells in the host so as to stimulate the immune system of the host to respond to that particular pathogen. An intracellular pathogen target antigen polypeptide, when displayed and presented to host immune cells in the context of MHC molecules as described herein, can stimulate an immune response in the host that can involve numerous cellular processes known in the art of immunology. Aspects of such a response include an increase in cytokine production, increased antibody production, and increased B-cell multiplication. Intracellular pathogens include but are not limited to viruses, certain bacteria and certain protozoa. They cause a range of human diseases and ailments: tuberculosis, leprosy, typhoid fever, bacillary dysentery, plague, brucellosis, pneumonia, typhus; Rocky Mountain spotted fever, chlamydia, trachoma, gonorrhea, Listeriosis, scarlet/rheumatic fever, "strep" throat, hepatitis, AIDS, congenital viral infections, mononucleosis, Burkitts lymphoma and other lymphoproliferative diseases, cold sores, genital herpes, genital warts, cervical cancer, leishmaniasis, malaria, and trypanosomiasis to name but a few.

In one embodiment, the target antigen polypeptide is an intracellular pathogen target antigen polypeptide from a prokaryotic pathogen. A prokaryotic pathogen is a bacterium. In one embodiment, the intracellular prokaryotic pathogen includes but not limited to *Myocobacterium tuberculosis, Mycobacterium leprae, Listeria monocytogenes, Salmonella typhi, Shigella dysenteriae, Yersinia pestis, Brucella species, Legionella pneumophila, Rickettsiae, Chlamydia, Clostridium perfringens, Clostridium botulinum, Staphylococcus aureus, Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis*, and *Neisseria meningitides*.

In one embodiment, the target antigen polypeptide is an intracellular pathogen target antigen polypeptide from a viral pathogen, in which the virus naturally infects mammalian host cells. In one embodiment, the viral pathogen includes but is not limited to Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Rabies virus, Human T-cell Leukemia virus type-1, Hantavirus, Rubella virus and Simian Immunodeficiency virus.

In one embodiment, the target antigen polypeptide is an intracellular pathogen target antigen polypeptide of a parasitic pathogen. In one embodiment, the intracellular parasitic pathogen includes but is not limited to Myocobacterium tuberculosis, *Mycobacterium leprae, Listeria monocytogenes, Salmonella typhi, Shigella dysenteriae, Yersinia pestis, Brucella* species, *Legionella pneumophila, Rickettsiae, Chlamydia, Clostridium perfringens, Staphylococcus aureus, Treponema pallidum, Haemophilus influenzae, Treponema pallidum,Klebsiella pneumoniae, Pseudomonas aeruginosa, Streptococcus pneumoniae, Bordetella pertussis, Neisseria meningitides, Leishmania donovanii, Plasmodium* species, *Pneumocystis carinii, Trypanosoma* species, Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Rabies virus, Human T-cell Leukemia virus type-1, Hantavirus, Rubella virus and Simian Immunodeficiency virus.

In one embodiment, the target antigen polypeptide is an antigen of *M. tuberculosis*. In one embodiment, the target antigen polypeptide is a TB-specific antigen, including, but not limited to, TB1 (CFP) polypeptide comprising SEQ ID NO: 7 or a fragment thereof, or alternatively, TB2 (ESAT) polypeptide comprising SEQ ID NO: 8 or a fragment thereof.

In another embodiment, a target antigen polypeptide is an intracellular pathogen target antigen polypeptide at least 15 amino acids long. For example, a target antigen can be the 91 amino acid fragment (amino acids 27-117) of *P. falciparum* circumsporozoite protein, a predominant surface protein, that is involved in invasion of liver cells by *Plasmodium* sporozoites, which leads to malaria.

In alternative embodiments, the present invention can also be useful for eliciting a antigen-specific immune response against antigens such as viral antigens, such as sequestrin, to prevent the binding of erythrocytes to vascular endothelium in malaria by inducing anti-sequestrin antibodies. In alternative embodiments, the present invention can be used to elicit an antigen-specific immune response against viral antigens such as for the induction of protective antibodies such as anti-hepatitis A, B or hepatitis E antibodies, using the whole inactivated virus, or alternatively virus-derived subunits or recombinant products in the composition in combination with the LFn or fragment thereof.

In alternative embodiments, the compositions and methods as disclosed herein can be useful in the protection against tetanus, diphtheria and other toxin mediated diseases to induce the production of anti-toxin antibodies. For example, a tetanus "booster" is envisioned, where the composition as disclosed herein comprises LFn or a fragment thereof and a target antigen toxoid such as tetanus toxin or diphtheria, or fragments such as the tetanus C fragment. Boosting could be achieved following primary immunization by injection or transcutaneous immunization with the same or similar antigens, or woth standard vaccine compostions, e.g., a toxoid vaccine.

Vaccination can als be used as a treatment for cancer and autoimmune disease. For example, vaccination with a tumor antigen (e.g., prostate specific antigen or PSA) can induce an immune response in the form of antibodies, CTLs and lymphocyte proliferation which allows the body's immune system to recognize and kill tumor cells. Targeting dendritic cells, of which Langerhans cells are a specific subset, has been shown to be an important strategy in cancer immunotherapy.

In one embodiment of this aspect and all other aspects described herein, a target antigen is a tumor antigen. Many tumors are associated with the expression of a particular protein and/or the over-expression of certain proteins. For example, prostate cancer is associated with elevated levels of protein such as Prostate Specific Antigen (PSA). Breast cancers can be associated with the expression and/or over-expression of protein such as Her-2, Muc-1, CEA, etc. Thus, considerable attention has been aimed at trying to generate immune responses, particularly developing CMI, to such antigens in the treatment of such malignancies. Tumor antigens useful in this aspect and all other aspects described herein, include, for example PSA, Her-2, Mic-1 and CEA. Other tumor antigens include those epitopes which are recognized in eliciting T cell responses, including but not limited to the following: prostate cancer antigens (such as PSA, PSMA, etc.), breast cancer antigens (such as HER2/neu, mini-MUC, MUC-1, HER2 receptor, mammoglobulin, labyrinthine, SCP-1, NY-ESO-1, SSX-2, N-terminal blocked soluble cytokeratin, 43 kD human cancer antigens, PRAT, TUAN, Lb antigen, carcinoembryonic antigen, polyadenylate polymerase, p53, mdm-2, p21, CA15-3, oncoprotein 18/stathmin, and human glandular kallikrein), melanoma antigens, and the like. Tumor antigens useful to be delivered by an LF polypeptide according to the methods and compositions herein are described in use for melanoma (U.S. Pat. Nos. 5,102,663, 5,141,742, and 5,262,177 which are incorporated herein in their entirety by reference), prostate carcinoma (U.S. Pat. No. 5,538,866), and lymphoma (U.S. Pat. Nos. 4,816,249, 5,068,177, and 5,227,159 which are all incorporated herein in their entirety by reference).

In one embodiment of this aspect and all other aspects described herein, a target antigen is a T-cell receptor oligopeptide. For example, vaccination with T-cell receptor oligopeptide can induce an immune response that halts progression of autoimmune disease (U.S. Pat. Nos. 5,612,035 and 5,614,192; Antel et al, 1996; Vandenbark et al, 1996). U.S. Pat. No. 5,552,300 (which is incorporated herein in its entirety by reference) also describes antigens suitable for treating autoimmune disease. In one embodiment of this aspect and all other aspects described herein, a target antigen is a T-cell receptor V antigen, which is discussed in U.S. Pat. No. 5,552,300 (which is incorporated herein in its entirety by reference).

In one embodiment of this aspect and all other aspects described herein, a target antigen is a misfolded or improperly folded protein or polypeptide, for example a protein which is not in its native conformation. Examples of such proteins include proteins which are expressed by a mutant nucleic acid sequence which encodes for the protein. Typically, if a mutation in the nucleic acid results in a non conservative amino acid change in the protein relative to the wild-type (i.e. non-mutant nucleic acid) the protein can have a conformation change (i.e. not be in its native conformation) or misfolded. In some instances, misfolded polypeptides due to a non-conservative amino acid change can result in what is commonly known in the art as a "gain-of-function" where the misfolded polypeptide has a biological function different and/or in addition to the correctly folded polypeptide. The term a "gain of function mutation" refers to a genetic mutation where the mutant gene produces a protein which has extra capabilities relative to the wild type. Such different functions or extra capabilities, can be, for example, protein aggregation, abnormal subcellular localization, and other functions which do not occur with correctly folded (i.e. the native conformation) polypeptides. Examples are, for instance, amyloid proteins, as well as mutated proteins in neurodegenerative diseases, including but not limited to the mutated SOD1 or mutated TDP-43 genes in ALS, mutated genes which produce proteins in polyglutamine disorders, such as mutated huntingtin gene in Huntington's Disease and mutated beta-amyloid in Alzheimer's disease.

Without wishing to be bound by theory, Amyloids are insoluble fibrous protein aggregates sharing specific structural traits. Abnormal accumulation of amyloid in organs can lead to amyloidosis, and can play a role in various other neurodegenerative diseases. Diseases with amyloids include, but are not limited to Alzheimer's disease (Beta amyloid), Type 2 diabetes mellitus (IAPP), Parkinson's disease (Alpha-synuclein), Transmissible spongiform encephalopathy aka "Mad Cow Disease" (Prion), Huntington's Disease (Polyglutamine repeats), Medullary carcinoma of the thyroid (Calcitonin), Amyloidosis (Immunoglobulin), Sporadic Inclusion Body Myositis (S-IBM), pheochromocytoma and Osteomyelitis. Abnormal protein aggregation is also present in many neurodegenerative disorders, including AD, Parkinson's disease, Creutzfeldt-Jakob disease, motor neuron diseases such as ALS, a large group of polyglutamine disorders, including Huntington's disease, as well as diseases of peripheral tissue like familial amyloid polyneuropathy (FAP).

In one embodiment of this aspect and all other aspects described herein, a target antigen can be a protein involved in a disease or disorder. As used herein, a gene "involved" in a disease or disorder includes a gene, the normal or aberrant expression or function of which effects or causes the disease or disorder or at least one symptom of said disease or disorder. The term "gain-of-function mutation" as used herein, refers to any mutation in a gene in which the protein encoded by said gene (i e., the mutant protein) acquires a function not normally associated with the protein (i. e., the wild type protein) and causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

In one embodiment of this aspect and all other aspects described herein, a target antigen can be a protein expressed from a gene with a polymorphism. The term "polymorphism" as used herein, refers to a variation (e. g. , a deletion, insertion, or substitution) in a gene sequence that is identified or detected when the same gene sequence from different source subjects (but from the same organism) are compared. For example, a polymorphism can be identified when the same gene sequence from different subjects (but from the same organism) are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. A variation in sequence between two alleles of the same gene within an organism is referred to herein as an "allelic polymorphism". The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene.

In one embodiment of this aspect and all other aspects described herein, a target antigen can be a protein with a polyglutamine domain, or an expanded polyglutamine domain. The term "polyglutamine domain" as used herein, refers to a segment or domain of a protein that consist of a consecutive glutamine residues linked to peptide bonds. In one embodiment the consecutive region includes at least 5 glutamine residues. The term "expanded polyglutamine domain" or "expanded polyglutamine segment", as used herein, refers to a segment or domain of a protein that includes at least 35 consecutive glutamine residues linked by peptide bonds. Such expanded segments are found in subjects afflicted with a polyglutamine disorder, as described herein, whether or not the subject has shown to manifest symptoms. The term "trinucleotide repeat" or "trinucleotide repeat region" as used herein, refers to a segment of a nucleic acid sequence e. g.) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG, and/or CGG.

In one embodiment of this aspect and all other aspects described herein, a target antigen can be a protein expressed in a trinucleotide repeat disease. The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE Mental Retardation and myotonic dystrophy. Preferred trinucleotide repeat diseases for treatment according to the present invention are those characterized or caused by an expanded trinucleotide repeat region at the 5'end of the coding region of a gene, the gene encoding a mutant protein which causes or is causative of the disease or disorder.

In one embodiment of this aspect and all other aspects described herein, a target antigen is can be a protein expressed in a polyglutamine disorder. The term "polyglutamine disorder" as used herein, refers to any disease or disorder characterized by an expanded of a (CAG) n repeats at the 5'end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also know as Machado-Joseph disease), and spino-cerebellar ataxia type 6, spino-cerebellar ataxia type 7 and dentatorubral-pallidoluysian atrophy.

In one embodiment, a target antigen polypeptide is folded in its native conformation. In one embodiment, a target antigen polypeptide is part of a multi-molecular polypeptide complex. In one embodiment, a target antigen polypeptide is a subunit polypeptide of a multi-molecular polypeptide target antigen.

In some embodiments, a target antigen can be an intact (i.e. an entire or whole or complete) target antigen which is delivered to the cytosol of a cell by a non-linked or non-covalently linked LF polypeptide as described herein. By "intact" in this context is meant that the target antigen is the full length target antigen as that antigen polypeptide occurs in nature. This is in direct contrast to delivery of only a small portion or peptide of the target antigen. By delivering an intact target antigen to a cell, the LFn polypeptide enables or facilitates the translocation of the whole target antigen across the cell membrane and the display of a full range of epitopes of the intact target antigen in complexes with MHC I molecules. Moreover, this also facilitates detection of a cell mediated immune (CMI) response to a full range of epitopes of the intact target antigen, rather than just a single or selected few peptide epitopes. CMI occurs when T cells (lymphocytes) bind to the surface of other cells that display the antigen and trigger a response, e. g. production and release of cytokines. The response can involve other lymphocytes and any of the other white blood cells (leukocytes).

Accordingly, the use of an LFn polypeptide (which is non-linked or non-covalently linked to the intact antigen) in the methods and compositions described herein results in a stronger and more robust CMI response to the intact target antigen as compared to use of the intact target antigen alone or to a part (i.e. a peptide) of the target antigen, as a CMI response can be raised against essentially any epitope of the whole antigen.

In some embodiments, the intact target antigen can be divided into fragments, or parts, of the whole target antigen, for example, at least two, or at least 3, or at least 4, or a least 5 or more target antigen fragments, depending on size of the intact target antigen protein. These fragments of the whole target antigen can be used, for example, as a quality control to filter out false positives of a positive CMI response. By way of an example only, a positive CMI response to a whole target antigen can be confirmed by assessing a CMI response to a panel of target antigens which are fragments of the whole target antigen. A true CMI response is confirmed if one or two of the fragments give a positive response, but not all fragments. If a positive CMI response is detected for all fragments, it is likely that the positive CMI response was a false positive.

In some embodiments, an intact target antigen can be divided into many parts, depending on the size of the initial target antigen, for use as a panel of sub-target antigens. Typically, where a whole target antigen is a multimer polypeptide, the whole target protein can be divided into sub-units and/or domains which can each individually can be mixed with an LF polypeptide and used in assay methods and compositions as disclosed herein. Alternatively, an intact target antigen can be divided into fragments, or parts of the whole target antigen, for example, at least two, or at least 3, or at least 4, or at least 5, or at least 6, or at least 7, or at least 8, or at least about 9, or at least about 10, or at least about 11, or at least about 12, or at least about 13, or at least about 15, or at least about 20, or at least about 25, or more than 25 fragments, and each fragment, individually or in combination, mixed with an LF polypeptide for use in assay methods and compositions as disclosed herein.

The fragmentation or division of a full length target antigen polypeptide can be an equal division of the full length target antigen polypeptide, or alternatively, in some embodiments, the fragmentation is asymmetrical or unequal. As a non-limiting example, where a target antigen is divided into two overlapping fragments, a target antigen can be divided into fragments of approximately the same (equal) size, or alternatively one fragment can be about 45% of the whole target antigen and the other fragment can be about 65%. As further non-limiting examples, a whole target antigen can be divided into a combination of differently sized fragments, for example, where a target antigen is divided into two fragments, fragments can be divided into about 40% and about 70%, or about 45% and about 65%; or about 35% and about 75%; or about 25% and about 85% of the whole target antigen. Any combination of overlapping fragments of a full length whole target antigen is encompassed for use in the generation of a panel of target antigens. As an illustrative example only, where a target antigen is divided into 5 portions, the portions can be divided equally (i.e. each overlapping fragment is about 21 to 25% of the entire full length if the target antigen) or unequally (i.e. a target antigen can be divided into the following 5 overlapping fragments; fragment 1 is about 25%, fragment 2 is about 5%, fragment 3 is about 35%, fragment 4 is about 10% and fragment 5 is about 25% of the size of the full length target antigen, provided each fragment overlaps with at least one other fragment).

A target antigen which is a peptide, (i.e. a lengths of anywhere between 6 residues to 20 residues) can be delivered by a non-linked LF polypeptide. Polypeptides can also by synthesized as branched structures such as those disclosed in U.S. Pat. Nos. 5,229,490 and 5,390,111 which are incorporated herein by reference. Antigenic polypeptides include, for example, synthetic or recombinant B-cell and T-cell epitopes, universal T-cell epitopes, and mixed T-cell epitopes from one organism or disease and B-cell epitopes from another.

As noted above, target antigen can be obtained through recombinant means or peptide synthesis. Other sources include, natural sources or extracts. In any event, the antigen can be purified by means of the antigen's physical and chemical characteristics, preferably by fractionation or chromatography (Janson and Ryden, 1989; Deutscher, 1990; Scopes, 1993).

A multivalent target antigen formulation can be used to induce an immune response to more than one antigen at the same time. Conjugates can be used to induce an immune response to multiple antigens, to boost the immune response, or both. Additionally, toxins can be boosted by the use of toxoids, or toxoids boosted by the use of toxins.

In some embodiments, a target antigen can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Target antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous buffer for use in the present invention.

D. Additional Moieties and Adjuvants

In some embodiments, adjuvants in addition to the LF polypeptide can be included in the compositions as disclosed herein that comprise an LF polypeptide, such as an LFn polypeptide and a target antigen which is not covalently linked to the LFn polypeptide.

Adjuvants are a heterogeneous group of substances that enhance the immunological response against an antigen that is administered simultaneously. In some instances, adjuvants are added to a vaccine to improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens; and provide solubility to some vaccine components. Almost all adjuvants used today for enhancement of the immune response against antigens are particles or form particles together with the antigen. In the book "Vaccine Design—the subunit and adjuvant approach" (Ed: Powell & Newman, Plenum Press, 1995) almost all known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Typically adjuvants are particulate systems where the antigens are associated or mixed with or to a matrix, which has the characteristics of being slowly biodegradable. Adjuvants which are matrix systems should not degrade to form toxic metabolites. The main kinds of matrices that can be used are mainly substances originating from a body, including, for example lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

Adjuvants for vaccines are well known in the art. Suitable additional adjuvants include, but are not limited to: complete Freund's adjuvant, incomplete Freund's adjuvant, saponin, mineral gels such as aluminum hydroxide, surface active substances such as lysolecithin, pluronic polyols, polyaninons, peptides, oil or hydrocarbon emulsions, keyhole limpet hemocyanins, dinitrophenol, and potentially useful human adjuvants such as BCG (bacille Calmette-Guerin) and Corynebacterium parvum. Selection of an adjuvant depends on the animal subject to be vaccinated. Additional examples include, but are not limited to, monoglycerides and fatty acids(e. g. a mixture of mono-olein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagglutinin), ASO4 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array) and inert vehicles, such as gold particles. Newer adjuvants are described in U.S. Pat. No. 6,890,540, United States Patent Application No. 20050244420, and PCT/SE97/01003, the contents of which are incorporated herein by reference in their entirety. The adjuvant can also be selected from the group consisting of QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

It is preferred that any additional adjuvants be a pharmaceutically acceptable adjuvant. For example, oils or hydrocarbon emulsion adjuvants should not be used for human vaccination. One example of an adjuvant suitable for use with humans is alum (alumina gel). Details of common adjuvants which are contemplated to be added to the compositions of the present invention are discussed below:

Complete Freund's Adjuvant (CFA): A mineral oil adjuvant; uses a water-in-oil emulsion which is primarily oil. For many years the adjuvant of choice was complete Freund's adjuvant. This adjuvant, while potent immunogenically, also has had a significant history of frequently producing abscesses, granulomas and tissue sloughs. It contains paraffin oil, killed mycobacteria and mannide monoosleate. The paraffin oil is not metabolized; it is either expressed through the skin (via a granuloma or abscess) or phagocytized by macrophages. Multiple exposures to CFA will cause severe hypersensitivity reactions. Accidental exposure of personnel to CFA can result in sensitization to tuberculin.

Incomplete Freund's Adjuvant (IFA): Also a mineral oil adjuvant. Composition similar to CFA but does not contain the killed mycobacteria so does not produce as severe reactions. Used for the booster immunizations following the initial injection with antigen-CFA. IFA can be used for initial injection if the antigen is strongly immunogenic.

Montanide ISA (Incomplete Seppic Adjuvant): A mineral oil adjuvant. Uses mannide oleate as the major surfactant component. The antibody response is generally similar to that with IFA. Montanide ISA may have a lessened inflammatory response.

Ribi Adjuvant System (RAS): An oil-in-water emulsion that contains detoxified endotoxin and mycobacterial cell wall components in 2% squalene. Multiple formulations are commercially available, dependent on use. Is an alternative to CFA. Lower viscosity than CFA. Results (titers) often comparable to those with CFA. The squalene oil is metabolizable. RAS has a lower incidence of toxic reactions.

TiterMax: Another water-in-oil emulsion, this preperation combines a synthetic adjuvant and microparticulate silica with the metabolizable oil squalene. The copolymer is the immunomodulator component. Antigen is bound to the copolymer and presented to the immune cells in a highly concentrated form. Less toxicity than CFA. TiterMax usually produces the same results as CFA.

Syntex Adjuvant Formulation (SAF): A preformed oil-in-water emulsion. Uses a block copolymer for a surfactant. A muramyl dipeptide derivative is the immunostimulatory component. All in squalene, a metabolizable oil. SAF can bias the humoral response to IgG2a in the mouse, but is less toxic than CFA.

Aluminum Salt Adjuvants: Most frequently used as adjuvants for vaccine antigen delivery. Generally weaker adjuvants than emulsion adjuvants. Aluminum Salt Adjuvants are best used with strongly immunogenic antigens, but result generally in mild inflammatory reactions.

Nitrocellulose-adsorbed antigen: The nitrocellulose is basically inert, leading to almost no inflammatory response. Slow degradation of nitrocellulose paper allows prolonged release of antigen. Does not produce as dramatic an antibody response as CFA. Nitrocellulose-adsorbed antigen is good for use if only a small amount of antigen can be recovered from a gel band, e.g., for animal immunization.

Encapsulated or entrapped antigens: Permits prolonged release of antigen over time; can also have immunostimulators in preparation for prolonged release. Preparation of encapsulated or entrapped antigens is complex.

Immune-stimulating complexes (ISCOMs): Antigen modified saponin/cholesterol micelles. Stable structures are formed which rapidly migrate to draining lymph nodes. Both cell-mediated and humoral immune responses are achieved. Low toxicity; ISCOMs can elicit significant antibody response. Quil A is one example, QS-21 is another.

GerbuR adjuvant: An aqueous phase adjuvant which uses immunostimulators in combination with zinc proline. GerbuR does not have a depot effect and has minimal inflammatory effect. GerbuR requires frequent boosting to maintain high titers.

Alum is a preferred adjuvant. Another group of adjuvants include immune stimulators such as cytokines IL-12, IL-4 and costimulatory molecules such as B7. A wide range of molecules having immune stimulating effects are known including accessory molecules such as ICAM and LFA. In a preferred embodiment GM-CSF is administered to the patient before the initial immune administration. GM-CSF can be administered using a viral vector or an isolated protein in a pharmaceutical formulation. Combinations of adjuvants can be used such as CM-CSF, I CAM and LFA. While a strong immune response is typically generated to infectious disease antigens, tumor associated antigens typically generate a weaker immune response. Thus, immune stimulators such as described above are preferably used with them.

E. Methods to Assay for a CTL Response

In one embodiment of this aspect and all other aspects described herein, the delivery to a cell of a non-linked or non-covalently linked target antigen by an LF polypeptide can be assessed by measuring a CMI response to the target antigen. CMI assays are known in the art and described, for example, in United States Patent Application 20050014205, WO/1987/005400, U.S. Pat. No. 5,674,698 and commercially available kits such as IMMUNKNOW® CYLEX Immune cell function assay Product No. 4400, which are incorporated in their entirety by reference herein for use in the present invention.

F. Applications of an LFN Polypeptide with a Non-Linked or Non-Covalently Linked Target Antigen The immunogenic compositions of the present invention can be used to elicit a specific-immune response against the target antigen. In an alternative embodiment, an LF polypeptide, such as an LFn polypeptide or fragment thereof can be used to stabilize a target antigen which is unstable, without the need for being bound to the target antigen. For example, certain target antigens are difficult to express and/or are unstable and thus fold incorrectly to form a misfolded protein compared to its native active conformation. For such a protein, while still able to elicit a CMI response, the response will likely only be responsive to the improperly folded protein, and can not render any therapeutic and/or prophylactic benefit to the subject in which a CMI response is raised. While not wishing to be bound by theory, it is hypothesized that the presence of an LF polypeptide such as a polypeptide corresponding to SEQ ID NO: 3 or SEQ ID NO: 4 can stabilize certain such unstable target antigen proteins. The inventors have discovered that a fragment of LFn which is about at least 250 amino acids or less, or about at least 150 amino acids or less, or about at least 103 amino acids or less, or about at least 80 amino acids or less is able to stabilize unstable target antigens without needing to be fused to such target antigens. It is possible under this model that co-expression of non-linked LF polypeptide and target antigen can be benefical during the expression of the target antigen, or immediately after expression of the target antigen.

In some embodiments, the compositions as disclosed herein can be used to generate an immune response against the target antigen, such as for example use as a vaccine. An exemplary composition is a therapeutically effective amount of an LFn polypeptide (corresponding to SEQ ID NO: 3 or 4) or a fragment, homologue or variant thereof and a non-linked or non-covalently linked target antigen to induce an immune reaction. The composition acts as a prophylactic immunogen, optionally included in a pharmaceutically-acceptable and compatible carrier.

The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations can be used in preparing compositions incorporating the same ingredient to provide for variations in the age of the patient to be treated, the severity of the condition, the duration of the treatment and the mode of administration.

In one embodiment, the compositions as disclosed herein is a multicomponent vaccine which can comprise other immunogenic polypeptides, such as other adjuvants in addition to an LF polypeptide such as LFn or fragments thereof. A multicomponent vaccine can contain additional adjuvant(s) to elicit T cell responses, as well as other antigens and/or adjuvants to elicit B cell responses.

In some embodiments, the compositions are administered to a subject by a method of immunization, and in some embodiments, the method of immunization involves multiple administration regimens; e.g., a first administration to prime where the LFn can be used to deliver a non-linked or non-covalently linked target antigen; and then a second administration to "boost" the CMI using the LFn and a different novel non-linked or non-covalently linked target antigen.

In some embodiments, one can also use a composition comprising a cocktail of different LFn and non-linked or non-covalently linked target antigens to prime and boost with either a variety of different target antigens or with LFn in the presence of multiple target antigens.

In one embodiment of this aspect and all other aspects described herein, a pharmaceutical composition comprising an LF polypeptide and a target antigen can be used to generate a range of T cells that recognize and interact with a diverse range of antigens, for example, from different HIV strains. In some embodiments, the DNA sequence encoding the LF polypeptide and target antigen can also be used as a DNA-based vaccine. In trying to generate an immune reaction such as with a vaccine composition as disclosed herein, an adjuvant can also be used.

The immune stimulatory composition of the present invention can be used advantageously with other treatment regimens. For example, the system can be used in conjunction with traditional treatment options for cancer including surgery, radiation therapy, chemotherapy and hormone therapy. For example, a breast cancer vaccine (i.e. a composition) comprising an LF polypeptide and a non-linked or non-covalently linked target antigen can be used in conjunction with tamoxifen citrate, which interferes with the activity of estrogen. The system can also be combined with immunotherapy, e.g. using HERCEPTIN™ (trastuzumab), an anti-HER2 humanized monoclonal antibody developed to block the HER2 receptor; bone marrow transplantation; and peripheral blood stem cell therapy can also be used. Other preferred treatment regimens that can be used in conjunction with the compositions described herein include angiogenesis inhibitors and cytotoxic agents.

The term "compatible", as used herein, means that the components of the pharmaceutical compositions are capable of being commingled with each other, in a manner that does not substantially impair the desired pharmaceutical efficacy.

In one embodiment, the vaccine composition comprises an LF polypeptide such as LFn and a non-linked or non-covalently linked target antigen which is expressed and purified from insect cells. In one embodiment, the vaccine composition comprises a plurality of LF polypeptides such as LFn and a plurality of non-linked or non-covalently linked target antigens that are expressed and purified from insect cells, wherein the target antigen polypeptides are different but all are from a single intracellular pathogen. In one embodiment, the plurality of target antigen polypeptides are all from a single polypeptide from a single intracellular pathogen. In one embodiment, the vaccine composition comprises a plurality of LF polypeptides and a plurality of non-linked or non-covalently linked target antigens. In some embodiments, an LF polypeptide and a plurality of non-linked target antigens are expressed and purified from insect cells, wherein each target antigen polypeptide is different but all are from several intracellular pathogens. For example, a vaccine composition for raising a cell-mediated immune (CMI) response to mumps, measles and rubella viruses can have at least three different non-linked or non-covalently linked target antigens, each specific to mumps, measles and rubella viruses, respectively.

In another embodiment, the vaccine composition comprises an LF polypeptide such as LFn and a non-covalently linked target antigen, wherein the LFn polypeptide is N-glycosylated. The N-glycosylation can be at asparagine 62, 212 and/or 286 relative to the LFn of SEQ ID NO: 3 or SEQ ID NO: 4.

In some embodiments, the vaccine composition described herein further comprises pharmaceutical excipients including, but not limited to biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

In one embodiment, the invention provides a composition comprising an LF polypeptide such as LFn and a non-linked or non-covalently linked target antigen as described herein and an isolated mammalian cell. The isolated cell is preferably capable of processing and presenting target antigen fragments for display with MHC molecules. Such antigen-presenting cells can express MHC class I molecules only (so-called "non-professional" antigen presenting cells (APC'S)), or MHC Class I and class II molecules (so-called "professional" APC'S). Thus, in one embodiment, the mammalian cell is an antigen presenting cell, including a professional APC and/or a non-professional APC. Professional APC's include, e. g., macrophages, dendritic cells and B cells. In one embodiment, an LF polypeptide such as LFn and/or a non-linked or non-covalently linked target antigen can be expressed and purified from insect cells. In one embodiment, the mammalian cells are isolated from a subject who can have been exposed to a pathogen. Such a composition is useful in screening for exposure to pathogens, such as a CMI response assay or for a mass vaccination program. CMI assays are known in the art, for example, in United States Patent Application 20050014205, WO/1987/005400, U.S. Pat. No. 5,674,698 and commercially available kits such as IMMUNKNOW® CYLEX Immune cell function assay Product No. 4400.

G. Kits

Another aspect of the present invention relates to kits for producing a composition which is useful for eliciting a CMI against a desired target antigen, when the target antigen is not covalently linked to the LFn polypeptide. Such kits can be prepared from readily available materials and reagents. For example, such kits can comprise any one or more of the following materials: biologically active LFn, reaction tubes, instructions for testing LFn activity and reagents for addition of the user's preferred target antigen. A wide variety of kits and components can be prepared according to the present invention, depending upon the intended use of the kit, the particular target antigen and the needs of the user.

In an embodiment of such an aspect and all other aspects described herein, a kit comprises an LF polypeptide such as LFn as described herein and packaging materials therefor. In some embodiments, the kit also comprises a non-linked or non-covalently linked target antigen. Such a kit is useful in screening for exposure to pathogens, such as in a CMI response assay, or for a mass vaccination program. Packaging materials can include, but are not limited to adjuvants, diluents, alcohols wipes for disinfecting the site of injection, disposable fix volume syringes, dosage chart and immunization schedule.

In an embodiment of such an aspect and all other aspects described herein, a kit described herein comprises a plurality of LF polypeptides and a plurality of non-covalently linked target antigens. In one embodiment, individual members of the target antigens comprise different antigen polypeptides to a different portion of the same target antigen polypeptide.

A CMI assay is important for assessing both the exposure of a subject to a target antigen and a subject's ability to respond to an infection by a pathogenic agent such as a microorganism, virus or parasite, to mount an autoimmune response such as in diabetes or to protect against cancers or other oncological conditions. Consequently, reference to "measuring a CMI response to a target antigen in a subject" encompasses immune diagnosis of infectious and autoimmune diseases, a marker for immunocompetence and the detection of T-cell responses to endogenous and/or exogenous antigens (including a measure of the efficacy of a vaccine) as well as a marker for inflammatory diseases and cancer. Monitoring CMI pre- and post-transplantation is necessary in the management of organ transplant patients. A CMI assay can also be used to titrate initial immunosuppression reduction and its subsequent increase in these patients.

As discussed above, any of a range of target antigens can be tested such as those specific for a particular organism, pathogen, virus, auto-antigen or cancer cell. Alternatively, more general agents can be used to test generic capacity to mount a cell-mediated immune response. Examples of the latter include skin tests (e.g., PPD) from *M. tuberculosis* and tetanus toxoid. In general, however, any peptide, polypeptide or protein, glycoprotein, phosphoprotein, phospholipoprotein can be included in a non-linked or non-covalently linked from with an LF polypeptide in the compostion as described herein. These include antigens from pathogens, particularly, but not necessarily intracellular pathogens. The pathogens include, for example, any of the viral, bacterial, fungal or parasitic pathogens described herein, among others. The antigen can also include tumor antigens and/or autoimmune antigens.

H. Systems

In one aspect, provided herein is a system for measuring a cell mediated immune response (CMI) to a target antigen in a subject, the system comprising a computer processor and a computer-readable physical storage medium having instructions recorded thereon sufficient to implement a process, employing the computer processor, for measuring a cell-mediated immune response, the instructions for said process comprising:

a) instructions for receiving data regarding the level of at least one cytokine released in a biological sample in response to contacting a cell in said sample with at least one fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein said contacting permits transmembrane delivery of said target antigen to a said cell, which cell processes and displays at least one epitope of said antigen on its surface; and b) instructions for comparing the level of said at least one cytokine in said biological sample with a reference level of said at least one cytokine, c) instructions for transmitting to a user interface a result of said comparison, wherein an increase in the level of said at least one cytokine in said biological sample from the subject as compared to a reference level indicates a cell mediated immune response (CMI) to the target antigen in the subject.

In another aspect, provided herein is a computer-readable physical storage medium having instructions recorded thereon sufficient to implement a process, employing a computer processor, for measuring a cell-mediated immune response, the instructions for said process comprising:

a) instructions for receiving data regarding the level of at least one cytokine released in a biological sample, said data obtained by:

i) incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein said biological sample comprises cells of the immune system that release at least one cytokine in response to an antigen and wherein said incubating permits transmembrane delivery of said target antigen to a cell, which cell processes and displays epitopes of said antigen on its surface; and ii) measuring the level of at least one cytokine released in said biological sample;

b) instructions for comparing the level of said at least one cytokine in said biological sample with a reference level of said at least one cytokine, c) instructions for transmitting to a user interface a result of said comparison, wherein an increase in the level of said at least one cytokine in said biological sample from the subject as compared to a reference level indicates a cell mediated immune response (CMI) to the target antigen in the subject.

In another aspect, provided herein is a system for detecting a pathology of interest in a subject, the system comprising a computer processor a computer-readable physical storage medium having instructions recorded thereon sufficient to implement a process, employing the computer processor, for measuring a cell-mediated immune response, the instructions for said process comprising:

a) instructions for receiving data regarding the level of at least one cytokine released in a biological sample, said data obtained by a method comprising the steps of: incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein the target antigen is expressed in a tissue affected by the pathology, and wherein said biological sample comprises cells of the immune system that release at least one cytokine in response to an antigen; and measuring the level of at least one cytokine released in said biological sample; and b) instructions for comparing the level of said cytokine in said biological sample with a reference level of the same cytokine; and c) instructions for transmitting to a user interface a result of the comparison of (b), wherein an increase in the level of said at least one cytokine in said biological sample from the subject as compared to a reference level identifies the subject as having, or having an increased risk of having said pathology.

In another aspect, provided herein is a computer-readable physical storage medium having instructions recorded thereon sufficient to implement a process, employing a computer processor, for measuring a cell mediated immune response (CMI) to a target antigen in a subject, the instructions for said process comprising:

a) instructions for receiving data regarding the level of at least one cytokine released in a biological sample, said data obtained by a method comprising the steps of: i) incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein the target antigen is expressed in a tissue affected by the pathology, and wherein said biological sample comprises cells of the immune system that release at least one cytokine in response to an antigen; and ii) measuring the level of at least one cytokine released in said biological sample; and b) instructions for comparing the level of said cytokine in said biological sample with a reference level of the same cytokine; and c) instructions for transmitting to a user interface a result of the comparison of (b), wherein an increase in the level of said at least one cytokine in said biological sample from the subject as compared to a reference level identifies the subject as having, or having an increased risk of having said pathology.

Computer-readable physical storage media useful in various embodiments include any physical computer-readable storage medium, e.g., magnetic and optical computer-readable storage media, among others. Carrier waves and other signal-based storage or transmission media are not included within the scope of physical computer-readable storage media encompassed by the term and useful according to the invention.

A user interface useful in various embodiments includes, for example, a display screen or a printer or other means for providing a readout of the result of a computer-mediated process. A user interface can also include, for example, an address in a network or on the world wide web to which the results of a process are transmitted and made accessible to one or more users. For example, the user interface can include a graphical user interface comprising an access element that permits entry of data regarding cytokine release in a biological sample, as well as an access element that provides a graphical read out of the results of a comparison transmitted to or made available by a processor following execution of the instructions encoded on a computer-readable medium.

I. Compositions and Formulations

In some embodiments, the immunogenic compositions can be useful to elicit a specific antigen immune response against diseases such as influenza, and are useful either by inducing mucosal immunity or systemic immunity, or by a combination of immunity such as humoral, cellular or mucosal. Formulation is as described can be applied to single or multiple sites, to single or multiple limbs, or to large surface areas of the skin by complete immersion.

The LF polypeptides and compositions of the present invention are well suited for the preparation of pharmaceutical compositions. A pharmaceutical composition can be administered to any animal which can experience the beneficial effects of the compositions of the invention. Foremost among such animals are humans, although the invention is not intended to be so limited.

An LF polypeptide such as LFn and a non-linked or non-covalently bound covalent target antigen can be administered directly to a subject for treatment (including prophylactic and therapeutic)of a disease that expresses the target antigen. For example, in some embodiments, the compositions as disclosed herein comprising the LFn and at least one non-linked or non-covalently linked target antigen can be used to elicit an CMI against the target antigen. In some embodiments, the compositions as disclosed herein comprising an LFn polypeptide and at least one non-linked or non-covalently linked target antigen can be used for the inhibition of cancer, tumor, or precancerous cells in vivo. Administration is by any of the routes normally used for introducing a compound into ultimate contact with the tissue or cells to be acted upon. The compounds are administered in any suitable manner, preferably with pharmaceutically acceptable carriers. Suitable methods of administering such composition are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17th ed. 1985)).

Formulations:

The compositions as disclosed herein comprising an LF polypeptide, such as LFn, and a non-linked or non-covalently linked target antigen can be administered per se (neat) or in the form of a pharmaceutically acceptable salt. When used in medicine, the salts should be pharmaceutically acceptable, but non-pharmaceutically acceptable salts can conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulfonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

In some embodiments, the compositions comprising an LF polypeptide and a target antigen as described herein can conveniently be presented in unit dosage form and can be prepared by any of the methods well known in the art of pharmacy. Methods typically include the step of bringing the active ingredients of the invention into association with a carrier which constitutes one or more accessory ingredients.

Preferred compositions suitable for parenteral administration conveniently comprise a sterile aqueous preparation which is preferably isotonic with the blood of the recipient. This aqueous preparation can be formulated according to known methods using those suitable dispersing or wetting agents and suspending agents. The sterile injectable preparation can also be a sterile injectable solution or suspension in a non-toxic parenterally-acceptable diluent or solvent, for example as a solution in 1,3-butane diol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Administration:

Formulations suitable for parenteral administration, such as, for example, by intravenous, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

In some embodiments, compositions as described herein can be administered by any means that achieve their intended purpose. For example, administration can be by parenteral, subcutaneous, intravenous, intradermal, intramuscular, intraperitoneal, transdermal, or buccal routes. Alternatively, or concurrently, administration can be by the oral route. The proteins and pharmaceutical compositions can be administered parenterally by bolus injection or by gradual perfusion over time. Alternatively, a composition can include those suitable for oral, rectal, intravaginal, topical, nasal, ophthalmic or parenteral administration, all of which can be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques. Intramuscular administration is preferred.

In some embodiments, compositions comprising an LF polypeptide, such as LFn and a non-linked or non-covalently linked target antigen, either alone or in combination with other suitable components (e.g., other adjuvants and/or carriers) can be made into aerosol formulations (i.e., they can be "nebulized") to be administered via inhalation. Aerosol formulations can be placed into pressurized acceptable propellants, such as dichlorodifluoromethane, propane, nitrogen, and the like, or non-pressurized acceptable propellants such as an spray pump, or similar devices (asthma inhaler) which can be used for oral and/or aerosol administration of the compositions as disclosed herein.

In alternative embodiments, compositions comprising an LF polypeptide and a target antigen can be formulated to be suitable for oral administration, and can be presented as discrete units such as capsules, cachets, tablets or lozenges, each containing a predetermined amount of the LF polypeptide and a target antigen as discussed herein. In some embodiments, an LF polypeptide and target antigen can be formulated as liposomes or as a suspension in an aqueous liquor or non-aqueous liquid such as a syrup, an elixir, or an emulsion.

In some embodiments, the immunogenic compositions can be useful to elicit a specific antigen immune response against diseases such as influenza, and are useful either by inducing mucosal immunity or by inducing systemic immunity, or by a combination of immunity such as humoral, cellular or mucosal.

Preparations which can be administered orally in the form of tablets and capsules, preparations which can be administered rectally, such as suppositories, and preparations in the form of solutions for injection or oral introduction, contain about a 0.001 to about 99 percent, preferably from about 0.01 to about 95 percent of active compound(s), together with the excipient.

Suitable excipients are, in particular, fillers such as saccharides, for example lactose or sucrose, mannitol or sorbitol cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers can be added.

Possible pharmaceutical preparations which can be used rectally include, for example, suppositories, which consist of a combination of one or more of the active compositions with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the proteins in water-soluble form, for example, water-soluble salts. In addition, suspensions of the proteins as appropriate oil injection suspensions can be administered. Suitable lipophilic solvents or vehicles include fatty oils, for example, sesame oil, or synthetic fatty acid esters, for example, ethyl oleate or triglycerides. Aqueous injection suspensions containing substances which increase the viscosity of the suspension include, for example, sodium carboxymethyl cellulose, sorbitol, and/or dextran. Optionally, the suspension can also contain stabilizers.

The proteins are formulated using conventional pharmaceutically acceptable parenteral vehicles for administration by injection. These vehicles are nontoxic and therapeutic, and a number of formulations are set forth in Remington's Pharmaceutical Sciences, (supra). Nonlimiting examples of excipients are water, saline, Ringer's solution, dextrose solution and Hank's balanced salt solution. Formulations according to the invention can also contain minor amounts of additives such as substances that maintain isotonicity, physiological pH, and stability.

In some embodiments, a composition comprising an LF polypeptide such as an LFn polypeptide and a non-linked or non-covalently linked target antigen are formulated in purified form substantially free of aggregates and other protein materials, preferably at concentrations of about 1.0 ng/ml to 100 mg/ml.

Doses:

The dose administered to a patient, in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient Doses of the pharmaceutical compositions described herein will vary depending on the subject and upon the particular route of administration used. Generally, for prophylactic vaccination, dosages will range from 1 ng to 300 μg of target antigen/LF polypeptide combination. The proportion of target antigen to LF polypeptide can also vary. E.g., from 0.01 target antigen: 1 LF polypeptide (i.e., 100:1 LF to target antigen ratio) to 1 target antigen: 0.01 LF polypeptide (e.g., 100:1 target antigen to LF polypeptide) and all values inbetween. To the extent that LF polypeptide may form a complex with the target antigen even when not covalently bound to it, it is contemplated that higher ratios of LF polypeptide to target antigen may be beneficial. Thus, for example, a 100:1 LF polypeptide to target antigen ratio may be preferable to lower ratios, such as 10:1, 1:1 or 0.1:1 of LF polypeptide to target antigen ratio.

Preferred doses of the compositions are preferably at least 2 μg/ml. By way of an example only, an overall dose range of from about, for example, 1 nanogram to about 300 micrograms might be used for human use. This dose can be delivered at periodic intervals based upon the composition. For example on at least two separate occasions, preferably spaced apart by about 4 weeks. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at 1442-43. (e.g., Hepatitis B Vaccine-type protocol); (ii) for example with other vaccines the recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, *Physician's Desk Reference*, Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

The dosage administered will be dependent upon the age, sex, health, and weight of the recipient, kind of concurrent treatment, if any, frequency of treatment, and the nature of the effect desired. Where vaccination is for therapeutic purposes, e.g. for treatment of cancer and other existing diseases or disorders, the dose ranges for the administration of the compositions described herein are those large enough to produce the desired effect, whereby, for example, an immune response to the proteins as measured by delayed-type hypersensitivity (DTH), T-cell activation or antibody production, is achieved, and the disease is substantially suppressed or treated. The doses should not be so large as to cause adverse side effects, such as unwanted cross reactions, anaphylactic reactions and the like. In some embodiments, a dose for humans ranges between about 0.001-1 mg/kg body weight. Effective doses of a composition comprising an LF polypeptide such as an LFn polypeptide and a non-linked or non-covalently linked target antigen for use in preventing, suppressing, or treating a non-infectious disease can be in the range of about 1 ng to 100 mg/kg body weight. A preferred dose range is between about 10 ng and 10 mg/kg. A more preferred dose range is between about 100 ng and 1 mg/kg.

In some embodiments, administration can be accomplished via single or divided doses, for example, for injectable immunizations that induce immunity but have potential side effects upon boosting, a transcutaneous boost can be preferable, or oral or nasal immunization can be used to "boost" an immune response against the target antigen. In some embodiments, simultaneous use of injectable and transcutaneous immunizations could also be used.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding it will be readily apparent to one of ordinary skill in the art in light of the teachings herein that certain changes and modifications can be made thereto without departing from the spirit or scope of the appended claims.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention can be performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Baculovirus Expression Protocols (Methods in Molecular Biology, Vol 39) by Christopher D. Richardson (Editor); Hardcover—450 pages Spiral edition (March 1998) Humana Pr; ISBN: 0896032728; Baculovirus Expression Vectors: A Laboratory Manual by David R. O'Reilly, Lois Miller, Verne A. Luckow; Paperback Spiral edition (June 1994) Oxford Univ Press; ISBN: 0195091310; The Baculovirus Expression System : A Laboratory Guide by Linda A. King, R. D. Possee; Hardcover (May 1992) Chapman & Hall; ISBN: 0412371502, which are all incorporated by reference herein in their entireties.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

In some embodiments of the present invention may be defined in any of the following numbered paragraphs:

1. A composition for promoting a cell mediated immune (CMI) response to a target antigen, the composition comprising at least one isolated target antigen and a portion of a Lethal Factor (LF) polypeptide lacking LF enzymatic activity, wherein the portion of an LF polypeptide is not covalently linked to the target antigen, and wherein the composition does not comprise a protective antigen (PA) of an exotoxin bipartite protein.
2. The composition of paragraph 1, wherein said portion of an LF polypeptide comprises at least the 60 carboxy-terminal amino acids of SEQ ID NO: 3, or a conservative substitution variant thereof that promotes a CMI response to the target antigen.
3. The composition of paragraph 1, wherein said portion of an LF polypeptide comprises at least the 80 carboxy-terminal amino acids of SEQ ID NO: 3, or a conservative substitution variant thereof that promotes a CMI response to the target antigen.
4. The composition of any one of paragraphs 1 to 3, wherein said portion of an LF polypeptide comprises at least the 104 carboxy-terminal amino acids of SEQ ID NO: 3, or a conservative substitution variant thereof that promotes a CMI response to the target antigen.
5. The composition of any of paragraphs 1 to 4, wherein the portion of an LF polypeptide comprises the amino acid sequence corresponding to SEQ ID NO: 3 or a conservative substitution variant thereof that promotes a CMI response to the target antigen.
6. The composition of any one of paragraphs 1 to 5, wherein said portion of an LF polypeptide does not bind PA polypeptide.
7. The composition of any one of paragraphs 1 to 6, wherein said portion of an LF polypeptide substantially lacks amino acids 1-33 of SEQ ID NO: 3.
8. The composition of any one of paragraphs 1 to 3, wherein said portion of an LF polypeptide consists of SEQ ID NO: 4, or a conservative substitution variant thereof that promotes a CMI response to the target antigen.
9. The composition of any one of paragraphs 1 to 3, wherein said portion of an LF polypeptide consists of SEQ ID NO: 5.
10. The composition of paragraph 1, wherein the cell is in vivo or present in an organism.
11. The composition of paragraph 1, wherein the cell is in vitro.
12. The composition of paragraph 1 which induces a response by a cell against a target antigen, when said cell is contacted with the composition in the presence of the target antigen, and in the absence of an exotoxin protective antigen (PA).
13. The composition of paragraph 1, wherein the target antigen is selected from the group consisting of pathogen antigen, a tumor antigen or a endogenous misfolded protein.
14. The composition of paragraph 13, wherein the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.
15. The composition of paragraph 13 or 14, wherein the pathogen antigen is not an antigen expressed by *B. anthracis*.
16. The composition of paragraph 1, wherein the composition optionally comprises at least one adjuvant.
17. The composition of paragraph 16, wherein the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.
18. A method of promotiong a cell-mediated immune response to a cell, the method comprising contacting said cell with a target antigen in the presence of a portion of a *B. anthracis* LF polypeptide lacking LF enzymatic activity, wherein the portion of a *B. anthracis* LF polypeptide lacking LF enzymatic activity is not covalently linked to the target antigen, and wherein said cell is not contacted with a protective antigen (PA) of an exotoxin bipartite protein, whereby a cell-mediated immune response to the target antigen is promoted.

19. A composition for delivering a target antigen to a cell, the composition comprising at least one target antigen and a portion of a *B. anthracis* LF polypeptide lacking LF enzymatic activity, wherein the portion of a *B. anthracis* LF polypeptide is not covalently linked to the target antigen, and wherein the composition does not comprise a protective antigen of *B. anthracis* exotoxin bipartite protein.

20. The composition of paragraph 19, wherein said portion of a *B. anthracis* LF polypeptide comprises at least the 60 carboxy-terminal amino acids of SEQ ID NO: 3, or a conservative substitution variant thereof that promotes transmembrane delivery.

21. The composition of paragraph 19, wherein said portion of a *B. anthracis* LF polypeptide comprises at least the 80 carboxy-terminal amino acids of SEQ ID NO: 3, or a conservative substitution variant thereof that promotes transmembrane delivery.

22. The composition of any one of paragraphs 19-21, wherein said portion of a *B. anthracis* LF polypeptide comprises at least the 104 carboxy-terminal amino acids of SEQ ID NO: 3, or a conservative substitution variant thereof that promotes transmembrane delivery.

23. The composition of any of paragraphs 19-22, wherein the portion of a *B. anthracis* LF polypeptide comprises the amino acid sequence corresponding to SEQ ID NO: 3 or a conservative substitution variant thereof that promotes transmembrane delivery.

24. The composition of any one of paragraphs 19-23, wherein said portion of a *B. anthracis* LF polypeptide does not bind *B. anthracis* PA polypeptide.

25. The composition of any one of paragraphs 19-24, wherein said portion of a *B. anthracis* LF polypeptide substantially lacks amino acids 1-33 of SEQ ID NO: 3.

26. The composition of any one of paragraphs 19-21, wherein said portion of a *B. anthracis* LF polypeptide consists of SEQ ID NO: 4, or a conservative substitution variant thereof that promotes transmembrane delivery.

27. The composition of any one of paragraphs 19-21, wherein said portion of a *B. anthracis* LF polypeptide consists of SEQ ID NO: 5.

28. The composition of paragraph 19, wherein the cell is in vivo or present in an organism.

29. The composition of paragraph 19, wherein the cell is in vitro.

30. The composition of paragraph 19 which induces a response by a cell against a target antigen, when said cell is contacted with the composition in the presence of the target antigen, and in the absence of an exotoxin protective antigen (PA).

31. The composition of paragraph 19, wherein the target antigen is selected from the group consisting of pathogen antigen, a tumor antigen or a endogenous misfolded protein.

32. The composition of paragraph 31, wherein the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

33. The composition of paragraph 31 or 32, wherein the pathogen antigen is not an antigen expressed by *B. anthracis.*

34. The composition of paragraph 19, wherein the composition optionally comprises at least one adjuvant.

35. The composition of paragraph 34, wherein the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.

36. A method of delivering a target antigen to the cytosol of a cell, the method comprising contacting said cell with a target antigen in the presence of a portion of a *B. anthracis* LF polypeptide lacking LF enzymatic activity, wherein the portion of a *B. anthracis* LF polypeptide lacking LF enzymatic activity is not covalently linked to the target antigen, and wherein said cell is not contacted with a protective antigen (PA) of an exotoxin bipartite protein, whereby the target antigen is delivered to the cytosol of the cell.

37. A method of paragraph 36, wherein the delivery of said target antigen induces a cell-mediated immune (CMI) response to said target antigen by said cell.

38. The method of paragraph 36, wherein said portion of an LF polypeptide corresponds to SEQ ID NO: 5 or a functional fragment thereof.

39. The method of paragraph 36, wherein said portion of a *B. anthracis* LF polypeptide comprises at least the 60 carboxy-terminal amino acids of SEQ ID NO: 3, or a conservative substitution variant thereof that promotes transmembrane delivery.

40. The method of paragraph 36, wherein said portion of a *B. anthracis* LF polypeptide comprises at least the 80 carboxy-terminal amino acids of SEQ ID NO: 3, or a conservative substitution variant thereof that promotes transmembrane delivery.

41. The method of paragraph 36, wherein said portion of a *B. anthracis* LF polypeptide comprises at least the 104 carboxy-terminal amino acids of SEQ ID NO: 3, or a conservative substitution variant thereof that promotes transmembrane delivery.

42. The method of paragraph 36, wherein the portion of a *B. anthracis* LF polypeptide comprises the amino acid sequence corresponding to SEQ ID NO: 3 or a conservative substitution variant thereof that promotes transmembrane delivery.

43. The method of paragraph 36, wherein said portion of a *B. anthracis* LF polypeptide does not bind B. anthracis PA polypeptide.

44. The method of paragraph 36, wherein said portion of a *B. anthracis* LF polypeptide substantially lacks amino acids 1-33 of SEQ ID NO: 3.

45. The method of paragraph 36, wherein said portion of a *B. anthracis* LF polypeptide consists of SEQ ID NO: 4, or a conservative substitution variant thereof that promotes transmembrane delivery.

46. The method of paragraph 36, wherein said portion of a *B. anthracis* LF polypeptide consists of SEQ ID NO: 5.

47. The method of paragraph 36, wherein the exotoxin is *B. anthracis.*

48. The method of paragraph 36, wherein the cell is in vivo or present in an organism.

49. The method of paragraph 36, wherein the cell is in vitro.
50. The method of paragraph 36, further comprising administering to the cell at least one other adjuvant, wherein the adjuvant does not comprise SEQ ID NO: 3 or SEQ ID NO: 4.
51. The method of paragraph 50, wherein the adjuvant is selected from a group comprising of; complete Freud's Adjuvant, Incomplete Freud's Adjuvant, CM-CSF, QS21, CpG, RIBI Detox, of; IL-2, Ig-IL-2, B7, ICAM, LFS, dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.
52. The method of paragraph 36, wherein the target antigen is selected from the group consisting of pathogen antigen, a tumor antigen or a endogenous misfolded protein.
53. The method of paragraph 52, wherein the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.
54. The method of paragraph 52, wherein the pathogen antigen is not an antigen expressed by *B. anthracis*.
55. The use of a composition of paragraph 1 to induce a cell mediated response against a target antigen by a cell, wherein the cell is contacted with the composition in the presence of the target antigen, and in the absence of an exotoxin protective antigen (PA).
56. The composition of paragraphs 1 or 19, further comprising at least one additional immune adjuvant.
57. The composition of paragraph 56, wherein the immune adjuvant is selected from the group consisting of; Alum, Complete Freud's Adjuvant, Incomplete Freud's Adjuvant, CM-CSF, QS21, CpG, RIBI Detox.
58. The composition of paragraph 56, wherein the immune adjuvant is a cytokine selected from the group consisting of; IL-2, Ig-IL-2.
59. The composition of paragraph 56, wherein the immune adjuvant is a co-stimulatory molecule selected from the group consisting of; B7, ICAM, LFS.

The composition of paragraph 56, wherein the immune adjuvant is a non-antigenic polymeric substance selected from the group consisting of; dextran, polyvinyl pyrrolidones, polysaccharides, starches, polyvinyl alcohols, polyacryl amides, polyethylene glycol(PEG), poly(alkylenes oxides), monomethoxy-polyethylene glycol polypropylene glycol, block copolymers of polyethylene glycol, polypropylene glycol.

61. The method of any of the above paragraphs, wherein SEQ ID NO: 3 or SEQ ID NO: 4 is codon optimized for production in bacterial cells.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The contents of all references cited throughout this application, as well as the figures and tables therein are incorporated herein by reference.

REFERENCES

1. Anderson, K. S., J. Alexander, M. Wei, and P. Cresswell 1993. Intracellular transport of class I MHC molecules in antigen processing mutant cell lines Journal of Immunology. 151:3407-19.

2. Androlewicz, M. J., K. S. Anderson, and P. Cresswell 1993. Evidence that transporters associated with antigen processing translocate a major histocompatibility complex class I-binding peptide into the endoplasmic reticulum in an ATP-dependent manner Proceedings of the National Academy of Sciences of the United States of America. 90:9130-4.

3. Ballard, J. D., A. M. Doling, K. Beauregard, R. J. Collier, and M. N. Starnbach 1998. Anthrax toxin-mediated delivery in vivo and in vitro of a cytotoxic T-lymphocyte epitope from ovalbumin Infection & Immunity. 66:615-9.

4. Borrow, P., H. Lewicki, B. H. Hahn, G. M. Shaw, and M. B. A. Oldstone 1994. Virus-specific CD8+ cytotoxic T-lymphocyte activity associated with control of viremia in primary human immunodeficiency virus type 1 infection J. Virol. 68:6103-6110.

5. Borrow, P., H. Lewicki, X. Wei, M. S. Horwitz, N. Peffer, H. Meyers, J. A. Nelson, J. E. Gairin, B. Hahn, M. B. Oldstone, and G. M. Shaw 1997. Antiviral pressure exerted by HIV-1-specific cytotoxic T lymphocytes (CTLs) during primary infection demonstrated by rapid selection of CTL escape virus Nature Medicine. 3:205-211.

6. Cao, H., P. Kanki, J.-L. Sankale, A. Dieng-Sarr, G. P. Mazzara, S. A. Kalams, B. Korber, S. MBoup, and B. D. Walker 1997. Cytotoxic T-lymphocyte cross-reactivity among different human immunodeficiency virus type 1 clades: implication for vaccine development J. Virol. 71:8615-23.

7. Cao, H., I. Mani, R. Vincent, R. Mugerwa, P. Mugyenyi, P. Kanki, J. Ellner, and B. D. Walker 2000. Cellular immunity to HIV-1 Clades: relevance to HIV-1 vaccine trials in Uganda J. Infec Dis. 182:1350-56.

8. Doling, A. M., J. D. Ballard, H. Shen, K. M. Krishna, R. Ahmed, R. J. Collier, and M. N. Starnbach 1999. Cytotoxic T-lymphocyte epitopes fused to anthrax toxin induce protective antiviral immunity Infection & Immunity. 67:3290-6.

9. Falk, K., O. Rotzchke, K. Deres, J. Metzger, G. Jung, and H.-G. Rammensee 1991. Identification of naturally processed viral nonapeptides allows their quantification in infected cells and suggests an allele-specific T cell epitope forecast. J. Exp. Med. 174:425-434.

10. Finbloom, D. S., J. Martin, and R. K. Gordon 1987. Endocytosis of particulate and soluble IgG immune complexes: differential effects of cytoskeletal modulating agents Clinical & Experimental Immunology. 67:205-10.

11. Geisow, M. J., P. D'Arcy Hart, and M. R. Young 1981. Temporal changes of lysosome and phagosome pH during phagolysosome formation in macrophages: studies by fluorescence spectroscopy Journal of Cell Biology. 89:645-52.

12. Goldberg, A. L., and K. L. Rock 1992. Proteolysis, proteasomes and antigen presentation Nature. 357:375-9.

13. Hanna, P. C., D. Acosta, and R. J. Collier 1993. On the role of macrophages in anthrax Proceedings of the National Academy of Sciences of the United States of America. 90:10198-201.

14. Harding, C. V., and R. Song 1994. Phagocytic processing of exogenous particulate antigens by macrophages for presentation by class I MHC molecules Journal of Immunology. 153:4925-33.

15. Howard, J. C. 1995. Supply and transport of peptides presented by class I MHC molecules Current Opinion in Immunology. 7:69-76.

16. Klaus, G. G. 1973. Cytochalasin B. Dissociation of pinocytosis and phagocytosis by peritoneal macrophages Experimental Eye Research. 79:73-8.

17. Koup, R. A., J. T. Safrit, Y. Cao, C. A. Andrews, G. McLeod, W. Borkowsky, C. Farthing, and D. D. Ho 1994. Temporal association of cellular immune responses with the initial control of viremia in primary human immunodeficiency virus type 1 syndrome J. Virol. 68:4650-4655.

18. Lalvani, A., R. Brookes, S. Hambleton, W. J. Britton, A. V. Hill, and A. J. McMichael 1997. Rapid effector function in CD8+ memory T cells Journal of Experimental Medicine. 186:859-65.

19. Lu, Y., R. Friedman, N. Kushner, A. Doling, L. Thomas, N. Touzjian, M. Starnbach, and J. Lieberman 2000. Genetically modified anthrax lethal toxin safely delivers whole HIV protein antigens into the cytosol to induce T cell immunity Proceedings of the National Academy of Sciences of the United States of America. 97:8027-32.

20. Man, S., R. D. Salter, and V. H. Engelhard 1992. Role of endogenous peptide in human alloreactive cytotoxic T cell responses International Immunology. 4:367-75.

21. Neefjes, J., F. Momberg, and G. Hammerling 1993. Selective and ATP-dependent translocation of peptides by the MHC-encoded transporter. Science. 261:769-771.

22. Ogg, G. S., X. Jin, S. Bonhoeffer, P. R. Dunbar, M. A. Nowak, S. Monard, J. P. Segal, Y. Cao, S. L. Rowland-Jones, v. Cerundolo, A. Hurley, M. Markowitz, D. D. Ho, D. F. Nixon, and A. J. McMichael 1998. Quantitation of HIV-1-specific cytotoxic T lymphocytes and plasma load of viral RNA Science. 279:2103-6.

23. Ohkuma, S., and B. Poole 1978. Fluorescence probe measurement of the intralysosomal pH in living cells and the perturbation of pH by various agents Proceedings of the National Academy of Sciences of the United States of America. 75:3327-31.

24. Ortmann, B., M. J. Androlewicz, and P. Cresswell 1994. MHC class I/beta 2-microglobulin complexes associate with TAP transporters before peptide binding Nature. 368:864-7.

25. Pfeifer, J. D., M. J. Wick, R. L. Roberts, K. Findlay, S. J. Normark, and C. V. Harding 1993. Phagocytic processing of bacterial antigens for class I MHC presentation to T cells Nature. 361:359-62.

26. Pinto, L. A., J. Sullivan, J. A. Berzofsky, M. Clerici, H. A. Kessler, A. L. Landay, and G. M. Shearer 1995. ENV-specific cytotoxic T lymphocyte responses in HIV seronegative health care workers occupationally exposed to HIV-contaminated body fluids J. Clin. Invest. 96:867-76.

27. Powis, S. J. 1997. Major histocompatibility complex class I molecules interact with both subunits of the transporter associated with antigen processing, TAP1 and TAP2 European Journal of Immunology. 27:2744-7.

28. Rowland-Jones, S., J. Sutton, K. Ariyoshi, T. Dong, F. Gotch, S. McAdam, D. Whitby, S. Sabally, A. Gallimore, T. Corrah, M. Takiguchi, T. Schultz, A. McMichael, and H. Whittle 1994. Resistance to HIV-1 infection-HIV-specific cytotoxic T lymphocytes in HIV-exposed but uninfected Gambian women Nature Medicine. in Press.

29. Sadasivan, B., P. J. Lehner, B. Ortmann, T. Spies, and P. Cresswell 1996. Roles for calreticulin and a novel glycoprotein, tapasin, in the interaction of MHC class I molecules with TAP Immunity. 5:103-14.

30. Solheim, J. C., M. R. Harris, C. S. Kindle, and T. H. Hansen 1997. Prominence of beta 2-microglobulin, class I heavy chain conformation, and tapasin in the interactions of class I heavy chain with calreticulin and the transporter associated with antigen processing Journal of Immunology. 158:2236-41.

31. Song, R., and C. V. Harding 1996. Roles of proteasomes, transporter for antigen presentation (TAP), and beta 2-microglobulin in the processing of bacterial or particulate antigens via an alternate class I MHC processing pathway Journal of Immunology. 156:4182-90.

32. Suh, W. K., M. F. Cohen-Doyle, K. Fruh, K. Wang, P. A. Peterson, and D. B. Williams 1994. Interaction of MHC class I molecules with the transporter associated with antigen processing Science. 264:1322-6.

33. Wei, M. L., and P. Cresswell 1992. HLA-A2 molecules in an antigen-processing mutant cell contain signal sequence-derived peptides. Nature. 356:443-6.

34. Yewdell, J. W., and J. R. Bennink 1989. Brefeldin A specifically inhibits presentation of protein antigens to cytotoxic T lymphocytes Science. 244:1072-5.

All references described herein are incorporated herein by reference.

The invention claimed is:

1. A composition for promoting a cell mediated immune (CMI) response to a target antigen, the composition comprising at least one isolated target antigen and a portion of a Lethal Factor (LF) polypeptide lacking LF enzymatic activity, wherein the portion of an LF polypeptide consists of SEQ ID NO: 4 or SEQ ID NO: 5, or a conservative substitution variant of SEQ ID NO: 4 or SEQ ID NO: 5 that promotes a CMI response to the target antigen, wherein the LF polypeptide is not physically linked to the target antigen, and wherein the composition does not comprise a protective antigen (PA) of an exotoxin bipartite protein, and wherein the LF polypeptide is glycosylated, or the target antigen and LF polypeptide are glycosylated.

2. The composition of claim 1, wherein the cell mediated immune response is in vivo or present in an organism or in vitro.

3. The composition of claim 1, wherein the target antigen is selected from the group consisting of: a pathogen antigen, a tumor antigen or an endogenous misfolded protein.

4. The composition of claim 3, wherein the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

5. The composition of claim 1, wherein the composition optionally comprises at least one adjuvant.

6. The composition of claim 5, wherein the adjuvant is selected from a group consisting of: Alum; complete Freud's Adjuvant Incomplete Freud's Adjuvant GM-CSF; QS21; CpG; RIBI Detox; IL-2; Ig-IL-2; B7; ICAM; LFS; dextran; polyvinyl pyrrolidones; polysaccharides; starches; polyvinyl alcohols; polyacryl amides; polyethylene glycol(PEG); poly (alkylenes oxides); monomethoxy-polyethylene glycol polypropylene glycol; block copolymers of polyethylene glycol; polypropylene glycol.

7. A composition for delivering a target antigen to a cell, the composition comprising two separate components wherein at least one of the separate components is glycosylated, a first component comprising at least one target antigen and a second component comprising a portion of a *B. anthracis* LF polypeptide lacking LF enzymatic activity and consists of SEQ ID NO: 4 or SEQ ID NO: 5, or a conservative substitution variant of SEQ ID NO: 4 or SEQ ID NO: 5 that promotes a CMI response to the target antigen, wherein the first component is not physically linked to the second component, and wherein the composition does not comprise a protective antigen of *B. anthracis* exotoxin bipartite protein.

8. The composition of claim 7, wherein the cell is in vivo or present in an organism or in vitro.

9. The composition of claim 7, wherein the target antigen is selected from the group consisting of pathogen antigen, a tumor antigen or a endogenous misfolded protein.

10. The composition of claim 9, wherein the pathogen antigen is selected from the group consisting of: Hepatitis A, Hepatitis B, Hepatitis C, Avian flu virus, ebola virus, west nile virus, influenza virus, Herpes Simplex Virus 1, Herpes Simplex Virus2, HIV2, HIV1 and other HIV1 strains.

11. The composition of claim 7, wherein the composition optionally comprises at least one adjuvant.

12. The composition of claim 11, wherein the adjuvant is selected from a group consisting of: Alum; complete Freud's Adjuvant; Incomplete Freud's Adjuvant; GM-CSF; QS21; CpG; RIBI Detox; IL-2; Ig-IL-2; B7; ICAM; LFS; dextran; polyvinyl pyrrolidones; polysaccharides; starches; polyvinyl alcohols; polyacryl amides; polyethylene glycol(PEG); poly (alkylenes oxides); monomethoxy-polyethylene glycol polypropylene glycol; block copolymers of polyethylene glycol; polypropylene glycol.

13. The composition method of claim 3, wherein the pathogen antigen is a tuberculosis antigen.

14. The composition method of claim 13, wherein the tuberculosis antigen is selected from at least one from the group consisting of:381; Mtb32A; Mtb16; Mtb72f; Mtb59f; Mtb88f; Mtb71f; Mtb46f and Mtb31f; TbH9 (Mtb 39A); TB1 (CFP); or TB2 (ESAT) or fragments thereof.

15. The composition of claim 1, wherein the LF polypeptide is N-glycosylated or O-glycosylated.

16. The composition of claim 1, wherein the target antigen is N-glycosylated or O-glycosylated.

17. The composition of claim 15, where the LF polypeptide is glycosylated on at least one residue selected from residues 62, 212, 286 of SEQ ID NO:4.

18. The composition of claim 7, wherein the LF polypeptide is N-glycosylated or O-glycosylated.

19. The composition of claim 7, wherein the target antigen is N-glycosylated or O-glycosylated.

20. The composition of claim 19, where the LF polypeptide is glycosylated on at least one residue selected from residues 62, 212, 286 of SEQ ID NO:4.

* * * * *

SEQUENCE LISTING

```
<160> NUMBER OF SEQ ID NOS: 12

<210> SEQ ID NO 1
<211> LENGTH: 809
<212> TYPE: PRT
<213> ORGANISM: Bacillus anthracis

<400> SEQUENCE: 1

Met Asn Ile Lys Lys Glu Phe Ile Lys Val Ile Ser Met Ser Cys Leu
1               5                   10                  15
```

-continued

```
Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ser Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
            340                 345                 350

Lys Arg Ile Gln Ile Asp Ser Ser Asp Phe Leu Ser Thr Glu Glu Lys
        355                 360                 365

Glu Phe Leu Lys Lys Leu Gln Ile Asp Ile Arg Asp Ser Leu Ser Glu
    370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
            420                 425                 430
```

```
Asp Ser Pro Ser Ile Asn Leu Asp Val Arg Lys Gln Tyr Lys Arg Asp
        435                 440                 445

Ile Gln Asn Ile Asp Ala Leu Leu His Gln Ser Ile Gly Ser Thr Leu
    450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
        515                 520                 525

Asn Glu Arg Leu Lys Trp Arg Ile Gln Leu Ser Pro Asp Thr Arg Ala
    530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
                565                 570                 575

Arg Ile Asp Ala Lys Val Val Pro Lys Ser Lys Ile Asp Thr Lys Ile
            580                 585                 590

Gln Glu Ala Gln Leu Asn Ile Asn Gln Glu Trp Asn Lys Ala Leu Gly
        595                 600                 605

Leu Pro Lys Tyr Thr Lys Leu Ile Thr Phe Asn Val His Asn Arg Tyr
    610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
        675                 680                 685

Lys Gly Leu Tyr Val Pro Glu Ser Arg Ser Ile Leu Leu His Gly Pro
    690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
        755                 760                 765

Phe Phe Ala Glu Ala Phe Arg Leu Met His Ser Thr Asp His Ala Glu
    770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805
```

<210> SEQ ID NO 2
<211> LENGTH: 776
<212> TYPE: PRT
<213> ORGANISM: Bacillus anthracis

<400> SEQUENCE: 2

-continued

```
Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
            260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
    290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
            340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
    370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415
```

```
Gln Asn Ile Asp Ala Leu Leu His Gln Ser Ile Gly Ser Thr Leu Tyr
            420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
    450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
            500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
    530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575

Pro Lys Tyr Thr Lys Leu Ile Thr Phe Asn Val His Asn Arg Tyr Ala
            580                 585                 590

Ser Asn Ile Val Glu Ser Ala Tyr Leu Ile Leu Asn Glu Trp Lys Asn
        595                 600                 605

Asn Ile Gln Ser Asp Leu Ile Lys Lys Val Thr Asn Tyr Leu Val Asp
    610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
                645                 650                 655

Gly Leu Tyr Val Pro Glu Ser Arg Ser Ile Leu Leu His Gly Pro Ser
            660                 665                 670

Lys Gly Val Glu Leu Arg Asn Asp Ser Glu Gly Phe Ile His Glu Phe
        675                 680                 685

Gly His Ala Val Asp Asp Tyr Ala Gly Tyr Leu Leu Asp Lys Asn Gln
    690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
                725                 730                 735

Phe Ala Glu Ala Phe Arg Leu Met His Ser Thr Asp His Ala Glu Arg
            740                 745                 750

Leu Lys Val Gln Lys Asn Ala Pro Lys Thr Phe Gln Phe Ile Asn Asp
        755                 760                 765

Gln Ile Lys Phe Ile Ile Asn Ser
    770                 775


<210> SEQ ID NO 3
<211> LENGTH: 288
<212> TYPE: PRT
<213> ORGANISM: Bacillus anthracis

<400> SEQUENCE: 3

Met Asn Ile Lys Lys Glu Phe Ile Lys Val Ile Ser Met Ser Cys Leu
1               5                   10                  15
```

Val Thr Ala Ile Thr Leu Ser Gly Pro Val Phe Ile Pro Leu Val Gln
20 25 30

Gly Ala Gly Gly His Gly Asp Val Gly Met His Val Lys Glu Lys Glu
35 40 45

Lys Asn Lys Asp Glu Asn Lys Arg Lys Asp Glu Glu Arg Asn Lys Thr
50 55 60

Gln Glu Glu His Leu Lys Glu Ile Met Lys His Ile Val Lys Ile Glu
65 70 75 80

Val Lys Gly Glu Glu Ala Val Lys Lys Glu Ala Ala Glu Lys Leu Leu
85 90 95

Glu Lys Val Pro Ser Asp Val Leu Glu Met Tyr Lys Ala Ile Gly Gly
100 105 110

Lys Ile Tyr Ile Val Asp Gly Asp Ile Thr Lys His Ile Ser Leu Glu
115 120 125

Ala Leu Ser Glu Asp Lys Lys Lys Ile Lys Asp Ile Tyr Gly Lys Asp
130 135 140

Ala Leu Leu His Glu His Tyr Val Tyr Ala Lys Glu Gly Tyr Glu Pro
145 150 155 160

Val Leu Val Ile Gln Ser Ser Glu Asp Tyr Val Glu Asn Thr Glu Lys
165 170 175

Ala Leu Asn Val Tyr Tyr Glu Ile Gly Lys Ile Leu Ser Arg Asp Ile
180 185 190

Leu Ser Lys Ile Asn Gln Pro Tyr Gln Lys Phe Leu Asp Val Leu Asn
195 200 205

Thr Ile Lys Asn Ala Ser Asp Ser Asp Gly Gln Asp Leu Leu Phe Thr
210 215 220

Asn Gln Leu Lys Glu His Pro Thr Asp Phe Ser Val Glu Phe Leu Glu
225 230 235 240

Gln Asn Ser Asn Glu Val Gln Glu Val Phe Ala Lys Ala Phe Ala Tyr
245 250 255

Tyr Ile Glu Pro Gln His Arg Asp Val Leu Gln Leu Tyr Ala Pro Glu
260 265 270

Ala Phe Asn Tyr Met Asp Lys Phe Asn Glu Gln Glu Ile Asn Leu Ser
275 280 285

<210> SEQ ID NO 4
<211> LENGTH: 255
<212> TYPE: PRT
<213> ORGANISM: Bacillus anthracis

<400> SEQUENCE: 4

Ala Gly Gly His Gly Asp Val Gly Met His Val Lys Glu Lys Glu Lys
1 5 10 15

Asn Lys Asp Glu Asn Lys Arg Lys Asp Glu Glu Arg Asn Lys Thr Gln
20 25 30

Glu Glu His Leu Lys Glu Ile Met Lys His Ile Val Lys Ile Glu Val
35 40 45

Lys Gly Glu Glu Ala Val Lys Lys Glu Ala Ala Glu Lys Leu Leu Glu
50 55 60

Lys Val Pro Ser Asp Val Leu Glu Met Tyr Lys Ala Ile Gly Gly Lys
65 70 75 80

Ile Tyr Ile Val Asp Gly Asp Ile Thr Lys His Ile Ser Leu Glu Ala
85 90 95

Leu Ser Glu Asp Lys Lys Lys Ile Lys Asp Ile Tyr Gly Lys Asp Ala

```
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser
                245                 250                 255


<210> SEQ ID NO 5
<211> LENGTH: 104
<212> TYPE: PRT
<213> ORGANISM: Bacillus anthracis

<400> SEQUENCE: 5

Gly Lys Ile Leu Ser Arg Asp Ile Leu Ser Lys Ile Asn Gln Pro Tyr
1               5                   10                  15

Gln Lys Phe Leu Asp Val Leu Asn Thr Ile Lys Asn Ala Ser Asp Ser
            20                  25                  30

Asp Gly Gln Asp Leu Leu Phe Thr Asn Gln Leu Lys Glu His Pro Thr
        35                  40                  45

Asp Phe Ser Val Glu Phe Leu Glu Gln Asn Ser Asn Glu Val Gln Glu
    50                  55                  60

Val Phe Ala Lys Ala Phe Ala Tyr Tyr Ile Glu Pro Gln His Arg Asp
65                  70                  75                  80

Val Leu Gln Leu Tyr Ala Pro Glu Ala Phe Asn Tyr Met Asp Lys Phe
                85                  90                  95

Asn Glu Gln Glu Ile Asn Leu Ser
            100


<210> SEQ ID NO 6
<211> LENGTH: 23
<212> TYPE: PRT
<213> ORGANISM: Unknown
<220> FEATURE:
<221> NAME/KEY: source
<223> OTHER INFORMATION: /note="Description of Unknown: Signal peptide"

<400> SEQUENCE: 6

Met Ala Pro Phe Glu Pro Leu Ala Ser Gly Ile Leu Leu Leu Leu Trp
1               5                   10                  15

Leu Ile Ala Pro Ser Arg Ala
            20


<210> SEQ ID NO 7
<211> LENGTH: 100
<212> TYPE: PRT
```

<213> ORGANISM: Mycobacterium tuberculosis

<400> SEQUENCE: 7

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```

<210> SEQ ID NO 8
<211> LENGTH: 95
<212> TYPE: PRT
<213> ORGANISM: Mycobacterium tuberculosis

<400> SEQUENCE: 8

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 9
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
ggaggaacat atggcgggcg gtcatggtga tg 32

<210> SEQ ID NO 10
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
ctaggatcct taccgttgat ctttaagttc ttcc 34

-continued

```
<210> SEQ ID NO 11
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

aauaaa                                                                  6


<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 12

His His His His His His
1               5
```